United States Patent
Grammenos et al.

(10) Patent No.: US 6,329,359 B1
(45) Date of Patent: *Dec. 11, 2001

(54) SUBSTITUTED BENZYL OXIMINO COMPOUNDS

(75) Inventors: Wassilios Grammenos, Ludwigshafen; Hubert Sauter; Herbert Bayer, both of Mannheim; Thomas Grote, Schifferstadt; Andreas Gypser, Mannheim; Reinhard Kirstgen, Neustadt; Bernd Müller, Frankenthal; Arne Ptock, Ludwigshafen; Franz Röhl, Schifferstadt; Roland Götz, Rothenburg; Gisela Lorenz, Neustadt; Eberhard Ammermann, Heppenheim; Siegfried Strathmann, Limburgerhof; Volker Harries, Frankenthal, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,878
(22) PCT Filed: Apr. 2, 1998
(86) PCT No.: PCT/EP98/01942
§ 371 Date: Oct. 13, 1999
§ 102(e) Date: Oct. 13, 1999
(87) PCT Pub. No.: WO98/47886
PCT Pub. Date: Oct. 29, 1998

(30) Foreign Application Priority Data

Apr. 18, 1997 (DE) .............................. 197 16 237

(51) Int. Cl.$^7$ ...................... A61K 31/15; A61K 31/336; C07C 249/08; C07C 251/18; C07D 303/36
(52) U.S. Cl. .......................... 514/183; 514/475; 514/640; 549/523; 549/551; 564/256; 564/264; 564/265; 548/965; 548/967

(58) Field of Search ................................ 514/183, 475, 514/640; 548/965, 967; 549/523, 551; 564/256, 264, 265

(56) References Cited

U.S. PATENT DOCUMENTS 5,387,607  2/1995  Brand et al. .

FOREIGN PATENT DOCUMENTS

| 2043733 | 12/1991 | (CA) . |
|---|---|---|
| 2104806 | 3/1994 | (CA) . |
| 592 641 | 10/1977 | (CH) . |
| 129 889 | 1/1985 | (EP) . |
| 426 460 | 5/1991 | (EP) . |
| 472 300 | 2/1992 | (EP) . |
| 92/13830 | 8/1992 | (WO) . |
| 92/18487 | 10/1992 | (WO) . |
| 92/18494 | 10/1992 | (WO) . |
| 93/15046 | 8/1993 | (WO) . |

OTHER PUBLICATIONS

March, J. Adv. Org. Chem. (4$^{th}$ ed. 1992) pp. 425–428, 826–827.*
Langhals et al., Verlag Chem. Chem. Ber. 114, 3831–3854 (1981).
Tetrahedron Lett. vol. 21, 2893–2896; Santelli (1980).
Beilsteins handbuch der orgn. Chem. 4, Aufl. 3 and 4. Bd 18, (1976) 4364–4365.

* cited by examiner

Primary Examiner—T. A. Solola
(74) Attorney, Agent, or Firm—Keil & Weinkauf

(57) ABSTRACT

The present invention relates to benzyloxyimino compounds of the formula I,

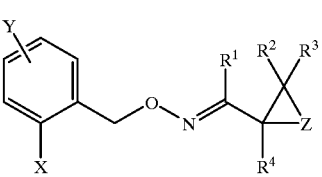

where: $R^1$ to $R^4$, X, Y, and Z are as defined in the specification.

21 Claims, No Drawings

SUBSTITUTED BENZYL OXIMINO COMPOUNDS

This is a 371 of PCT/EP98/01942 filed Apr. 2, 1998.

The present invention relates to benzyloxyimino compounds of the formula I,

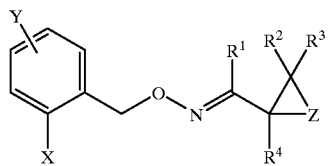

where:
- X is $N(COOCH_3)-OCH_3$, $C(COOCH_3)=CH-OCH_3$, $C(COOCH_3)=N-OCH_3$, $C(CONHCH_3)=N-OCH_3$ or $C(COOCH_3)=CH-CH_3$;
- Y is hydrogen, halogen, $C_1-C_4$-alkyl, $C_1-C_4$-haloalkyl or $C_1-C_4$-alkoxy;
- Z is oxygen, $C(R^a)_2$ or $NR^a$, where
    $R^a$ is hydrogen or $C_1-C_4$-alkyl and, in the case of $C(R^a)_2$, can be identical or different;
- $R^1$ is halogen, $C_1-C_4$-alkyl, $C_1-C_4$-haloalkyl or $C_1-C_4$-alkoxy;
- $R^2$ is hydrogen, halogen, $C_1-C_4$-alkyl, $C_1-C_4$-alkoxy or is phenyl with or without substitution by customary groups;
- $R^3$ is hydrogen, halogen, $C_1-C_4$-alkyl or $C_1-C_4$-alkoxy;
- $R^4$ is $C_1-C_4$-alkyl or
    phenyl with or without substitution by 1–3 substituents from the following group: halogen, $C_1-C_4$-alkyl, $C_1-C_4$-haloalkyl, $C_1-C_4$-alkoxy, $C_1-C_4$-haloalkoxy or $C(R^b)=N-OR^c$, where
    $R^b$ is hydrogen or $C_1-C_4$-alkyl and
    $R^c$ is $C_1-C_4$-alkyl, $C_3-C_4$-alkenyl or $C_3-C_4$-alkynyl.

Additionally, the invention relates to processes and intermediates for preparing the compounds I, to compositions and to the use of the compounds I for controlling harmful fungi and animal pests.

Phenylcarbamates having a methoxyimino group in the ortho position are disclosed in WO-A 93/15,046. α-Phenylacrylic acid and α-phenyl-α-methoxyiminoacetic acid derivatives having a methoxyimino group in the ortho position are known from EP-A 426 460, EP-A 460 575, EP-A 472 300, EP-A 585 751, WO-A 92/13,830, WO-A 92/18,487, WO-A 92/18,494, JP-A 05/201,946 and JP-A 05/255,012. The compounds described therein carry a $CH_2O-N=CR'R''$ group in the position ortho to the group corresponding to X. The general definitions of the radicals R' and R'' include the definition of the radical $R^1$ in formula I and additionally allow cycloalkyl and to some extent heterocyclyl substituents.

EP-A 463 488 and WO-A 90/07,493 disclose by way of example α-phenylacrylic acid and α-phenyl-α-methoxyiminoacetic acid derivatives in which the $CH_2O-N=CR'R''$ group carries alkyl and cyclopropyl, oxiranyl, or aziridinyl radicals as substituents R' and R''.

The compounds described in the abovementioned publications are suitable for use as crop protection agents against harmful fungi and to some extent against animal pests.

However, in many instances their activity is not satisfactory. It is an object of the present invention, therefore, to provide compounds having improved activity.

We have found that this object is achieved by the substituted benzyloxyimino compounds of the formula I. Furthermore, we have found intermediates and processes for preparing the compounds I, and the use of the compounds I and of compositions comprising them for controlling harmful fungi and animal pests. Preference is given to the fungicidal activity.

The compounds of the formula I differ from the compounds disclosed in the abovementioned publications EP-A 463 488 and WO-A 90/07,493 in the substitution of the methoxyimino group by the radical $R^4$, which cannot be hydrogen. In comparison to the known compounds, the compounds of the formula I have improved activity against harmful fungi and animal pests.

The compounds of the formula I can be obtained per se by the methods described in EP-A 463 488 and WO-A 90/07, 493.

In particular, the compounds of the formula I in which Z is oxygen and $C(R^a)_2$ are obtained by reacting an oxime of the formula II with a benzyl compound of the formula III.

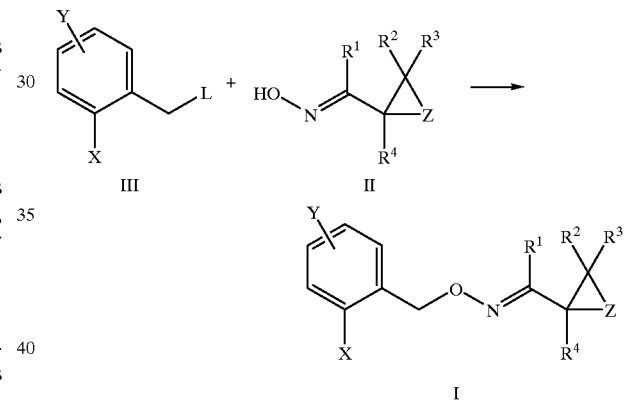

In the formula III, L is a nucleophilically replaceable group, for example halogen, such as fluorine, chlorine, bromine or iodine, in particular chlorine or bromine, or alkyl- or arylsulfonates, such as mesylate or tosylate.

1. The reaction of the oxime II with the benzyl compound III is carried out in a known manner at from $-10°$ C. to $80°$ C., preferably $0°$ C. to $65°$ C., in an inert organic solvent in the presence of a base [cf. EP-A 463 488].

In general, the reactants are reacted with one another in equimolar amounts. To improve the yield, it may be advantageous to employ an excess of II, based on III.

The benzyl compounds of the formula III required for preparing the compounds I are known from the literature [EP-A 420 091; EP-A 513 580; WO-A 93/15,046; WO-A 94/05,620] and can be prepared according to the cited literature.

The starting materials IIA required for preparing the compounds I in which Z is oxygen can be prepared as follows:

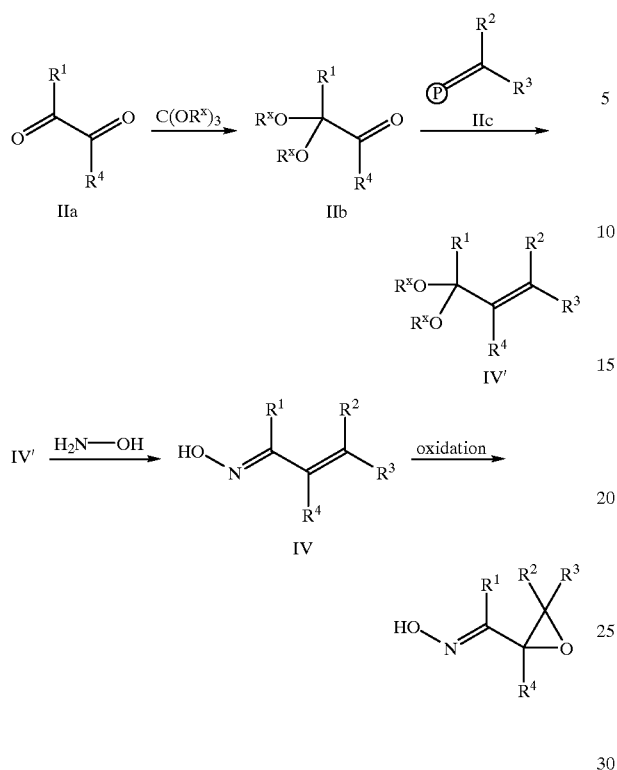

2A. In the above reaction scheme, $R^x$ is a $C_1$–$C_{10}$-alkyl radical and $\hat{P}$ in the formula IIc is a phosphoranyl radical such as, for example, triphenylphosphoranyl.

The acetalization of the α,β-diketone IIa to IIb is usually carried out at from −20° C. to 120° C., preferably 0° C. to 85° C., in an inert organic solvent in the presence of an acid [cf. Khim.-Farm. Zh. (1986), p. 606; J. Chem. Res. Miniprint (1982), p. 2528].

Suitable for use as solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxan, anisole and tetrahydrofuran, alcohols such as methanol, ethanol, n-propanol, isopropanol, n-butanol and tert-butanol, and dimethyl sulfoxide, dimethylformamide and dimethylacetamide, particularly preferably toluene, methanol, ethanol and dimethylacetamide. It is also possible to use mixtures of the solvents mentioned.

Suitable acids and acid catalysts are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid.

In general, the acids are employed in catalytic amounts, but it is also possible to employ them in equimolar amounts, in excess or, if appropriate, as solvent.

In general, the reactants are reacted with one another in equimolar amounts. To improve the yield, it may be advantageous to employ an excess of $C(OR^x)_3$, based on IIa.

The diketones IIa are commercially available or known from the literature [J. Am. Chem. Soc. (1996), p. 12588; J. Chem. Soc. Chem. Commun. (1987), p. 692; Khim.-Farm. Zh. (1986), p. 606], or they can be prepared according to the literature cited.

2B. In a Wittig reaction, the compound IIb is converted into the α,β-unsaturated acetal IV' using a phosphorane of the formula IIc.

The Wittig reaction is usually carried out at from −78° C. to 85° C., preferably −10° C. to 65° C., in an inert organic solvent in the presence of a base [cf. EP-A 513 580].

Suitable for use as solvents are aromatic hydrocarbons such as toluene, o-, m- and p-xylene, ethers such as diethyl ether, diisopropyl ether, tert-butyl methyl ether, dioxan, anisole and tetrahydrofuran, and dimethyl sulfoxide, dimethylformamide and dimethylacetamide, particularly preferably tetrahydrofuran, tert-butyl methyl ether, dimethylformamide and dimethylacetamide. It is also possible to employ mixtures of the solvents mentioned.

In general, suitable bases are inorganic compounds such as alkali metal and alkaline earth metal hydrides such as lithium hydride, sodium hydride, potassium hydride and calcium hydride, alkali metal amides such as lithium amide, sodium amide and potassium amide, organometallic compounds, in particular alkali metal alkyls such as methyllithium, butyllithium and phenyllithium, alkylmagnesium halides such as methylmagnesium chloride, and alkali metal and alkaline earth metal alkoxides such as sodium methoxide, sodium ethoxide, potassium methoxide, potassium tert-butoxide and dimethoxymagnesium. Particular preference is given to potassium tert-butoxide, sodium tert-butoxide, sodium methoxide, potassium methoxide and sodium hydroxide.

In general, the bases are used in catalytic amounts, but it is also possible to employ them in equimolar amounts, in excess or, if appropriate, as solvent.

In general, the reactants are reacted with one another in equimolar amounts. To improve the yield, it may be advantageous to employ an excess of IIc, based on IIb.

The phosphoranes of the formula IIc are commercially available or known from the literature [cf. Lieges Ann. Chem. (1967), p. 708; J. Org. Chem. (1983), p. 4860], or they can be prepared according to the literature cited.

2C. In general, the α,β-unsaturated acetal of the formula IV' is reacted with hydroxylamine, or one of its acid addition salts, at from −10° C. to 86° C., preferably 0° C. to 65° C., in an inert organic solvent, if appropriate in the presence of a base, to give the oxime of the formula IV [cf. Journal of Organic Chemistry (1993), p. 759; Helv. Chim. Acta (1960), p. 1546].

Suitable for use as solvents are ethers such as diethyl ether, diisopropyl ether, tert-butyl methyl ether, dioxan, anisole and tetrahydrofuran, nitriles such as acetonitrile and propionitrile, alcohols such as methanol, ethanol, n-propanol, isopropanol, n-butanol and tert-butanol, particularly preferably methanol and ethanol. It is also possible to employ mixtures of the solvents mentioned.

In general, suitable bases are organic bases, for example tertiary amines such as trimethylamine, triethylamine, triisopropylethylamine and N-methylpiperidine, pyridine, substituted pyridines such as collidine, lutidine and 4-dimethylaminopyridine, and bicyclic amines. Particular preference is given to triethylamine and pyridine.

In general, the bases are employed in catalytic amounts, but it is also possible to employ them in equimolar amounts, in excess or, if appropriate, as solvent.

In general, the reactants are reacted with one another in equimolar amounts. To improve the yield, it may be advantageous to employ an excess of hydroxylamine, based on IV,.

2D. The α,β-unsaturated oxime of the formula IV is converted into the oxirane IIA by oxidation.

In general, the epoxidation is carried out at from −78° C. to 45° C., preferably −20° C. to 30° C., in an inert organic solvent [cf. Houben-Weyl, Methoden der organischen Chemie, Volume 4/1a, 4th edition, p. 182–239, Georg Thieme Verlag, Stuttgart 1981].

Suitable for use as oxidizing agents are oxygen donors such as inorganic peroxides, for example hydrogen peroxide and tert-butyl hydroperoxide, or organic peracids, for example perbenzoic acid, 3-chloroperbenzoic acid or peracetic acid. In general, they are reacted with one another in equimolar amounts. To improve the yield, it may be advantageous to employ a 3- to 5-fold excess of the oxidizing agent, based on the compound IV.

Suitable for use as solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, and dimethyl sulfoxide, dimethylformamide and dimethylacetamide, particularly preferably toluene, methylene chloride and chlorobenzene. It is also possible to use mixtures of the solvents mentioned.

The starting materials IIB required for preparing the compounds I where Z is C(R$^a$)$_2$ can be prepared by routes known from the literature as follows:

3. To prepare the ketone of the formula IIf, the cyclopropylcarboxylic acid derivative of the formula IIf' [for the preparation see, for example, EP-A 459 285; Anal. Chem. 24 (1952), p. 623, Journal of organic Chemistry 31, (1966), p. 1379] can be reacted with organometallic reagents Mt-R$^1$, in particular Grignard or lithium reagents [cf. Bull. Chem. Soc. Jap. 68 (1995), p. 341; J. Am. Chem. Soc. 76 (1954), p. 2244; Chem. Ber. 114 (1981), p. 3831; Helv. Chim. Acta 42 (1959), p. 2394].

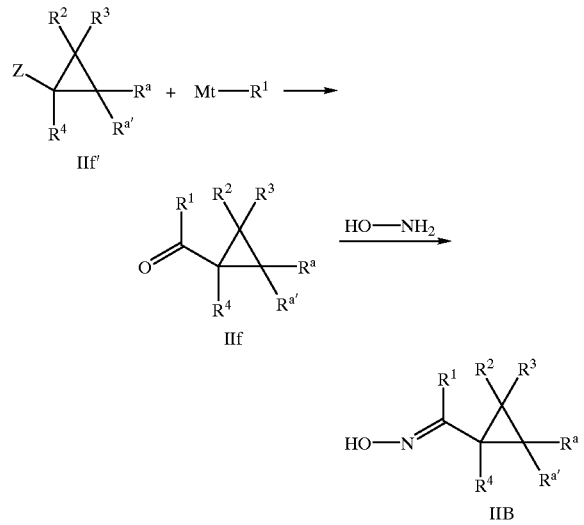

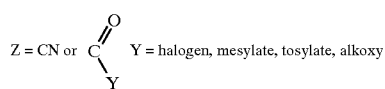

Furthermore, compounds of the formula I in which Z is oxygen are obtained by reacting a benzyl compound of the formula III with an oxime of the formula IV to give an oxime ether of the formula V which is subsequently converted into a compound of the formula I by oxidation.

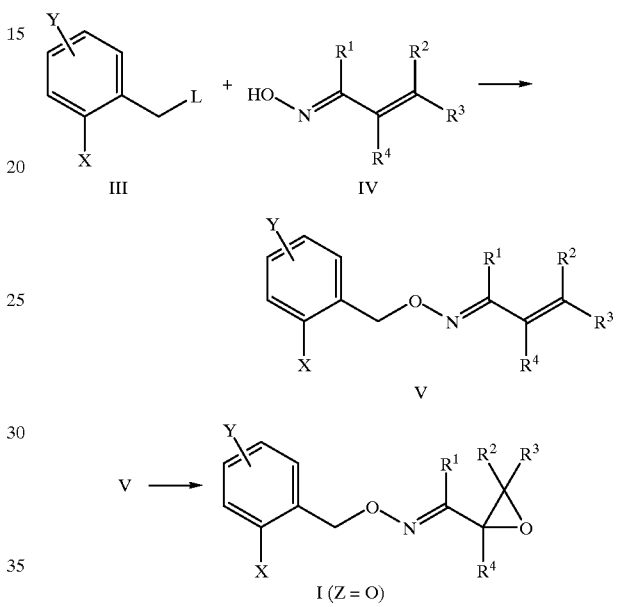

4. The preparation of the oxime ether V is carried out in a conventional manner, generally at from −20° C. to 85° C., preferably 0° C. to 65° C., in an inert organic solvent in the presence of a base [cf. EP-A 463 488].

4A. A synthetic route to the oxime IV required for preparing the compounds V has already been described in connection with the synthesis of the compounds IIA.

4B. The oxidation of the unsaturated oxime ether V to the compound of the formula I in which Z is oxygen is carried out by a method similar to the oxidation of the compound IV to the oxirane IIA.

The oxidation is usually carried out at from −78° C. to 45° C., preferably −20° C. to 30° C., in an inert organic solvent.

Compounds of the formula I in which Z is NH are obtained by reacting compounds of the formula I in which Z is oxygen with metal azides.

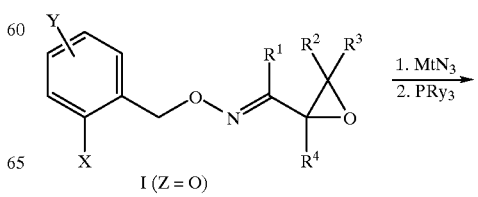

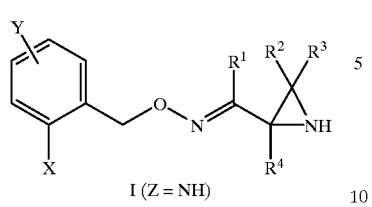

I (Z = NH)

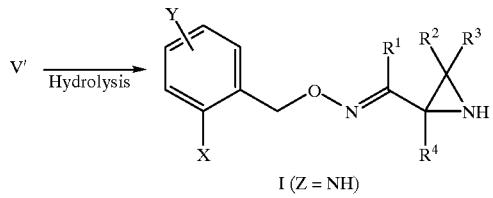

I (Z = NH)

5. This reaction is usually carried out at from −20° C. to 120° C., preferably −20° C. to 100° C., in an inert organic solvent [cf. Journal of Heterocycl. Chemistry (1991), p. 473 and Tetrahedron (1991), p. 5287].

In the reaction scheme above, Mt is an ion from the group of the alkali, alkaline earth or transition metals, or trialkylsilyl, for example sodium or trimethylsilyl; $R^Y$ is a $C_1$–$C_{10}$-alkoxy radical, in particular an ethoxy radical or aryl, for example a phenyl radical.

Suitable for use as solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxan, anisole and tetrahydrofuran, ketones such as acetone, methyl ethyl ketone, diethyl ketone and tert-butyl methyl ketone, and dimethyl sulfoxide, dimethylformamide and dimethylacetamide, or water, particularly preferably acetone, dichloromethane, toluene and a water/acetone mixture. It is also possible to use mixtures of the solvents mentioned.

In general, the reactants are reacted with one another in equimolar amounts. To improve the yield, it may be advantageous to employ an excess of $MtN_3$, based on I (Z=O).

Additionally, compounds of the formula I in which Z is NH are obtained by reacting compounds of the formula V with ethyl-1-azido-N-(methylsulfonyl)formamidate and subsequently hydrolyzing the resulting compound V'.

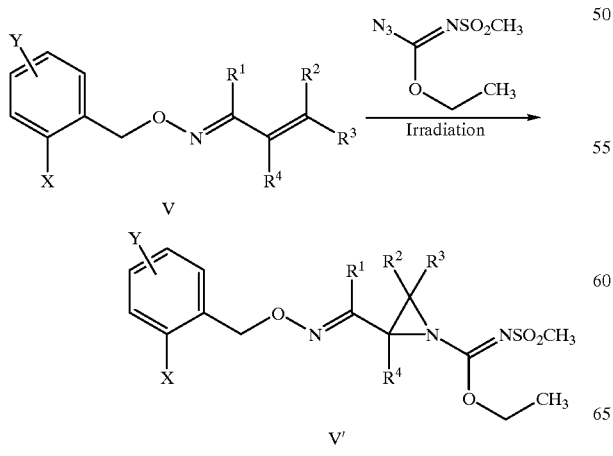

6A. Suitable reaction conditions for reacting the oxime ether V with ethyl-1-azido-N-(methylsulfonyl)formamidate are given in Journal of Organic Chemistry (1989), p. 3945.

Suitable for use as solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ketones such as acetone, methyl ethyl ketone, diethyl ketone and tert-butyl methyl ketone, and dimethyl sulfoxide, dimethylformamide and dimethylacetamide, particularly preferably cyclohexane, methylene chloride, toluene and acetone. It is also possible to use mixtures of the solvents mentioned.

In general, the reactants are reacted with one another in equimolar amounts. To improve the yield, it may be advantageous to employ a 3- to 10-fold excess of ethyl 1-azido-N-(methylsulfonyl)formamidate, based on V.

6B. Ethyl 1-azido-N-(methylsulfonyl)formamidate, required for preparing the compound V', is known from the literature [Journal of Organic Chemistry (1989), p. 3945] and can be prepared according to the literature cited.

The hydrolysis of the compound V' to give the aziridine of the formula I in which Z is NH is usually carried out at from 0° C. to 85° C., preferably 25° C. to 65° C., in an inert organic solvent in the presence of a base [cf. Journal of Organic Chemistry (1989), p. 3945].

Suitable for use as solvents are ethers such as dioxane, anisole and tetrahydrofuran, nitriles such as acetonitrile and propionitrile, ketones such as acetone, methyl ethyl ketone and diethyl ketone, alcohols such as methanol, ethanol, n-propanol, isopropanol, n-butanol and tert-butanol, and water, particularly preferably methanol, ethanol and water. It is also possible to use mixtures of the solvents mentioned.

In general, suitable bases are inorganic compounds such as alkali metal hydroxides and alkaline earth metal hydroxides such as lithium hydroxide, sodium hydroxide, potassium hydroxide and calcium hydroxide, alkali metal carbonates and alkaline earth metal carbonates such as lithium carbonate, potassium carbonate and calcium carbonate, and alkali metal bicarbonates such as sodium bicarbonate. Particular preference is given to sodium hydroxide and potassium hydroxide.

In general, the bases are employed in catalytic amounts, but it is also possible to employ them in equimolar amounts, in excess, or, if appropriate, as solvent.

Compounds of the formula I in which Z is N—$C_1$–$C_4$-alkyl are obtained by reacting compounds of the formula I in which Z is NH with alkylating agents.

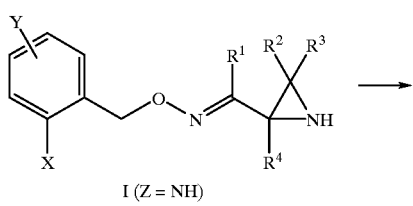

I (Z = NH)

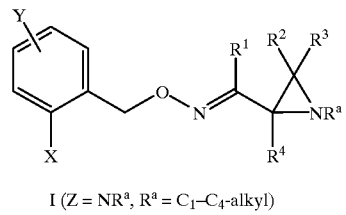

I (Z = NR$^a$, R$^a$ = C$_1$–C$_4$-alkyl)

7. The alkylation is usually carried out at from −30° C. to 120° C., preferably −10° C. to 100° C., in an inert organic solvent [cf. Synth. Commun. (1991), p. 239]

Suitable alkylating agents are, for example, alkyl halides such as methyl iodide and bromoethane, or dialkyl sulfates, for example dimethyl sulfate.

Suitable for use as solvents are ethers such as diethyl ether, diisopropyl ether, tert-butyl methyl ether, dioxan, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide, dimethylformamide and dimethylacetamide, particularly preferably tetrahydrofuran, acetonitrile, acetone and dimethylformamide. It is also possible to use mixtures of the solvents mentioned.

In general, suitable bases are inorganic compounds such as alkali metal hydroxides and alkaline earth metal hydroxides such as lithium hydroxide, sodium hydroxide, potassium hydroxide and calcium hydroxide, alkali metal hydrides and alkaline earth metal hydrides such as lithium hydride, sodium hydride, potassium hydride and calcium hydride, alkali metal carbonates and alkaline earth metal carbonates such as lithium carbonate, potassium carbonate and calcium carbonate, and alkali metal bicarbonates such as sodium bicarbonate, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium, furthermore organic bases, for example tertiary amines such as trimethylamine, triethylamine, triisopropylethylamine and N-methylpiperidine, pyridine, substituted pyridines such as collidine, lutidine and 4-dimethylaminopyridine, and bicyclic amines. Particular preference is given to NaHCO$_3$, K$_2$CO$_3$ and triethylamine.

In general, the bases are employed in catalytic amounts, but it is also possible to employ them in equimolar amounts, in excess, or, if appropriate, as solvent.

In general, the reactants are reacted with one another in equimolar amounts. To improve the yield, it may be advantageous to employ an excess of alkylating agent, based on I (Z═NH). To improve the yield, it may also be advantageous to add tetrabutylammonium halides, in particular tetrabutylammonium fluoride.

Alternatively to the direct oxidation of the oxime ether V described in Chapter 4A, compounds of the formula I in which Z is oxygen and X is C(═N—OCH$_3$)—CONHCH$_3$ are obtained by first converting compounds of the formula V in which X is C(═N—OCH$_3$)—COOCH$_3$ under customary condition [cf. EP-A 398 692; EP-A 477 631] into the carboxamide Va and subsequently converting the carboxamide Va into the compound I by oxidation.

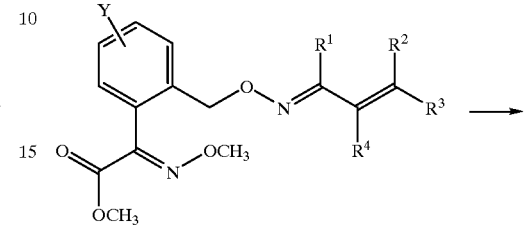

V

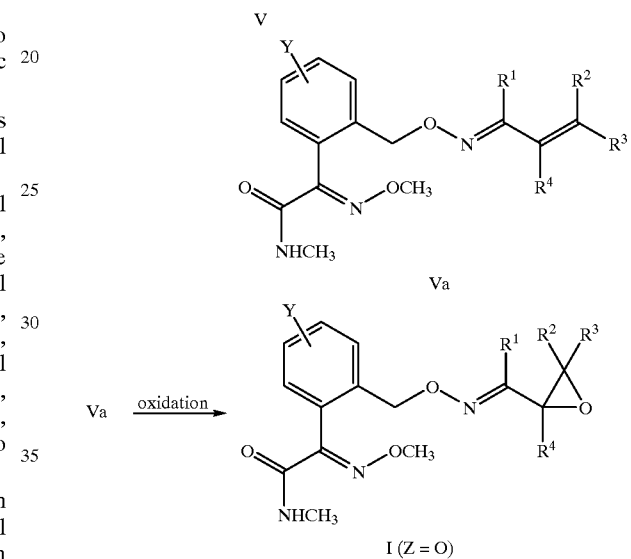

8. The oxidation of Va is carried out under the conditions given for the oxidation of the compound V in Chapter 4A.

The reaction mixtures are worked up in a customary manner, for example by mixing with water, phase separation and, if required, chromatographic purification of the crude products. Some of the intermediates and end products are obtained in the form of colorless or slightly brownish, viscous oils, which are purified or freed from volatile components under reduced pressure and at moderately elevated temperature. If the intermediates and end products are obtained as solids, purification can also be carried out by recrystallization or digestion.

Owing to their C═C and C═N double bonds, the preparation of the compounds I may yield E/Z isomer mixtures which can be separated into the individual compounds in a customary manner, for example by crystallization or chromatography.

However, if the synthesis yields isomer mixtures, a separation is generally not necessarily required since in some cases the individual isomers can be converted into one another during the preparation for use or upon use (for example under the action of light, acids or bases). Similar conversions may also occur after the use, for example in the treatment of plants in the treated plant or in the harmful fungus or animal pest to be controled.

In the group corresponding to X, with regard to the C═N and C═C double bond, preference is given to the E isomers of the compounds I (configuration based on the $OCH_3$ or $CH_3$ group in relation to the carbonyl group) with respect to their activity.

In the definitions of the symbols given in the above formulae, collective terms were used which generally represent the following substituents:

Halogen: fluorine, chlorine, bromine and iodine;

$C_1$–$C_4$-Alkyl: saturated straight-chain or branched hydrocarbon radicals having 1 to 4 carbon atoms, eg. methyl, ethyl, propyl, 1-methylethyl, butyl, 1-methylpropyl, 2-methylpropyl and 1,1-dimethylethyl;

$C_1$–$C_4$-Haloalkyl: straight-chain or branched alkyl groups having 1 to 4 carbon atoms (as mentioned above), it being possible for some or all of the hydrogen atoms in these groups to be replaced by halogen atoms as mentioned above, preferably fluorine, chlorine and bromine, eg. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$–$C_4$-Alkoxy: straight-chain or branched alkyl groups having 1 to 4 carbon atoms (as mentioned above) and attached to the skeleton via an oxygen atom (—O—);

$C_1$–$C_4$-Haloalkoxy: straight-chain or branched haloalkyl groups having 1 to 4 carbon atoms (as mentioned above) and attached to the skeleton via an oxygen atom (—O—);

$C_3$–$C_4$-Alkenyl: unsaturated, straight-chain or branched hydrocarbon radicals having 3 to 4 carbon atoms and a double bond in any position, eg. 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_3$–$C_4$-Alkynyl: straight-chain or branched hydrocarbon groups having 3 to 4 carbon atoms and a triple bond in any position, eg. 1-propynyl, 2-propynyl, 1-butynyl, 2-butynyl, 3-butynyl and 1-methyl-2-propynyl.

With respect to the substitution of the phenyl ring in the position of $R^2$, customary groups are in particular the following substituents: halogen, $C_1$–$C_4$-alkyl and $C_1$–$C_4$-haloalkyl.

With regard to the intended use of the compounds of the formula I, particular preference is given to the following definitions of the substituents, each being on their own or combined:

Particular preference is given to compounds of the formula I in which X is $N(COOCH_3)$—$OCH_3$.

Equally preferred are compounds I in which X is $C(CONHCH_3)$=N—$OCH_3$.

Furthermore, preference is given to compounds I in which X is $C(COOCH_3)$=CH—$OCH_3$, $C(COOCH_3)$=N—$OCH_3$ or $C(COOCH_3)$=CH—$CH_3$.

Additionally, preference is given to compounds I in which Y is hydrogen.

In the case that Y is not hydrogen, preference is given to compounds I in which Y is halogen, $C_1$–$C_2$-alkyl, $C_1$–$C_2$-haloalkyl or $C_1$–$C_2$-alkoxy, in particular fluorine, chlorine, methyl, trifluoromethyl or methoxy.

Additionally, in the case that Y is not hydrogen, preference is given to compounds I in which Y is in position 3 or 6.

Particular preference is given to compounds I in which Z is oxygen.

Equally preferred are compounds I in which Z is $NR^a$, in particular NH or. $NCH_3$.

Additionally, preference is given to compounds I in which Z is $C(R^a)2$.

Furthermore, particular preference is given to compounds I in which $R^1$ is halogen, in particular fluorine or chlorine.

Additionally, preference is given to compounds I in which $R^1$ is $C_1$–$C_4$-alkyl, in particular methyl.

Equally preferred are compounds I in which $R^1$ is $C_f$–$C_4$-haloalkyl, in particular trifluoromethyl.

Furthermore, preference is given to compounds I in which $R^2$ or $R^3$ is hydrogen.

Additionally, preference is given to compounds I in which $R^2$ or $R^3$ is $C_1$–$C_2$-alkyl.

Furthermore, preference is given to compounds I in which $R^2$ is hydrogen and $R^3$ is $C_1$–$C_4$-alkyl.

Particular preference is given to compounds I in which $R^2$ is phenyl which is substituted by customary groups.

In the case that Z is oxygen, preference is given to compounds I in which $R^2$ is hydrogen and $R^3$ is $C_1$–$C_4$-alkyl or phenyl which is substituted by customary groups.

Equally preferred are compounds I in which $R^4$ is phenyl with or without substitution by 1–3 substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=N—$OR^c$.

Furthermore, preference is given to compounds I in which $R^4$ is phenyl which may be substituted by customary groups in position 4.

The particularly preferred embodiments of the intermediates correspond, with respect to the variables, to those of the radicals $R^1$, $R^2$, $R^3$ and $R^4$ of formula I.

Particular preference is given to compounds of the formula Ia.1 where Y is hydrogen, 6-methyl, 6-chloro or 3- or 6- fluoro, $R^1$ is methyl, ethyl, chloro, trifluoromethyl or methoxy, $R^2$ is hydrogen or methyl, $R^3$ is methyl, ethyl, n- or isopropyl or n- or tert-butyl and $R^4$ is methyl, ethyl, n- or isopropyl, n- or tert-butyl or unsubstituted or halogen-, methyl-, methoxy- or alkoxyiminomethylene-substituted phenyl.

Ia.1

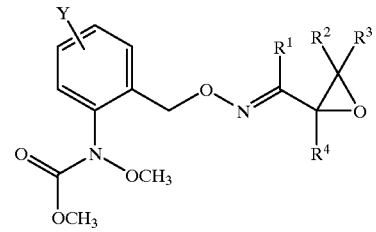

Furthermore, preference is given to compounds of the formula Ia.2 where Y is hydrogen, 6-methyl, 6-chloro or 3- or 6- fluoro, $R^1$ is methyl, ethyl, chloro, trifluoromethyl or methoxy, $R^2$ is hydrogen or methyl, $R^3$ is methyl, ethyl, n- or isopropyl or n- or tert-butyl and $R^4$ is methyl, ethyl, n- or isopropyl, n- or tert-butyl or unsubstituted or halogen-, methyl-, methoxy- or alkoxyiminomethylene-substituted phenyl.

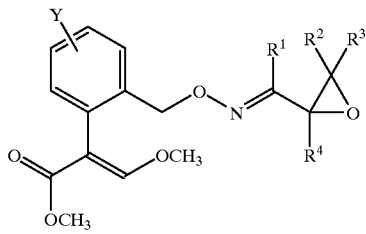

Ia.2

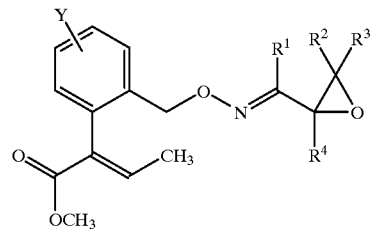

Ia.5

Likewise, particular preference is given to compounds of the formula Ia.3 where Y is hydrogen, 6-methyl, 6-chloro or 3- or 6-fluoro, $R^1$ is methyl, ethyl, chloro, trifluoromethyl or methoxy, $R^2$ is hydrogen or methyl, $R^3$ is methyl, ethyl, n- or isopropyl or n- or tert-butyl and $R^4$ is methyl, ethyl, n- or isopropyl, n- or tert-butyl or unsubstituted or halogen-, methyl-, methoxy- or alkoxyiminomethylene-substituted phenyl.

Moreover, particular preference is given to compounds IB where Y, $R^2$ and $R^a$ are hydrogen, $R^1$ is methyl and X is $N(COOCH_3)-OCH_3$, $C(COOCH_3)=COCH_3$, $C(COOCH_3)=NOCH_3$ or $C(COOCH_3)=C-CH_3$, $R^3$ is hydrogen or methyl, $R^4$ is methyl or is phenyl which is unsubstituted or substituted by para halogen and $R^{a'}$ is hydrogen or methyl.

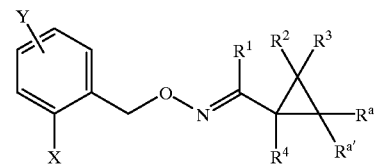

IB

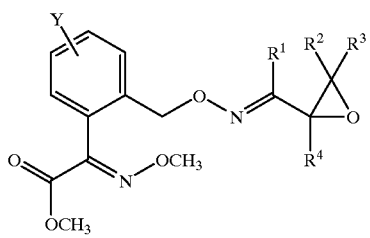

Ia.3

Furthermore particular preference is given to compounds of the formula Ia.4 where Y is hydrogen, 6-methyl, 6-chloro or 3- or 6-fluoro, $R^1$ is methyl, ethyl, chloro, trifluoromethyl or methoxy, $R^2$ is hydrogen or methyl, $R^3$ is methyl, ethyl, n- or isopropyl or n- or tert-butyl and $R^4$ is methyl, ethyl, n- or isopropyl, n- or tert-butyl or unsubstituted or halogen-, methyl-, methoxy- or alkoxyiminomethylene-substituted phenyl.

Likewise, particular preference is given to compounds IC where Y is hydrogen, $R^1$ is methyl, X is $N(COOCH_3)-OCH_3$, $C(COOCH_3)=COCH_3$, $C(COOCH_3)=NOCH_3$ or $C(COOCH_3)=C-CH_3$, $R^2$ is hydrogen, $R^3$ is hydrogen or methyl, $R^4$ is methyl or is phenyl which is unsubstituted or substituted by para halogen and $R^a$ is hydrogen, methyl or ethyl.

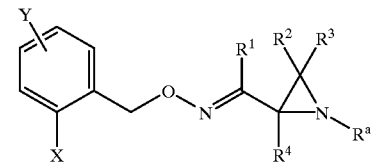

IC

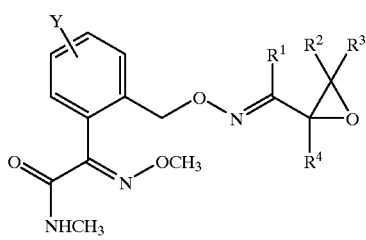

Ia.4

Particular preference is also given to compounds of the formula Ia.5 where Y is hydrogen, 6-methyl, 6-chloro or 3- or 6- fluoro, $R^1$ is methyl, ethyl, chloro, trifluoromethyl or methoxy, $R^2$ is hydrogen or methyl, $R^3$ is methyl, ethyl, n- or isopropyl or n- or tert-butyl and $R^4$ is methyl, ethyl, n- or isopropyl, n- or tert-butyl or unsubstituted or halogen-, methyl-, methoxy- or alkoxyiminomethylene-substituted phenyl.

With respect to their use, particular preference is given to the compounds I compiled in the tables below. Moreover, the groups mentioned for a substituent in the tables are, by themselves and independently of the combination in which they are mentioned, a particularly preferred embodiment of the substituent in question.

Table 1
Compounds of the formula Ia.1 in which the combination of the substituents Y, $R^1$, $R^2$, $R^3$ and $R^4$ corresponds for each compound to a row of table A Table 2
Compounds of the formula Ia.2 in which the combination of the substituents Y, $R^1$, $R^2$, $R^3$ and $R^4$ corresponds for each compound to a row of table A Table 3
Compounds of the formula Ia.3 in which the combination of the substituents Y, $R^1$, $R^2$, $R^3$ and $R^4$ corresponds for each compound to a row of table A Table 4
Compounds of the formula Ia.4 in which the combination of the substituents Y, $R^1$, $R^2$, $R^3$ and $R^4$ corresponds for each compound to a row of table A Table 5

Compounds of the formula Ia.5 in which the combination of the substituents Y, $R^1$, $R^2$, $R^3$ and $R^4$ corresponds for each compound to a row of table A Table 6

Compounds of the formula I.B in which Y, $R^2$ and $R^a$ are each hydrogen, $R^1$ is methyl and the combination of the radicals X, $R^3$, $R^4$ and $R^{a'}$ corresponds for each compound to a row of Table B Table 7

Compounds of the formula I.C in which Y is hydrogen, $R^1$ is methyl and the combination of the radicals X, $R^2$, $R^3$, $R^4$ and $R^a$ corresponds for each compound to a row of Table C

TABLE A

| No. | Y | $R^1$ | $R^2$ | $R^3$ | $R^4$ |
|---|---|---|---|---|---|
| A.1 | H | $CH_3$ | H | H | $CH_3$ |
| A.2 | H | $CH_3$ | H | H | ethyl |
| A.3 | H | $CH_3$ | H | H | n-propyl |
| A.4 | H | $CH_3$ | H | H | isopropyl |
| A.5 | H | $CH_3$ | H | H | tert-butyl |
| A.6 | H | $CH_3$ | H | H | n-butyl |
| A.7 | H | $CH_3$ | H | H | $C_6H_5$ |
| A.8 | H | $CH_3$ | H | H | 2-F—$C_6H_4$ |
| A.9 | H | $CH_3$ | H | H | 2-Cl—$C_6H_4$ |
| A.10 | H | $CH_3$ | H | H | 2-$CH_3$—$C_6H_4$ |
| A.11 | H | $CH_3$ | H | H | 2-$CF_3$—$C_6H_4$ |
| A.12 | H | $CH_3$ | H | H | 3-F—$C_6H_4$ |
| A.13 | H | $CH_3$ | H | H | 3-Cl—$C_6H_4$ |
| A.14 | H | $CH_3$ | H | H | 3-$CH_3$—$C_6H_4$ |
| A.15 | H | $CH_3$ | H | H | 3-$CF_3$—$C_6H_4$ |
| A.16 | H | $CH_3$ | H | H | 3-Br—$C_6H_4$ |
| A.17 | H | $CH_3$ | H | H | 4-F—$C_6H_4$ |
| A.18 | H | $CH_3$ | H | H | 4-Cl—$C_6H_4$ |
| A.19 | H | $CH_3$ | H | H | 4-$CH_3$—$C_6H_4$ |
| A.20 | H | $CH_3$ | H | H | 4-$CF_3$—$C_6H_4$ |
| A.21 | H | $CH_3$ | H | H | 4-$OCH_3$—$C_6H_4$ |
| A.22 | H | $CH_3$ | H | H | 4-$OCF_3$—$C_6H_4$ |
| A.23 | H | $CH_3$ | H | H | 4-Br—$C_6H_4$ |
| A.24 | H | $CH_3$ | H | H | 4-(CH=$NOCH_3$)—$C_6H_4$ |
| A.25 | H | $CH_3$ | H | H | 4-(CH=NOEt)—$C_6H_4$ |
| A.26 | H | $CH_3$ | H | H | 4-[C($CH_3$)=$NOCH_3$]—$C_6H_4$ |
| A.27 | H | $CH_3$ | H | H | 4-[C($CH_3$)=NOEt]—$C_6H_4$ |
| A.28 | H | $CH_3$ | H | H | 2,4-$F_2$—$C_6H_3$ |
| A.29 | H | $CH_3$ | H | H | 2,4-$Cl_2$—$C_6H_3$ |
| A.30 | H | $CH_3$ | H | H | 2,4-$(CH_3)_2$—$C_6H_3$ |
| A.31 | H | $CH_3$ | H | H | 3,5-$F_2$—$C_6H_3$ |
| A.32 | H | $CH_3$ | H | H | 3,5-$Cl_2$—$C_6H_3$ |
| A.33 | H | $CH_3$ | H | H | 3,5-$(CH_3)_2$—$C_6H_3$ |
| A.34 | H | $CH_3$ | H | H | 2-F-4-Cl—$C_6H_3$ |
| A.35 | H | $CH_3$ | H | H | 2-Cl-4-F—$C_6H_3$ |
| A.36 | H | $CH_3$ | H | H | 3,4-$F_2$—$C_6H_3$ |
| A.37 | H | $CH_3$ | H | H | 3,4-$Cl_2$—$C_6H_3$ |
| A.38 | H | $CH_3$ | H | H | 2,3-$F_2$—$C_6H_3$ |
| A.39 | H | $CH_3$ | H | $CH_3$ | $CH_3$ |
| A.40 | H | $CH_3$ | H | $CH_3$ | ethyl |
| A.41 | H | $CH_3$ | H | $CH_3$ | n-propyl |
| A.42 | H | $CH_3$ | H | $CH_3$ | isopropyl |
| A.43 | H | $CH_3$ | H | $CH_3$ | tert-butyl |
| A.44 | H | $CH_3$ | H | $CH_3$ | n-butyl |
| A.45 | H | $CH_3$ | H | $CH_3$ | $C_6H_5$ |
| A.46 | H | $CH_3$ | H | $CH_3$ | 2-F—$C_6H_4$ |
| A.47 | H | $CH_3$ | H | $CH_3$ | 2-Cl—$C_6H_4$ |
| A.48 | H | $CH_3$ | H | $CH_3$ | 2-$CH_3$—$C_6H_4$ |
| A.49 | H | $CH_3$ | H | $CH_3$ | 2-$CF_3$—$C_6H_4$ |
| A.50 | H | $CH_3$ | H | $CH_3$ | 3-F—$C_6H_4$ |
| A.51 | H | $CH_3$ | H | $CH_3$ | 3-Cl—$C_6H_4$ |
| A.52 | H | $CH_3$ | H | $CH_3$ | 3-$CH_3$—$C_6H_4$ |
| A.53 | H | $CH_3$ | H | $CH_3$ | 3-$CF_3$—$C_6H_4$ |
| A.54 | H | $CH_3$ | H | $CH_3$ | 3-Br—$C_6H_4$ |
| A.55 | H | $CH_3$ | H | $CH_3$ | 4-F—$C_6H_4$ |
| A.56 | H | $CH_3$ | H | $CH_3$ | 4-Cl—$C_6H_4$ |
| A.57 | H | $CH_3$ | H | $CH_3$ | 4-$CH_3$—$C_6H_4$ |
| A.58 | H | $CH_3$ | H | $CH_3$ | 4-$CF_3$—$C_6H_4$ |
| A.59 | H | $CH_3$ | H | $CH_3$ | 4-$OCH_3$—$C_6H_4$ |
| A.60 | H | $CH_3$ | H | $CH_3$ | 4-$OCF_3$—$C_6H_4$ |
| A.61 | H | $CH_3$ | H | $CH_3$ | 4-Br—$C_6H_4$ |
| A.62 | H | $CH_3$ | H | $CH_3$ | 4-(CH=$NOCH_3$)—$C_6H_4$ |
| A.63 | H | $CH_3$ | H | $CH_3$ | 4-(CH=NOEt)—$C_6H_4$ |
| A.64 | H | $CH_3$ | H | $CH_3$ | 4-[C($CH_3$)=$NOCH_3$]—$C_6H_4$ |
| A.65 | H | $CH_3$ | H | $CH_3$ | 4-[C($CH_3$)=NOEt]—$C_6H_4$ |
| A.66 | H | $CH_3$ | H | $CH_3$ | 2,4-$F_2$—$C_6H_3$ |
| A.67 | H | $CH_3$ | H | $CH_3$ | 2,4-$Cl_2$—$C_6H_3$ |

TABLE A-continued

| No. | Y | R¹ | R² | R³ | R⁴ |
|---|---|---|---|---|---|
| A.68 | H | $CH_3$ | H | $CH_3$ | 2,4-$(CH_3)_2$—$C_6H_3$ |
| A.69 | H | $CH_3$ | H | $CH_3$ | 3,5-$F_2$—$C_6H_3$ |
| A.70 | H | $CH_3$ | H | $CH_3$ | 3,5-$Cl_2$—$C_6H_3$ |
| A.71 | H | $CH_3$ | H | $CH_3$ | 3,5-$(CH_3)_2$—$C_6H_3$ |
| A.72 | H | $CH_3$ | H | $CH_3$ | 2-F-4-Cl—$C_6H_3$ |
| A.73 | H | $CH_3$ | H | $CH_3$ | 2-Cl-4-F—$C_6H_3$ |
| A.74 | H | $CH_3$ | H | $CH_3$ | 3,4-$F_2$—$C_6H_3$ |
| A.75 | H | $CH_3$ | H | $CH_3$ | 3,4-$Cl_2$—$C_6H_3$ |
| A.76 | H | $CH_3$ | H | $CH_3$ | 2,3-$F_2$—$C_6H_3$ |
| A.77 | H | $CH_3$ | H | ethyl | $CH_3$ |
| A.78 | H | $CH_3$ | H | ethyl | ethyl |
| A.79 | H | $CH_3$ | H | ethyl | n-propyl |
| A.80 | H | $CH_3$ | H | ethyl | isopropyl |
| A.81 | H | $CH_3$ | H | ethyl | tert-butyl |
| A.82 | H | $CH_3$ | H | ethyl | n-butyl |
| A.83 | H | $CH_3$ | H | ethyl | $C_6H_5$ |
| A.84 | H | $CH_3$ | H | ethyl | 2-F—$C_6H_4$ |
| A.85 | H | $CH_3$ | H | ethyl | 2-Cl—$C_6H_4$ |
| A.86 | H | $CH_3$ | H | ethyl | 2-$CH_3$—$C_6H_4$ |
| A.87 | H | $CH_3$ | H | ethyl | 2-$CF_3$—$C_6H_4$ |
| A.88 | H | $CH_3$ | H | ethyl | 3-F—$C_6H_4$ |
| A.89 | H | $CH_3$ | H | ethyl | 3-Cl—$C_6H_4$ |
| A.90 | H | $CH_3$ | H | ethyl | 3-$CH_3$—$C_6H_4$ |
| A.91 | H | $CH_3$ | H | ethyl | 3-$CF_3$—$C_6H_4$ |
| A.92 | H | $CH_3$ | H | ethyl | 3-Br—$C_6H_4$ |
| A.93 | H | $CH_3$ | H | ethyl | 4-F—$C_6H_4$ |
| A.94 | H | $CH_3$ | H | ethyl | 4-Cl—$C_6H_4$ |
| A.95 | H | $CH_3$ | H | ethyl | 4-$CH_3$—$C_6H_4$ |
| A.96 | H | $CH_3$ | H | ethyl | 4-$CF_3$—$C_6H_4$ |
| A.97 | H | $CH_3$ | H | ethyl | 4-$OCH_3$—$C_6H_4$ |
| A.98 | H | $CH_3$ | H | ethyl | 4-$OCF_3$—$C_6H_4$ |
| A.99 | H | $CH_3$ | H | ethyl | 4-Br—$C_6H_4$ |
| A.100 | H | $CH_3$ | H | ethyl | 4-(CH=$NOCH_3$)—$C_6H_4$ |
| A.101 | H | $CH_3$ | H | ethyl | 4-(CH=NOEt)—$C_6H_4$ |
| A.102 | H | $CH_3$ | H | ethyl | 4-[C($CH_3$)=$NOCH_3$]—$C_6H_4$ |
| A.103 | H | $CH_3$ | H | ethyl | 4-[C($CH_3$)=NOEt]—$C_6H_4$ |
| A.104 | H | $CH_3$ | H | ethyl | 2,4-$F_2$—$C_6H_3$ |
| A.105 | H | $CH_3$ | H | ethyl | 2,4-$Cl_2$—$C_6H_3$ |
| A.106 | H | $CH_3$ | H | ethyl | 2,4-$(CH_3)_2$—$C_6H_3$ |
| A.107 | H | $CH_3$ | H | ethyl | 3,5-$F_2$—$C_6H_3$ |
| A.108 | H | $CH_3$ | H | ethyl | 3,5-$Cl_2$—$C_6H_3$ |
| A.109 | H | $CH_3$ | H | ethyl | 3,5-$(CH_3)_2$—$C_6H_3$ |
| A.110 | H | $CH_3$ | H | ethyl | 2-F-4-Cl—$C_6H_3$ |
| A.111 | H | $CH_3$ | H | ethyl | 2-Cl-4-F—$C_6H_3$ |
| A.112 | H | $CH_3$ | H | ethyl | 3,4-$F_2$—$C_6H_3$ |
| A.113 | H | $CH_3$ | H | ethyl | 3,4-$Cl_2$—$C_6H_3$ |
| A.114 | H | $CH_3$ | H | ethyl | 2,3-$F_2$—$C_6H_3$ |
| A.115 | H | $CH_3$ | H | n-propyl | $CH_3$ |
| A.116 | H | $CH_3$ | H | n-propyl | ethyl |
| A.117 | H | $CH_3$ | H | n-propyl | n-propyl |
| A.118 | H | $CH_3$ | H | n-propyl | isopropyl |
| A.119 | H | $CH_3$ | H | n-propyl | tert-butyl |
| A.120 | H | $CH_3$ | H | n-propyl | n-butyl |
| A.121 | H | $CH_3$ | H | n-propyl | $C_6H_5$ |
| A.122 | H | $CH_3$ | H | n-propyl | 2-F—$C_6H_4$ |
| A.123 | H | $CH_3$ | H | n-propyl | 2-Cl—$C_6H_4$ |
| A.124 | H | $CH_3$ | H | n-propyl | 2-$CH_3$—$C_6H_4$ |
| A.125 | H | $CH_3$ | H | n-propyl | 2-$CF_3$—$C_6H_4$ |
| A.126 | H | $CH_3$ | H | n-propyl | 3-F—$C_6H_4$ |
| A.127 | H | $CH_3$ | H | n-propyl | 3-Cl—$C_6H_4$ |
| A.128 | H | $CH_3$ | H | n-propyl | 3-$CH_3$—$C_6H_4$ |
| A.129 | H | $CH_3$ | H | n-propyl | 3-$CF_3$—$C_6H_4$ |
| A.130 | H | $CH_3$ | H | n-propyl | 3-Br—$C_6H_4$ |
| A.131 | H | $CH_3$ | H | n-propyl | 4-F—$C_6H_4$ |
| A.132 | H | $CH_3$ | H | n-propyl | 4-Cl—$C_6H_4$ |
| A.133 | H | $CH_3$ | H | n-propyl | 4-$CH_3$—$C_6H_4$ |
| A.134 | H | $CH_3$ | H | n-propyl | 4-$CF_3$—$C_6H_4$ |
| A.135 | H | $CH_3$ | H | n-propyl | 4-$OCH_3$—$C_6H_4$ |
| A.136 | H | $CH_3$ | H | n-propyl | 4-$OCF_3$—$C_6H_4$ |
| A.137 | H | $CH_3$ | H | n-propyl | 4-Br—$C_6H_4$ |
| A.138 | H | $CH_3$ | H | n-propyl | 4-(CH=$NOCH_3$)—$C_6H_4$ |
| A.139 | H | $CH_3$ | H | n-propyl | 4-(CH=NOEt)—$C_6H_4$ |
| A.140 | H | $CH_3$ | H | n-propyl | 4-[C($CH_3$)=$NOCH_3$]—$C_6H_4$ |
| A.141 | H | $CH_3$ | H | n-propyl | 4-[C($CH_3$)=NOEt]—$C_6H_4$ |
| A.142 | H | $CH_3$ | H | n-propyl | 2,4-$F_2$—$C_6H_3$ |
| A.143 | H | $CH_3$ | H | n-propyl | 2,4-$Cl_2$—$C_6H_3$ |
| A.144 | H | $CH_3$ | H | n-propyl | 2,4-$(CH_3)_2$—$C_6H_3$ |

TABLE A-continued

| No. | Y | R¹ | R² | R³ | R⁴ |
|---|---|---|---|---|---|
| A.145 | H | CH₃ | H | n-propyl | 3,5-F₂—C₆H₃ |
| A.146 | H | CH₃ | H | n-propyl | 3,5-Cl₂—C₆H₃ |
| A.147 | H | CH₃ | H | n-propyl | 3,5-(CH₃)₂—C₆H₃ |
| A.148 | H | CH₃ | H | n-propyl | 2-F-4-Cl—C₆H₃ |
| A.149 | H | CH₃ | H | n-propyl | 2-Cl-4-F—C₆H₃ |
| A.150 | H | CH₃ | H | n-propyl | 3,4-F₂—C₆H₃ |
| A.151 | H | CH₃ | H | n-propyl | 3,4-Cl₂—C₆H₃ |
| A.152 | H | CH₃ | H | n-propyl | 2,3-F₂—C₆H₃ |
| A.153 | H | CH₃ | H | n-propyl | CH₃ |
| A.154 | H | CH₃ | H | n-propyl | ethyl |
| A.155 | H | CH₃ | H | n-propyl | n-propyl |
| A.156 | H | CH₃ | H | n-propyl | isopropyl |
| A.157 | H | CH₃ | H | n-propyl | tert-butyl |
| A.158 | H | CH₃ | H | n-propyl | n-butyl |
| A.159 | H | CH₃ | H | n-propyl | C₆H₅ |
| A.160 | H | CH₃ | H | n-propyl | 2-F—C₆H₄ |
| A.161 | H | CH₃ | H | n-propyl | 2-Cl—C₆H₄ |
| A.162 | H | CH₃ | H | n-propyl | 2-CH₃—C₆H₄ |
| A.163 | H | CH₃ | H | n-propyl | 2-CF₃—C₆H₄ |
| A.164 | H | CH₃ | H | n-propyl | 3-F—C₆H₄ |
| A.165 | H | CH₃ | H | n-propyl | 3-Cl—C₆H₄ |
| A.166 | H | CH₃ | H | n-propyl | 3-CH₃—C₆H₄ |
| A.167 | H | CH₃ | H | n-propyl | 3-CF₃—C₆H₄ |
| A.168 | H | CH₃ | H | n-propyl | 3-Br—C₆H₄ |
| A.169 | H | CH₃ | H | n-propyl | 4-F—C₆H₄ |
| A.170 | H | CH₃ | H | n-propyl | 4-Cl—C₆H₄ |
| A.171 | H | CH₃ | H | n-propyl | 4-CH₃—C₆H₄ |
| A.172 | H | CH₃ | H | n-propyl | 4-CF₃—C₆H₄ |
| A.173 | H | CH₃ | H | n-propyl | 4-OCH₃—C₆H₄ |
| A.174 | H | CH₃ | H | n-propyl | 4-OCF₃—C₆H₄ |
| A.175 | H | CH₃ | H | n-propyl | 4-Br—C₆H₄ |
| A.176 | H | CH₃ | H | n-propyl | 4-(CH=NOCH₃)—C₆H₄ |
| A.177 | H | CH₃ | H | n-propyl | 4-(CH=NOEt)—C₆H₄ |
| A.178 | H | CH₃ | H | n-propyl | 4-[C(CH₃)=NOCH₃]—C₆H₄ |
| A.179 | H | CH₃ | H | n-propyl | 4-[C(CH₃)=NOEt]—C₆H₄ |
| A.180 | H | CH₃ | H | n-propyl | 2,4-F₂—C₆H₃ |
| A.181 | H | CH₃ | H | n-propyl | 2,4-Cl₂—C₆H₃ |
| A.182 | H | CH₃ | H | n-propyl | 2,4-(CH₃)₂—C₆H₃ |
| A.183 | H | CH₃ | H | n-propyl | 3,5-F₂—C₆H₃ |
| A.184 | H | CH₃ | H | n-propyl | 3,5-Cl₂—C₆H₃ |
| A.185 | H | CH₃ | H | n-propyl | 3,5-(CH₃)₂—C₆H₃ |
| A.186 | H | CH₃ | H | n-propyl | 2-F-4-Cl—C₆H₃ |
| A.187 | H | CH₃ | H | n-propyl | 2-Cl-4-F—C₆H₃ |
| A.188 | H | CH₃ | H | n-propyl | 3,4-F₂—C₆H₃ |
| A.189 | H | CH₃ | H | n-propyl | 3,4-Cl₂—C₆H₃ |
| A.190 | H | CH₃ | H | n-propyl | 2,3-F₂—C₆H₃ |
| A.191 | H | CH₃ | H | n-butyl | CH₃ |
| A.192 | H | CH₃ | H | n-butyl | ethyl |
| A.193 | H | CH₃ | H | n-butyl | n-propyl |
| A.194 | H | CH₃ | H | n-butyl | isopropyl |
| A.195 | H | CH₃ | H | n-butyl | tert-butyl |
| A.196 | H | CH₃ | H | n-butyl | n-butyl |
| A.197 | H | CH₃ | H | n-butyl | C₆H₅ |
| A.198 | H | CH₃ | H | n-butyl | 2-F—C₆H₄ |
| A.199 | H | CH₃ | H | n-butyl | 2-Cl—C₆H₄ |
| A.200 | H | CH₃ | H | n-butyl | 2-CH₃—C₆H₄ |
| A.201 | H | CH₃ | H | n-butyl | 2-CF₃—C₆H₄ |
| A.202 | H | CH₃ | H | n-butyl | 3-F—C₆H₄ |
| A.203 | H | CH₃ | H | n-butyl | 3-Cl—C₆H₄ |
| A.204 | H | CH₃ | H | n-butyl | 3-CH₃—C₆H₄ |
| A.205 | H | CH₃ | H | n-butyl | 3-CF₃—C₆H₄ |
| A.206 | H | CH₃ | H | n-butyl | 3-Br—C₆H₄ |
| A.207 | H | CH₃ | H | n-butyl | 4-F—C₆H₄ |
| A.208 | H | CH₃ | H | n-butyl | 4-Cl—C₆H₄ |
| A.209 | H | CH₃ | H | n-butyl | 4-CH₃—C₆H₄ |
| A.210 | H | CH₃ | H | n-butyl | 4-CF₃—C₆H₄ |
| A.211 | H | CH₃ | H | n-butyl | 4-OCH₃—C₆H₄ |
| A.212 | H | CH₃ | H | n-butyl | 4-OCF₃—C₆H₄ |
| A.213 | H | CH₃ | H | n-butyl | 4-Br—C₆H₄ |
| A.214 | H | CH₃ | H | n-butyl | 4-(CH=NOCH₃)—C₆H₄ |
| A.215 | H | CH₃ | H | n-butyl | 4-(CH=NOEt)—C₆H₄ |
| A.216 | H | CH₃ | H | n-butyl | 4-[C(CH₃)=NOCH₃]—C₆H₄ |
| A.217 | H | CH₃ | H | n-butyl | 4-[C(CH₃)=NOEt]—C₆H₄ |
| A.218 | H | CH₃ | H | n-butyl | 2,4-F₂—C₆H₃ |
| A.219 | H | CH₃ | H | n-butyl | 2,4-Cl₂—C₆H₃ |
| A.220 | H | CH₃ | H | n-butyl | 2,4-(CH₃)₂—C₆H₃ |
| A.221 | H | CH₃ | H | n-butyl | 3,5-F₂—C₆H₃ |

TABLE A-continued

| No. | Y | R$^1$ | R$^2$ | R$^3$ | R$^4$ |
|---|---|---|---|---|---|
| A.222 | H | CH$_3$ | H | n-butyl | 3,5-Cl$_2$—C$_6$H$_3$ |
| A.223 | H | CH$_3$ | H | n-butyl | 3,5-(CH$_3$)$_2$—C$_6$H$_3$ |
| A.224 | H | CH$_3$ | H | n-butyl | 2-F-4-Cl—C$_6$H$_3$ |
| A.225 | H | CH$_3$ | H | n-butyl | 2-Cl-4-F—C$_6$H$_3$ |
| A.226 | H | CH$_3$ | H | n-butyl | 3,4-F$_2$—C$_6$H$_3$ |
| A.227 | H | CH$_3$ | H | n-butyl | 3,4-Cl$_2$—C$_6$H$_3$ |
| A.228 | H | CH$_3$ | H | n-butyl | 2,3-F$_2$—C$_6$H$_3$ |
| A.229 | H | CH$_3$ | H | n-butyl | CH$_3$ |
| A.230 | H | CH$_3$ | H | n-butyl | ethyl |
| A.231 | H | CH$_3$ | H | n-butyl | n-propyl |
| A.232 | H | CH$_3$ | H | n-butyl | isopropyl |
| A.233 | H | CH$_3$ | H | n-butyl | tert-butyl |
| A.234 | H | CH$_3$ | H | n-butyl | n-butyl |
| A.235 | H | CH$_3$ | H | n-butyl | C$_6$H$_5$ |
| A.236 | H | CH$_3$ | H | n-butyl | 2-F—C$_6$H$_4$ |
| A.237 | H | CH$_3$ | H | n-butyl | 2-Cl—C$_6$H$_4$ |
| A.238 | H | CH$_3$ | H | n-butyl | 2-CH$_3$—C$_6$H$_4$ |
| A.239 | H | CH$_3$ | H | n-butyl | 2-CF$_3$—C$_6$H$_4$ |
| A.240 | H | CH$_3$ | H | n-butyl | 3-F—C$_6$H$_4$ |
| A.241 | H | CH$_3$ | H | n-butyl | 3-Cl—C$_6$H$_4$ |
| A.242 | H | CH$_3$ | H | n-butyl | 3-CH$_3$—C$_6$H$_4$ |
| A.243 | H | CH$_3$ | H | n-butyl | 3-CF$_3$—C$_6$H$_4$ |
| A.244 | H | CH$_3$ | H | n-butyl | 3-Br—C$_6$H$_4$ |
| A.245 | H | CH$_3$ | H | n-butyl | 4-F—C$_6$H$_4$ |
| A.246 | H | CH$_3$ | H | n-butyl | 4-Cl—C$_6$H$_4$ |
| A.247 | H | CH$_3$ | H | n-butyl | 4-CH$_3$—C$_6$H$_4$ |
| A.248 | H | CH$_3$ | H | n-butyl | 4-CF$_3$—C$_6$H$_4$ |
| A.249 | H | CH$_3$ | H | n-butyl | 4-OCH$_3$—C$_6$H$_4$ |
| A.250 | H | CH$_3$ | H | n-butyl | 4-OCF$_3$—C$_6$H$_4$ |
| A.251 | H | CH$_3$ | H | n-butyl | 4-Br—C$_6$H$_4$ |
| A.252 | H | CH$_3$ | H | n-butyl | 4-(CH=NOCH$_3$)—C$_6$H$_4$ |
| A.253 | H | CH$_3$ | H | n-butyl | 4-(CH=NOEt)—C$_6$H$_4$ |
| A.254 | H | CH$_3$ | H | n-butyl | 4-[C(CH$_3$)=NOCH$_3$]—C$_6$H$_4$ |
| A.255 | H | CH$_3$ | H | n-butyl | 4-[C(CH$_3$)=NOEt]—C$_6$H$_4$ |
| A.256 | H | CH$_3$ | H | n-butyl | 2,4-F$_2$—C$_6$H$_3$ |
| A.257 | H | CH$_3$ | H | n-butyl | 2,4-Cl$_2$—C$_6$H$_3$ |
| A.258 | H | CH$_3$ | H | n-butyl | 2,4-(CH$_3$)$_2$—C$_6$H$_3$ |
| A.259 | H | CH$_3$ | H | n-butyl | 3,5-F$_2$—C$_6$H$_3$ |
| A.260 | H | CH$_3$ | H | n-butyl | 3,5-Cl$_2$—C$_6$H$_3$ |
| A.261 | H | CH$_3$ | H | n-butyl | 3,5-(CH$_3$)$_2$—C$_6$H$_3$ |
| A.262 | H | CH$_3$ | H | n-butyl | 2-F-4-Cl—C$_6$H$_3$ |
| A.263 | H | CH$_3$ | H | n-butyl | 2-Cl-4-F—C$_6$H$_3$ |
| A.264 | H | CH$_3$ | H | n-butyl | 3,4-F$_2$—C$_6$H$_3$ |
| A.265 | H | CH$_3$ | H | n-butyl | 3,4-Cl$_2$—C$_6$H$_3$ |
| A.266 | H | CH$_3$ | H | n-butyl | 2,3-F$_2$—C$_6$H$_3$ |
| A.267 | H | CH$_3$ | H | isopropyl | CH$_3$ |
| A.268 | H | CH$_3$ | H | isopropyl | ethyl |
| A.269 | H | CH$_3$ | H | isopropyl | n-propyl |
| A.270 | H | CH$_3$ | H | isopropyl | isopropyl |
| A.271 | H | CH$_3$ | H | isopropyl | tert-butyl |
| A.272 | H | CH$_3$ | H | isopropyl | n-butyl |
| A.273 | H | CH$_3$ | H | isopropyl | C$_6$H$_5$ |
| A.274 | H | CH$_3$ | H | isopropyl | 2-F—C$_6$H$_4$ |
| A.275 | H | CH$_3$ | H | isopropyl | 2-Cl—C$_6$H$_4$ |
| A.276 | H | CH$_3$ | H | isopropyl | 2-CH$_3$—C$_6$H$_4$ |
| A.277 | H | CH$_3$ | H | isopropyl | 2-CF$_3$—C$_6$H$_4$ |
| A.278 | H | CH$_3$ | H | isopropyl | 3-F—C$_6$H$_4$ |
| A.279 | H | CH$_3$ | H | isopropyl | 3-Cl—C$_6$H$_4$ |
| A.280 | H | CH$_3$ | H | isopropyl | 3-CH$_3$—C$_6$H$_4$ |
| A.281 | H | CH$_3$ | H | isopropyl | 3-CF$_3$—C$_6$H$_4$ |
| A.282 | H | CH$_3$ | H | isopropyl | 3-Br—C$_6$H$_4$ |
| A.283 | H | CH$_3$ | H | isopropyl | 4-F—C$_6$H$_4$ |
| A.284 | H | CH$_3$ | H | isopropyl | 4-Cl—C$_6$H$_4$ |
| A.285 | H | CH$_3$ | H | isopropyl | 4-CH$_3$—C$_6$H$_4$ |
| A.286 | H | CH$_3$ | H | isopropyl | 4-CF$_3$—C$_6$H$_4$ |
| A.287 | H | CH$_3$ | H | isopropyl | 4-OCH$_3$—C$_6$H$_4$ |
| A.288 | H | CH$_3$ | H | isopropyl | 4-OCF$_3$—C$_6$H$_4$ |
| A.289 | H | CH$_3$ | H | isopropyl | 4-Br—C$_6$H$_4$ |
| A.290 | H | CH$_3$ | H | isopropyl | 4-(CH=NOCH$_3$)—C$_6$H$_4$ |
| A.291 | H | CH$_3$ | H | isopropyl | 4-(CH=NOEt)—C$_6$H$_4$ |
| A.292 | H | CH$_3$ | H | isopropyl | 4-[C(CH$_3$)=NOCH$_3$]—C$_6$H$_4$ |
| A.293 | H | CH$_3$ | H | isopropyl | 4-[C(CH$_3$)=NOEt]—C$_6$H$_4$ |
| A.294 | H | CH$_3$ | H | isopropyl | 2,4-F$_2$—C$_6$H$_3$ |
| A.295 | H | CH$_3$ | H | isopropyl | 2,4-Cl$_2$—C$_6$H$_3$ |
| A.296 | H | CH$_3$ | H | isopropyl | 2,4-(CH$_3$)$_2$—C$_6$H$_3$ |
| A.297 | H | CH$_3$ | H | isopropyl | 3,5-F$_2$—C$_6$H$_3$ |
| A.298 | H | CH$_3$ | H | isopropyl | 3,5-Cl$_2$—C$_6$H$_3$ |

TABLE A-continued

| No. | Y | R¹ | R² | R³ | R⁴ |
|---|---|---|---|---|---|
| A.299 | H | $CH_3$ | H | isopropyl | 3,5-$(CH_3)_2$—$C_6H_3$ |
| A.300 | H | $CH_3$ | H | isopropyl | 2-F-4-Cl—$C_6H_3$ |
| A.301 | H | $CH_3$ | H | isopropyl | 2-Cl-4-F—$C_6H_3$ |
| A.303 | H | $CH_3$ | H | isopropyl | 3,4-$F_2$—$C_6H_3$ |
| A.302 | H | $CH_3$ | H | isopropyl | 3,4-$Cl_2$—$C_6H_3$ |
| A.304 | H | $CH_3$ | H | isopropyl | 2,3-$F_2$—$C_6H_3$ |
| A.305 | H | $CH_3$ | H | isopropyl | $CH_3$ |
| A.306 | H | $CH_3$ | H | isopropyl | ethyl |
| A.307 | H | $CH_3$ | H | isopropyl | n-propyl |
| A.308 | H | $CH_3$ | H | isopropyl | isopropyl |
| A.309 | H | $CH_3$ | H | isopropyl | tert-butyl |
| A.310 | H | $CH_3$ | H | isopropyl | n-butyl |
| A.311 | H | $CH_3$ | H | isopropyl | $C_6H_5$ |
| A.312 | H | $CH_3$ | H | isopropyl | 2-F—$C_6H_4$ |
| A.313 | H | $CH_3$ | H | isopropyl | 2-Cl—$C_6H_4$ |
| A.314 | H | $CH_3$ | H | isopropyl | 2-$CH_3$—$C_6H_4$ |
| A.315 | H | $CH_3$ | H | isopropyl | 2-$CF_3$—$C_6H_4$ |
| A.316 | H | $CH_3$ | H | isopropyl | 3-F—$C_6H_4$ |
| A.317 | H | $CH_3$ | H | isopropyl | 3-Cl—$C_6H_4$ |
| A.318 | H | $CH_3$ | H | isopropyl | 3-$CH_3$—$C_6H_4$ |
| A.319 | H | $CH_3$ | H | isopropyl | 3-$CF_3$—$C_6H_4$ |
| A.320 | H | $CH_3$ | H | isopropyl | 3-Br—$C_6H_4$ |
| A.321 | H | $CH_3$ | H | isopropyl | 4-F—$C_6H_4$ |
| A.322 | H | $CH_3$ | H | isopropyl | 4-Cl—$C_6H_4$ |
| A.323 | H | $CH_3$ | H | isopropyl | 4-$CH_3$—$C_6H_4$ |
| A.324 | H | $CH_3$ | H | isopropyl | 4-$CF_3$—$C_6H_4$ |
| A.325 | H | $CH_3$ | H | isopropyl | 4-$OCH_3$—$C_6H_4$ |
| A.326 | H | $CH_3$ | H | isopropyl | 4-$OCF_3$—$C_6H_4$ |
| A.327 | H | $CH_3$ | H | isopropyl | 4-Br—$C_6H_4$ |
| A.328 | H | $CH_3$ | H | isopropyl | 4-(CH=$NOCH_3$)—$C_6H_4$ |
| A.329 | H | $CH_3$ | H | isopropyl | 4-(CH=NOEt)—$C_6H_4$ |
| A.330 | H | $CH_3$ | H | isopropyl | 4-[C($CH_3$)=$NOCH_3$]—$C_6H_4$ |
| A.231 | H | $CH_3$ | H | isopropyl | 4-[C($CH_3$)=NOEt]—$C_6H_4$ |
| A.332 | H | $CH_3$ | H | isopropyl | 2,4-$F_2$—$C_6H_3$ |
| A.333 | H | $CH_3$ | H | isopropyl | 2,4-$Cl_2$—$C_6H_3$ |
| A.334 | H | $CH_3$ | H | isopropyl | 2,4-$(CH_3)_2$—$C_6H_3$ |
| A.335 | H | $CH_3$ | H | isopropyl | 3,5-$F_2$—$C_6H_3$ |
| A.336 | H | $CH_3$ | H | isopropyl | 3,5-$Cl_2$—$C_6H_3$ |
| A.337 | H | $CH_3$ | H | isopropyl | 3,5-$(CH_3)_2$—$C_6H_3$ |
| A.338 | H | $CH_3$ | H | isopropyl | 2-F-4-Cl—$C_6H_3$ |
| A.339 | H | $CH_3$ | H | isopropyl | 2-Cl-4-F—$C_6H_3$ |
| A.340 | H | $CH_3$ | H | isopropyl | 3,4-$F_2$—$C_6H_3$ |
| A.341 | H | $CH_3$ | H | isopropyl | 3,4-$Cl_2$—$C_6H_3$ |
| A.342 | H | $CH_3$ | H | isopropyl | 2,3-$F_2$—$C_6H_3$ |
| A.343 | H | $CH_3$ | H | tert-butyl | $CH_3$ |
| A.344 | H | $CH_3$ | H | tert-butyl | ethyl |
| A.345 | H | $CH_3$ | H | tert-butyl | n-propyl |
| A.346 | H | $CH_3$ | H | tert-butyl | isopropyl |
| A.347 | H | $CH_3$ | H | tert-butyl | tert-butyl |
| A.348 | H | $CH_3$ | H | tert-butyl | n-butyl |
| A.349 | H | $CH_3$ | H | tert-butyl | $C_6H_5$ |
| A.350 | H | $CH_3$ | H | tert-butyl | 2-F—$C_6H_4$ |
| A.351 | H | $CH_3$ | H | tert-butyl | 2-Cl—$C_6H_4$ |
| A.352 | H | $CH_3$ | H | tert-butyl | 2-$CH_3$—$C_6H_4$ |
| A.353 | H | $CH_3$ | H | tert-butyl | 2-$CF_3$—$C_6H_4$ |
| A.354 | H | $CH_3$ | H | tert-butyl | 3-F—$C_6H_4$ |
| A.355 | H | $CH_3$ | H | tert-butyl | 3-Cl—$C_6H_4$ |
| A.356 | H | $CH_3$ | H | tert-butyl | 3-$CH_3$—$C_6H_4$ |
| A.357 | H | $CH_3$ | H | tert-butyl | 3-$CF_3$—$C_6H_4$ |
| A.358 | H | $CH_3$ | H | tert-butyl | 3-Br—$C_6H_4$ |
| A.359 | H | $CH_3$ | H | tert-butyl | 4-F—$C_6H_4$ |
| A.360 | H | $CH_3$ | H | tert-butyl | 4-Cl—$C_6H_4$ |
| A.361 | H | $CH_3$ | H | tert-butyl | 4-$CH_3$—$C_6H_4$ |
| A.362 | H | $CH_3$ | H | tert-butyl | 4-$CF_3$—$C_6H_4$ |
| A.363 | H | $CH_3$ | H | tert-butyl | 4-$OCH_3$—$C_6H_4$ |
| A.364 | H | $CH_3$ | H | tert-butyl | 4-$OCF_3$—$C_6H_4$ |
| A.365 | H | $CH_3$ | H | tert-butyl | 4-Br—$C_6H_4$ |
| A.366 | H | $CH_3$ | H | tert-butyl | 4-(CH=$NOCH_3$)—$C_6H_4$ |
| A.367 | H | $CH_3$ | H | tert-butyl | 4-(CH=NOEt)—$C_6H_4$ |
| A.368 | H | $CH_3$ | H | tert-butyl | 4-[C($CH_3$)=$NOCH_3$]—$C_6H_4$ |
| A.369 | H | $CH_3$ | H | tert-butyl | 4-[C($CH_3$)=NOEt]—$C_6H_4$ |
| A.370 | H | $CH_3$ | H | tert-butyl | 2,4-$F_2$—$C_6H_3$ |
| A.371 | H | $CH_3$ | H | tert-butyl | 2,4-$Cl_2$—$C_6H_3$ |
| A.372 | H | $CH_3$ | H | tert-butyl | 2,4-$(CH_3)_2$—$C_6H_3$ |
| A.373 | H | $CH_3$ | H | tert-butyl | 3,5-$F_2$—$C_6H_3$ |
| A.374 | H | $CH_3$ | H | tert-butyl | 3,5-$Cl_2$—$C_6H_3$ |
| A.375 | H | $CH_3$ | H | tert-butyl | 3,5-$(CH_3)_2$—$C_6H_3$ |

TABLE A-continued

| No. | Y | R¹ | R² | R³ | R⁴ |
|---|---|---|---|---|---|
| A.376 | H | CH₃ | H | tert-butyl | 2-F-4-Cl—C₆H₃ |
| A.377 | H | CH₃ | H | tert-butyl | 2-Cl-4-F—C₆H₃ |
| A.378 | H | CH₃ | H | tert-butyl | 3,4-F₂—C₆H₃ |
| A.379 | H | CH₃ | H | tert-butyl | 3,4-Cl₂—C₆H₃ |
| A.380 | H | CH₃ | H | tert-butyl | 2,3-F₂—C₆H₃ |
| A.381 | H | CH₃ | H | tert-butyl | CH₃ |
| A.382 | H | CH₃ | H | tert-butyl | ethyl |
| A.383 | H | CH₃ | H | tert-butyl | n-propyl |
| A.384 | H | CH₃ | H | tert-butyl | isopropyl |
| A.385 | H | CH₃ | H | tert-butyl | tert-butyl |
| A.386 | H | CH₃ | H | tert-butyl | n-butyl |
| A.387 | H | CH₃ | H | tert-butyl | C₆H₅ |
| A.388 | H | CH₃ | H | tert-butyl | 2-F—C₆H₄ |
| A.389 | H | CH₃ | H | tert-butyl | 2-Cl—C₆H₄ |
| A.390 | H | CH₃ | H | tert-butyl | 2-CH₃—C₆H₄ |
| A.391 | H | CH₃ | H | tert-butyl | 2-CF₃—C₆H₄ |
| A.392 | H | CH₃ | H | tert-butyl | 3-F—C₆H₄ |
| A.393 | H | CH₃ | H | tert-butyl | 3-Cl—C₆H₄ |
| A.394 | H | CH₃ | H | tert-butyl | 3-CH₃—C₆H₄ |
| A.395 | H | CH₃ | H | tert-butyl | 3-CF₃—C₆H₄ |
| A.396 | H | CH₃ | H | tert-butyl | 3-Br—C₆H₄ |
| A.397 | H | CH₃ | H | tert-butyl | 4-F—C₆H₄ |
| A.398 | H | CH₃ | H | tert-butyl | 4-Cl—C₆H₄ |
| A.399 | H | CH₃ | H | tert-butyl | 4-CH₃—C₆H₄ |
| A.400 | H | CH₃ | H | tert-butyl | 4-CF₃—C₆H₄ |
| A.401 | H | CH₃ | H | tert-butyl | 4-OCH₃—C₆H₄ |
| A.402 | H | CH₃ | H | tert-butyl | 4-OCF₃—C₆H₄ |
| A.403 | H | CH₃ | H | tert-butyl | 4-Br—C₆H₄ |
| A.404 | H | CH₃ | H | tert-butyl | 4-(CH=NOCH₃)—C₆H₄ |
| A.405 | H | CH₃ | H | tert-butyl | 4-(CH=NOEt)—C₆H₄ |
| A.406 | H | CH₃ | H | tert-butyl | 4-[C(CH₃)=NOCH₃]—C₆H₄ |
| A.407 | H | CH₃ | H | tert-butyl | 4-[C(CH₃)=NOEt]—C₆H₄ |
| A.408 | H | CH₃ | H | tert-butyl | 2,4-F₂—C₆H₃ |
| A.409 | H | CH₃ | H | tert-butyl | 2,4-Cl₂—C₆H₃ |
| A.410 | H | CH₃ | H | tert-butyl | 2,4-(CH₃)₂—C₆H₃ |
| A.411 | H | CH₃ | H | tert-butyl | 3,5-F₂—C₆H₃ |
| A.412 | H | CH₃ | H | tert-butyl | 3,5-Cl₂—C₆H₃ |
| A.413 | H | CH₃ | H | tert-butyl | 3,5-(CH₃)₂—C₆H₃ |
| A.414 | H | CH₃ | H | tert-butyl | 2-F-4-Cl—C₆H₃ |
| A.415 | H | CH₃ | H | tert-butyl | 2-Cl-4-F—C₆H₃ |
| A.416 | H | CH₃ | H | tert-butyl | 3,4-F₂—C₆H₃ |
| A.417 | H | CH₃ | H | tert-butyl | 3,4-Cl₂—C₆H₃ |
| A.418 | H | CH₃ | H | tert-butyl | 2,3-F₂—C₆H₃ |
| A.419 | H | Cl | CH₃ | CH₃ | C₆H₅ |
| A.420 | H | Cl | CH₃ | CH₃ | 4-F—C₆H₄ |
| A.421 | H | Cl | CH₃ | CH₃ | 4-Cl—C₆H₄ |
| A.422 | H | Cl | CH₃ | CH₃ | CH₃ |
| A.423 | H | CF₃ | CH₃ | CH₃ | C₆H₅ |
| A.424 | H | CF₃ | CH₃ | CH₃ | 4-F—C₆H₄ |
| A.425 | H | CF₃ | CH₃ | CH₃ | 4-Cl—C₆H₄ |
| A.426 | H | CF₃ | CH₃ | CH₃ | CH₃ |
| A.427 | H | OCH₃ | CH₃ | CH₃ | C₆H₅ |
| A.428 | H | OCH₃ | CH₃ | CH₃ | 4-F—C₆H₄ |
| A.429 | H | OCH₃ | CH₃ | CH₃ | 4-Cl—C₆H₄ |
| A.430 | H | OCH₃ | CH₃ | CH₃ | CH₃ |
| A.431 | 6-CH₃ | CH₃ | H | CH₃ | CH₃ |
| A.432 | 6-CH₃ | CH₃ | H | CH₃ | C₆H₅ |
| A.433 | 6-CH₃ | CH₃ | H | CH₃ | 4-F—C₆H₄ |
| A.434 | 6-CH₃ | CH₃ | H | CH₃ | 4-Cl—C₆H₄ |
| A.435 | 6-CH₃ | CH₃ | H | ethyl | CH₃ |
| A.436 | 6-CH₃ | CH₃ | H | ethyl | C₆H₅ |
| A.437 | 6-CH₃ | CH₃ | H | ethyl | 4-F—C₆H₄ |
| A.438 | 6-CH₃ | CH₃ | H | ethyl | 4-Cl—C₆H₄ |
| A.439 | 6-CH₃ | CH₃ | H | n-propyl | CH₃ |
| A.440 | 6-CH₃ | CH₃ | H | n-propyl | C₆H₅ |
| A.441 | 6-CH₃ | CH₃ | H | n-propyl | 4-F—C₆H₄ |
| A.442 | 6-CH₃ | CH₃ | H | n-propyl | 4-Cl—C₆H₄ |
| A.443 | 6-CH₃ | CH₃ | H | n-butyl | CH₃ |
| A.444 | 6-CH₃ | CH₃ | H | n-butyl | C₆H₅ |
| A.445 | 6-CH₃ | CH₃ | H | n-butyl | 4-F—C₆H₄ |
| A.446 | 6-CH₃ | CH₃ | H | n-butyl | 4-Cl—C₆H₄ |
| A.447 | 6-CH₃ | ethyl | H | CH₃ | CH₃ |
| A.448 | 6-CH₃ | ethyl | H | CH₃ | C₆H₅ |
| A.449 | 6-CH₃ | ethyl | H | CH₃ | 4-F—C₆H₄ |
| A.450 | 6-CH₃ | ethyl | H | CH₃ | 4-Cl—C₆H₄ |
| A.451 | 6-CH₃ | ethyl | H | ethyl | CH₃ |
| A.452 | 6-CH₃ | ethyl | H | ethyl | C₆H₅ |

TABLE A-continued

| No. | Y | R¹ | R² | R³ | R⁴ |
|---|---|---|---|---|---|
| A.453 | 6-CH₃ | ethyl | H | ethyl | 4-F—C₆H₄ |
| A.454 | 6-CH₃ | ethyl | H | ethyl | 4-Cl—C₆H₄ |
| A.455 | 6-CH₃ | ethyl | H | n-propyl | CH₃ |
| A.456 | 6-CH₃ | ethyl | H | n-propyl | C₆H₅ |
| A.457 | 6-CH₃ | ethyl | H | n-propyl | 4-F—C₆H₄ |
| A.458 | 6-CH₃ | ethyl | H | n-propyl | 4-Cl—C₆H₄ |
| A.459 | 6-CH₃ | ethyl | H | n-butyl | CH₃ |
| A.460 | 6-CH₃ | ethyl | H | n-butyl | C₆H₅ |
| A.461 | 6-CH₃ | ethyl | H | n-butyl | 4-F—C₆H₄ |
| A.462 | 6-CH₃ | ethyl | H | n-butyl | 4-Cl—C₆H₄ |
| A.463 | 6-Cl | CH₃ | H | CH₃ | CH₃ |
| A.464 | 6-Cl | CH₃ | H | CH₃ | C₆H₅ |
| A.465 | 6-Cl | CH₃ | H | CH₃ | 4-F—C₆H₄ |
| A.466 | 6-Cl | CH₃ | H | CH₃ | 4-Cl—C₆H₄ |
| A.467 | 6-Cl | CH₃ | H | ethyl | CH₃ |
| A.468 | 6-Cl | CH₃ | H | ethyl | C₆H₅ |
| A.469 | 6-Cl | CH₃ | H | ethyl | 4-F—C₆H₄ |
| A.470 | 6-Cl | CH₃ | H | ethyl | 4-Cl—C₆H₄ |
| A.471 | 6-Cl | CH₃ | H | n-propyl | CH₃ |
| A.472 | 6-Cl | CH₃ | H | n-propyl | C₆H₅ |
| A.473 | 6-Cl | CH₃ | H | n-propyl | 4-F—C₆H₄ |
| A.474 | 6-Cl | CH₃ | H | n-propyl | 4-Cl—C₆H₄ |
| A.475 | 6-Cl | CH₃ | H | n-butyl | CH₃ |
| A.476 | 6-Cl | CH₃ | H | n-butyl | C₆H₅ |
| A.477 | 6-Cl | CH₃ | H | n-butyl | 4-F—C₆H₄ |
| A.478 | 6-Cl | CH₃ | H | n-butyl | 4-Cl—C₆H₄ |
| A.479 | 6-Cl | ethyl | H | CH₃ | CH₃ |
| A.480 | 6-Cl | ethyl | H | CH₃ | C₆H₅ |
| A.481 | 6-Cl | ethyl | H | CH₃ | 4-F—C₆H₄ |
| A.482 | 6-Cl | ethyl | H | CH₃ | 4-Cl—C₆H₄ |
| A.483 | 6-Cl | ethyl | H | ethyl | CH₃ |
| A.484 | 6-Cl | ethyl | H | ethyl | C₆H₅ |
| A.485 | 6-Cl | ethyl | H | ethyl | 4-F—C₆H₄ |
| A.486 | 6-Cl | ethyl | H | ethyl | 4-Cl—C₆H₄ |
| A.487 | 6-Cl | ethyl | H | n-propyl | CH₃ |
| A.488 | 6-Cl | ethyl | H | n-propyl | C₆H₅ |
| A.489 | 6-Cl | ethyl | H | n-propyl | 4-F—C₆H₄ |
| A.490 | 6-Cl | ethyl | H | n-propyl | 4-Cl—C₆H₄ |
| A.491 | 6-Cl | ethyl | H | n-butyl | CH₃ |
| A.492 | 6-Cl | ethyl | H | n-butyl | C₆H₅ |
| A.493 | 6-Cl | ethyl | H | n-butyl | 4-F—C₆H₄ |
| A.494 | 6-Cl | ethyl | H | n-butyl | 4-Cl—C₆H₄ |
| A.495 | 6-F | CH₃ | H | CH₃ | CH₃ |
| A.496 | 6-F | CH₃ | H | CH₃ | C₆H₅ |
| A.497 | 6-F | CH₃ | H | CH₃ | 4-F—C₆H₄ |
| A.498 | 6-F | CH₃ | H | CH₃ | 4-Cl—C₆H₄ |
| A.499 | 6-F | CH₃ | H | ethyl | CH₃ |
| A.500 | 6-F | CH₃ | H | ethyl | C₆H₅ |
| A.501 | 6-F | CH₃ | H | ethyl | 4-F—C₆H₄ |
| A.502 | 6-F | CH₃ | H | ethyl | 4-Cl—C₆H₄ |
| A.503 | 6-F | CH₃ | H | n-propyl | CH₃ |
| A.504 | 6-F | CH₃ | H | n-propyl | C₆H₅ |
| A.505 | 6-F | CH₃ | H | n-propyl | 4-F—C₆H₄ |
| A.506 | 6-F | CH₃ | H | n-propyl | 4-Cl—C₆H₄ |
| A.507 | 6-F | CH₃ | H | n-butyl | CH₃ |
| A.508 | 6-F | CH₃ | H | n-butyl | C₆H₅ |
| A.509 | 6-F | CH₃ | H | n-butyl | 4-F—C₆H₄ |
| A.510 | 6-F | CH₃ | H | n-butyl | 4-Cl—C₆H₄ |
| A.511 | 6-F | ethyl | H | CH₃ | CH₃ |
| A.512 | 6-F | ethyl | H | CH₃ | C₆H₅ |
| A.513 | 6-F | ethyl | H | CH₃ | 4-F—C₆H₄ |
| A.514 | 6-F | ethyl | H | CH₃ | 4-Cl—C₆H₄ |
| A.515 | 6-F | ethyl | H | ethyl | CH₃ |
| A.516 | 6-F | ethyl | H | ethyl | C₆H₅ |
| A.517 | 6-F | ethyl | H | ethyl | 4-F—C₆H₄ |
| A.518 | 6-F | ethyl | H | ethyl | 4-Cl—C₆H₄ |
| A.519 | 6-F | ethyl | H | n-propyl | CH₃ |
| A.520 | 6-F | ethyl | H | n-propyl | C₆H₅ |
| A.521 | 6-F | ethyl | H | n-propyl | 4-F—C₆H₄ |
| A.522 | 6-F | ethyl | H | n-propyl | 4-Cl—C₆H₄ |
| A.523 | 6-F | ethyl | H | n-butyl | CH₃ |
| A.524 | 6-F | ethyl | H | n-butyl | C₆H₅ |
| A.525 | 6-F | ethyl | H | n-butyl | 4-F—C₆H₄ |
| A.526 | 6-F | ethyl | H | n-butyl | 4-Cl—C₆H₄ |
| A.527 | 3-F | CH₃ | H | CH₃ | CH₃ |
| A.528 | 3-F | CH₃ | H | CH₃ | C₆H₅ |
| A.529 | 3-F | CH₃ | H | CH₃ | 4-F—C₆H₄ |

TABLE A-continued

| No. | Y | R¹ | R² | R³ | R⁴ |
|---|---|---|---|---|---|
| A.530 | 3-F | CH₃ | H | CH₃ | 4-Cl—C₆H₄ |
| A.531 | 3-F | CH₃ | H | ethyl | CH₃ |
| A.532 | 3-F | CH₃ | H | ethyl | C₆H₅ |
| A.533 | 3-F | CH₃ | H | ethyl | 4-F—C₆H₄ |
| A.534 | 3-F | CH₃ | H | ethyl | 4-Cl—C₆H₄ |
| A.535 | 3-F | CH₃ | H | n-propyl | CH₃ |
| A.536 | 3-F | CH₃ | H | n-propyl | C₆H₅ |
| A.537 | 3-F | CH₃ | H | n-propyl | 4-F—C₆H₄ |
| A.538 | 3-F | CH₃ | H | n-propyl | 4-Cl—C₆H₄ |
| A.539 | 3-F | CH₃ | H | n-butyl | CH₃ |
| A.540 | 3-F | CH₃ | H | n-butyl | C₆H₅ |
| A.541 | 3-F | CH₃ | H | n-butyl | 4-F—C₆H₄ |
| A.542 | 3-F | CH₃ | H | n-butyl | 4-Cl—C₆H₄ |
| A.543 | 3-F | ethyl | H | CH₃ | CH₃ |
| A.544 | 3-F | ethyl | H | CH₃ | C₆H₅ |
| A.545 | 3-F | ethyl | H | CH₃ | 4-F—C₆H₄ |
| A.546 | 3-F | ethyl | H | CH₃ | 4-Cl—C₆H₄ |
| A.547 | 3-F | ethyl | H | ethyl | CH₃ |
| A.548 | 3-F | ethyl | H | ethyl | C₆H₅ |
| A.549 | 3-F | ethyl | H | ethyl | 4-F—C₆H₄ |
| A.550 | 3-F | ethyl | H | ethyl | 4-Cl—C₆H₄ |
| A.551 | 3-F | ethyl | H | n-propyl | CH₃ |
| A.552 | 3-F | ethyl | H | n-propyl | C₆H₅ |
| A.553 | 3-F | ethyl | H | n-propyl | 4-F—C₆H₄ |
| A.554 | 3-F | ethyl | H | n-propyl | 4-Cl—C₆H₄ |
| A.555 | 3-F | ethyl | H | n-butyl | CH₃ |
| A.556 | 3-F | ethyl | H | n-butyl | C₆H₅ |
| A.557 | 3-F | ethyl | H | n-butyl | 4-F—C₆H₄ |
| A.558 | 3-F | ethyl | H | n-butyl | 4-Cl—C₆H₄ |
| A.559 | H | ethyl | H | H | CH₃ |
| A.560 | H | ethyl | H | H | ethyl |
| A.561 | H | ethyl | H | H | n-propyl |
| A.562 | H | ethyl | H | H | isopropyl |
| A.563 | H | ethyl | H | H | tert-butyl |
| A.564 | H | ethyl | H | H | n-butyl |
| A.565 | H | ethyl | H | H | C₆H₅ |
| A.566 | H | ethyl | H | H | 2-F—C₆H₄ |
| A.567 | H | ethyl | H | H | 2-Cl—C₆H₄ |
| A.568 | H | ethyl | H | H | 2-CH₃—C₆H₄ |
| A.569 | H | ethyl | H | H | 2-CF₃—C₆H₄ |
| A.570 | H | ethyl | H | H | 3-F—C₆H₄ |
| A.571 | H | ethyl | H | H | 3-Cl—C₆H₄ |
| A.572 | H | ethyl | H | H | 3-CH₃—C₆H₄ |
| A.573 | H | ethyl | H | H | 3-CF₃—C₆H₄ |
| A.574 | H | ethyl | H | H | 3-Br—C₆H₄ |
| A.575 | H | ethyl | H | H | 4-F—C₆H₄ |
| A.576 | H | ethyl | H | H | 4-Cl—C₆H₄ |
| A.577 | H | ethyl | H | H | 4-CH₃—C₆H₄ |
| A.578 | H | ethyl | H | H | 4-CF₃—C₆H₄ |
| A.579 | H | ethyl | H | H | 4-OCH₃—C₆H₄ |
| A.580 | H | ethyl | H | H | 4-OCF₃—C₆H₄ |
| A.581 | H | ethyl | H | H | 4-Br—C₆H₄ |
| A.582 | H | ethyl | H | H | 4-(CH═NOCH₃)—C₆H₄ |
| A.583 | H | ethyl | H | H | 4-(CH═NOEt)—C₆H₄ |
| A.584 | H | ethyl | H | H | 4-[C(CH₃)═NOCH₃]—C₆H₄ |
| A.585 | H | ethyl | H | H | 4-[C(CH₃)═NOEt]—C₆H₄ |
| A.586 | H | ethyl | H | H | 2,4-F₂—C₆H₃ |
| A.587 | H | ethyl | H | H | 2,4-Cl₂—C₆H₃ |
| A.588 | H | ethyl | H | H | 2,4-(CH₃)₂—C₆H₃ |
| A.589 | H | ethyl | H | H | 3,5-F₂—C₆H₃ |
| A.590 | H | ethyl | H | H | 3,5-Cl₂—C₆H₃ |
| A.591 | H | ethyl | H | H | 3,5-(CH₃)₂—C₆H₃ |
| A.592 | H | ethyl | H | H | 2-F-4-Cl—C₆H₃ |
| A.593 | H | ethyl | H | H | 2-Cl-4-F—C₆H₃ |
| A.594 | H | ethyl | H | H | 3,4-F₂—C₆H₃ |
| A.595 | H | ethyl | H | H | 3,4-Cl₂—C₆H₃ |
| A.596 | H | ethyl | H | H | 2,3-F₂—C₆H₃ |
| A.597 | H | ethyl | H | CH₃ | CH₃ |
| A.598 | H | ethyl | H | CH₃ | ethyl |
| A.599 | H | ethyl | H | CH₃ | n-propyl |
| A.600 | H | ethyl | H | CH₃ | isopropyl |
| A.601 | H | ethyl | H | CH₃ | tert-butyl |
| A.602 | H | ethyl | H | CH₃ | n-butyl |
| A.603 | H | ethyl | H | CH₃ | C₆H₅ |
| A.604 | H | ethyl | H | CH₃ | 2-F—C₆H₄ |
| A.605 | H | ethyl | H | CH₃ | 2-Cl—C₆H₄ |
| A.606 | H | ethyl | H | CH₃ | 2-CH₃—C₆H₄ |

TABLE A-continued

| No. | Y | R¹ | R² | R³ | R⁴ |
|---|---|---|---|---|---|
| A.607 | H | ethyl | H | CH₃ | 2-CF₃—C₆H₄ |
| A.608 | H | ethyl | H | CH₃ | 3-F—C₆H₄ |
| A.609 | H | ethyl | H | CH₃ | 3-Cl—C₆H₄ |
| A.610 | H | ethyl | H | CH₃ | 3-CH₃—C₆H₄ |
| A.611 | H | ethyl | H | CH₃ | 3-CF₃—C₆H₄ |
| A.612 | H | ethyl | H | CH₃ | 3-Br—C₆H₄ |
| A.613 | H | ethyl | H | CH₃ | 4-F—C₆H₄ |
| A.614 | H | ethyl | H | CH₃ | 4-Cl—C₆H₄ |
| A.615 | H | ethyl | H | CH₃ | 4-CH₃—C₆H₄ |
| A.616 | H | ethyl | H | CH₃ | 4-CF₃—C₆H₄ |
| A.617 | H | ethyl | H | CH₃ | 4-OCH₃—C₆H₄ |
| A.618 | H | ethyl | H | CH₃ | 4-OCF₃—C₆H₄ |
| A.619 | H | ethyl | H | CH₃ | 4-Br—C₆H₄ |
| A.620 | H | ethyl | H | CH₃ | 4-(CH=NOCH₃)—C₆H₄ |
| A.621 | H | ethyl | H | CH₃ | 4-(CH=NOEt)—C₆H₄ |
| A.622 | H | ethyl | H | CH₃ | 4-[C(CH₃)=NOCH₃]—C₆H₄ |
| A.623 | H | ethyl | H | CH₃ | 4-[C(CH₃)=NOEt]—C₆H₄ |
| A.624 | H | ethyl | H | CH₃ | 2,4-F₂—C₆H₃ |
| A.625 | H | ethyl | H | CH₃ | 2,4-Cl₂—C₆H₃ |
| A.626 | H | ethyl | H | CH₃ | 2,4-(CH₃)₂—C₆H₃ |
| A.627 | H | ethyl | H | CH₃ | 3,5-F₂—C₆H₃ |
| A.628 | H | ethyl | H | CH₃ | 3,5-Cl₂—C₆H₃ |
| A.629 | H | ethyl | H | CH₃ | 3,5-(CH₃)₂—C₆H₃ |
| A.630 | H | ethyl | H | CH₃ | 2-F-4-Cl—C₆H₃ |
| A.631 | H | ethyl | H | CH₃ | 2-Cl-4-F—C₆H₃ |
| A.632 | H | ethyl | H | CH₃ | 3,4-F₂—C₆H₃ |
| A.633 | H | ethyl | H | CH₃ | 3,4-Cl₂—C₆H₃ |
| A.634 | H | ethyl | H | CH₃ | 2,3-F₂—C₆H₃ |
| A.635 | H | ethyl | H | ethyl | CH₃ |
| A.636 | H | ethyl | H | ethyl | ethyl |
| A.637 | H | ethyl | H | ethyl | n-propyl |
| A.638 | H | ethyl | H | ethyl | isopropyl |
| A.639 | H | ethyl | H | ethyl | tert-butyl |
| A.640 | H | ethyl | H | ethyl | n-butyl |
| A.641 | H | ethyl | H | ethyl | C₆H₅ |
| A.642 | H | ethyl | H | ethyl | 2-F—C₆H₄ |
| A.643 | H | ethyl | H | ethyl | 2-Cl—C₆H₄ |
| A.644 | H | ethyl | H | ethyl | 2-CH₃—C₆H₄ |
| A.645 | H | ethyl | H | ethyl | 2-CF₃—C₆H₄ |
| A.646 | H | ethyl | H | ethyl | 3-F—C₆H₄ |
| A.647 | H | ethyl | H | ethyl | 3-Cl—C₆H₄ |
| A.648 | H | ethyl | H | ethyl | 3-CH₃—C₆H₄ |
| A.649 | H | ethyl | H | ethyl | 3-CF₃—C₆H₄ |
| A.650 | H | ethyl | H | ethyl | 3-Br—C₆H₄ |
| A.651 | H | ethyl | H | ethyl | 4-F—C₆H₄ |
| A.652 | H | ethyl | H | ethyl | 4-Cl—C₆H₄ |
| A.653 | H | ethyl | H | ethyl | 4-CH₃—C₆H₄ |
| A.654 | H | ethyl | H | ethyl | 4-CF₃—C₆H₄ |
| A.655 | H | ethyl | H | ethyl | 4-OCH₃—C₆H₄ |
| A.656 | H | ethyl | H | ethyl | 4-OCF₃—C₆H₄ |
| A.657 | H | ethyl | H | ethyl | 4-Br—C₆H₄ |
| A.658 | H | ethyl | H | ethyl | 4-(CH=NOCH₃)—C₆H₄ |
| A.659 | H | ethyl | H | ethyl | 4-(CH=NOEt)—C₆H₄ |
| A.660 | H | ethyl | H | ethyl | 4-[C(CH₃)=NOCH₃]—C₆H₄ |
| A.661 | H | ethyl | H | ethyl | 4-[C(CH₃)=NOEt]—C₆H₄ |
| A.662 | H | ethyl | H | ethyl | 2,4-F₂—C₆H₃ |
| A.663 | H | ethyl | H | ethyl | 2,4-Cl₂—C₆H₃ |
| A.664 | H | ethyl | H | ethyl | 2,4-(CH₃)₂—C₆H₃ |
| A.665 | H | ethyl | H | ethyl | 3,5-F₂—C₆H₃ |
| A.666 | H | ethyl | H | ethyl | 3,5-Cl₂—C₆H₃ |
| A.667 | H | ethyl | H | ethyl | 3,5-(CH₃)₂—C₆H₃ |
| A.668 | H | ethyl | H | ethyl | 2-F-4-Cl—C₆H₃ |
| A.669 | H | ethyl | H | ethyl | 2-Cl-4-F—C₆H₃ |
| A.670 | H | ethyl | H | ethyl | 3,4-F₂—C₆H₃ |
| A.671 | H | ethyl | H | ethyl | 3,4-Cl₂—C₆H₃ |
| A.672 | H | ethyl | H | ethyl | 2,3-F₂—C₆H₃ |
| A.673 | H | ethyl | H | n-propyl | CH₃ |
| A.674 | H | ethyl | H | n-propyl | ethyl |
| A.675 | H | ethyl | H | n-propyl | n-propyl |
| A.676 | H | ethyl | H | n-propyl | isopropyl |
| A.677 | H | ethyl | H | n-propyl | tert-butyl |
| A.678 | H | ethyl | H | n-propyl | n-butyl |
| A.679 | H | ethyl | H | n-propyl | C₆H₅ |
| A.680 | H | ethyl | H | n-propyl | 2-F—C₆H₄ |
| A.681 | H | ethyl | H | n-propyl | 2-Cl—C₆H₄ |
| A.682 | H | ethyl | H | n-propyl | 2-CH₃—C₆H₄ |
| A.683 | H | ethyl | H | n-propyl | 2-CF₃—C₆H₄ |

TABLE A-continued

| No. | Y | $R^1$ | $R^2$ | $R^3$ | $R^4$ |
|---|---|---|---|---|---|
| A.684 | H | ethyl | H | n-propyl | 3-F—$C_6H_4$ |
| A.685 | H | ethyl | H | n-propyl | 3-Cl—$C_6H_4$ |
| A.686 | H | ethyl | H | n-propyl | 3-$CH_3$—$C_6H_4$ |
| A.687 | H | ethyl | H | n-propyl | 3-$CF_3$—$C_6H_4$ |
| A.688 | H | ethyl | H | n-propyl | 3-Br—$C_6H_4$ |
| A.689 | H | ethyl | H | n-propyl | 4-F—$C_6H_4$ |
| A.690 | H | ethyl | H | n-propyl | 4-Cl—$C_6H_4$ |
| A.691 | H | ethyl | H | n-propyl | 4-$CH_3$—$C_6H_4$ |
| A.692 | H | ethyl | H | n-propyl | 4-$CF_3$—$C_6H_4$ |
| A.693 | H | ethyl | H | n-propyl | 4-$OCH_3$—$C_6H_4$ |
| A.694 | H | ethyl | H | n-propyl | 4-$OCF_3$—$C_6H_4$ |
| A.695 | H | ethyl | H | n-propyl | 4-Br—$C_6H_4$ |
| A.696 | H | ethyl | H | n-propyl | 4-(CH=$NOCH_3$)—$C_6H_4$ |
| A.697 | H | ethyl | H | n-propyl | 4-(CH=NOEt)—$C_6H_4$ |
| A.698 | H | ethyl | H | n-propyl | 4-[C($CH_3$)=$NOCH_3$]—$C_6H_4$ |
| A.699 | H | ethyl | H | n-propyl | 4-[C($CH_3$)=NOEt]—$C_6H_4$ |
| A.700 | H | ethyl | H | n-propyl | 2,4-$F_2$—$C_6H_3$ |
| A.701 | H | ethyl | H | n-propyl | 2,4-$Cl_2$—$C_6H_3$ |
| A.702 | H | ethyl | H | n-propyl | 2,4-$(CH_3)_2$—$C_6H_3$ |
| A.703 | H | ethyl | H | n-propyl | 3,5-$F_2$—$C_6H_3$ |
| A.704 | H | ethyl | H | n-propyl | 3,5-$Cl_2$—$C_6H_3$ |
| A.705 | H | ethyl | H | n-propyl | 3,5-$(CH_3)_2$—$C_6H_3$ |
| A.706 | H | ethyl | H | n-propyl | 2-F-4-Cl—$C_6H_3$ |
| A.707 | H | ethyl | H | n-propyl | 2-Cl-4-F—$C_6H_3$ |
| A.708 | H | ethyl | H | n-propyl | 3,4-$F_2$—$C_6H_3$ |
| A.709 | H | ethyl | H | n-propyl | 3,4-$Cl_2$—$C_6H_3$ |
| A.710 | H | ethyl | H | n-propyl | 2,3-$F_2$—$C_6H_3$ |
| A.711 | H | ethyl | H | n-propyl | $CH_3$ |
| A.712 | H | ethyl | H | n-propyl | ethyl |
| A.713 | H | ethyl | H | n-propyl | n-propyl |
| A.714 | H | ethyl | H | n-propyl | isopropyl |
| A.715 | H | ethyl | H | n-propyl | tert-butyl |
| A.716 | H | ethyl | H | n-propyl | n-butyl |
| A.717 | H | ethyl | H | n-propyl | $C_6H_5$ |
| A.718 | H | ethyl | H | n-propyl | 2-F—$C_6H_4$ |
| A.719 | H | ethyl | H | n-propyl | 2-Cl—$C_6H_4$ |
| A.720 | H | ethyl | H | n-propyl | 2-$CH_3$—$C_6H_4$ |
| A.721 | H | ethyl | H | n-propyl | 2-$CF_3$—$C_6H_4$ |
| A.722 | H | ethyl | H | n-propyl | 3-F—$C_6H_4$ |
| A.723 | H | ethyl | H | n-propyl | 3-Cl—$C_6H_4$ |
| A.724 | H | ethyl | H | n-propyl | 3-$CH_3$—$C_6H_4$ |
| A.725 | H | ethyl | H | n-propyl | 3-$CF_3$—$C_6H_4$ |
| A.726 | H | ethyl | H | n-propyl | 3-Br—$C_6H_4$ |
| A.727 | H | ethyl | H | n-propyl | 4-F—$C_6H_4$ |
| A.728 | H | ethyl | H | n-propyl | 4-Cl—$C_6H_4$ |
| A.729 | H | ethyl | H | n-propyl | 4-$CH_3$—$C_6H_4$ |
| A.730 | H | ethyl | H | n-propyl | 4-$CF_3$—$C_6H_4$ |
| A.731 | H | ethyl | H | n-propyl | 4-$OCH_3$—$C_6H_4$ |
| A.732 | H | ethyl | H | n-propyl | 4-$OCF_3$—$C_6H_4$ |
| A.733 | H | ethyl | H | n-propyl | 4-Br—$C_6H_4$ |
| A.734 | H | ethyl | H | n-propyl | 4-(CH=$NOCH_3$)—$C_6H_4$ |
| A.735 | H | ethyl | H | n-propyl | 4-(CH=NOEt)—$C_6H_4$ |
| A.736 | H | ethyl | H | n-propyl | 4-[C($CH_3$)=$NOCH_3$]—$C_6H_4$ |
| A.737 | H | ethyl | H | n-propyl | 4-[C($CH_3$)=NOEt]—$C_6H_4$ |
| A.738 | H | ethyl | H | n-propyl | 2,4-$F_2$—$C_6H_3$ |
| A.739 | H | ethyl | H | n-propyl | 2,4-$Cl_2$—$C_6H_3$ |
| A.740 | H | ethyl | H | n-propyl | 2,4-$(CH_3)_2$—$C_6H_3$ |
| A.741 | H | ethyl | H | n-propyl | 3,5-$F_2$—$C_6H_3$ |
| A.742 | H | ethyl | H | n-propyl | 3,5-$Cl_2$—$C_6H_3$ |
| A.743 | H | ethyl | H | n-propyl | 3,5-$(CH_3)_2$—$C_6H_3$ |
| A.744 | H | ethyl | H | n-propyl | 2-F-4-Cl—$C_6H_3$ |
| A.745 | H | ethyl | H | n-propyl | 2-Cl-4-F—$C_6H_3$ |
| A.746 | H | ethyl | H | n-propyl | 3,4-$F_2$—$C_6H_3$ |
| A.747 | H | ethyl | H | n-propyl | 3,4-$Cl_2$—$C_6H_3$ |
| A.748 | H | ethyl | H | n-propyl | 2,3-$F_2$—$C_6H_3$ |
| A.749 | H | ethyl | H | n-butyl | $CH_3$ |
| A.750 | H | ethyl | H | n-butyl | ethyl |
| A.751 | H | ethyl | H | n-butyl | n-propyl |
| A.752 | H | ethyl | H | n-butyl | isopropyl |
| A.753 | H | ethyl | H | n-butyl | tert-butyl |
| A.754 | H | ethyl | H | n-butyl | n-butyl |
| A.755 | H | ethyl | H | n-butyl | $C_6H_5$ |
| A.756 | H | ethyl | H | n-butyl | 2-F—$C_6H_4$ |
| A.757 | H | ethyl | H | n-butyl | 2-Cl—$C_6H_4$ |
| A.758 | H | ethyl | H | n-butyl | 2-$CH_3$—$C_6H_4$ |
| A.759 | H | ethyl | H | n-butyl | 2-$CF_3$—$C_6H_4$ |
| A.760 | H | ethyl | H | n-butyl | 3-F—$C_6H_4$ |

TABLE A-continued

| No. | Y | R¹ | R² | R³ | R⁴ |
|---|---|---|---|---|---|
| A.761 | H | ethyl | H | n-butyl | 3-Cl—C₆H₄ |
| A.762 | H | ethyl | H | n-butyl | 3-CH₃—C₆H₄ |
| A.763 | H | ethyl | H | n-butyl | 3-CF₃—C₆H₄ |
| A.764 | H | ethyl | H | n-butyl | 3-Br—C₆H₄ |
| A.765 | H | ethyl | H | n-butyl | 4-F—C₆H₄ |
| A.766 | H | ethyl | H | n-butyl | 4-Cl—C₆H₄ |
| A.767 | H | ethyl | H | n-butyl | 4-CH₃—C₆H₄ |
| A.768 | H | ethyl | H | n-butyl | 4-CF₃—C₆H₄ |
| A.769 | H | ethyl | H | n-butyl | 4-OCH₃—C₆H₄ |
| A.770 | H | ethyl | H | n-butyl | 4-OCF₃—C₆H₄ |
| A.771 | H | ethyl | H | n-butyl | 4-Br—C₆H₄ |
| A.772 | H | ethyl | H | n-butyl | 4-(CH=NOCH₃)—C₆H₄ |
| A.773 | H | ethyl | H | n-butyl | 4-(CH=NOEt)—C₆H₄ |
| A.774 | H | ethyl | H | n-butyl | 4-[C(CH₃)=NOCH₃]—C₆H₄ |
| A.775 | H | ethyl | H | n-butyl | 4-[C(CH₃)=NOEt]—C₆H₄ |
| A.776 | H | ethyl | H | n-butyl | 2,4-F₂—C₆H₃ |
| A.777 | H | ethyl | H | n-butyl | 2,4-Cl₂—C₆H₃ |
| A.778 | H | ethyl | H | n-butyl | 2,4-(CH₃)₂—C₆H₃ |
| A.779 | H | ethyl | H | n-butyl | 3,5-F₂—C₆H₃ |
| A.780 | H | ethyl | H | n-butyl | 3,5-Cl₂—C₆H₃ |
| A.781 | H | ethyl | H | n-butyl | 3,5-(CH₃)₂—C₆H₃ |
| A.782 | H | ethyl | H | n-butyl | 2-F-4-Cl—C₆H₃ |
| A.783 | H | ethyl | H | n-butyl | 2-Cl-4-F—C₆H₃ |
| A.784 | H | ethyl | H | n-butyl | 3,4-F₂—C₆H₃ |
| A.785 | H | ethyl | H | n-butyl | 3,4-Cl₂—C₆H₃ |
| A.786 | H | ethyl | H | n-butyl | 2,3-F₂—C₆H₃ |
| A.787 | H | ethyl | H | n-butyl | CH₃ |
| A.788 | H | ethyl | H | n-butyl | ethyl |
| A.789 | H | ethyl | H | n-butyl | n-propyl |
| A.790 | H | ethyl | H | n-butyl | isopropyl |
| A.791 | H | ethyl | H | n-butyl | tert-butyl |
| A.792 | H | ethyl | H | n-butyl | n-butyl |
| A.793 | H | ethyl | H | n-butyl | C₆H₅ |
| A.794 | H | ethyl | H | n-butyl | 2-F—C₆H₄ |
| A.795 | H | ethyl | H | n-butyl | 2-Cl—C₆H₄ |
| A.796 | H | ethyl | H | n-butyl | 2-CH₃—C₆H₄ |
| A.797 | H | ethyl | H | n-butyl | 2-CF₃—C₆H₄ |
| A.798 | H | ethyl | H | n-butyl | 3-F—C₆H₄ |
| A.799 | H | ethyl | H | n-butyl | 3-Cl—C₆H₄ |
| A.800 | H | ethyl | H | n-butyl | 3-CH₃—C₆H₄ |
| A.801 | H | ethyl | H | n-butyl | 3-CF₃—C₆H₄ |
| A.802 | H | ethyl | H | n-butyl | 3-Br—C₆H₄ |
| A.803 | H | ethyl | H | n-butyl | 4-F—C₆H₄ |
| A.804 | H | ethyl | H | n-butyl | 4-Cl—C₆H₄ |
| A.805 | H | ethyl | H | n-butyl | 4-CH₃—C₆H₄ |
| A.806 | H | ethyl | H | n-butyl | 4-CF₃—C₆H₄ |
| A.807 | H | ethyl | H | n-butyl | 4-OCH₃—C₆H₄ |
| A.808 | H | ethyl | H | n-butyl | 4-OCF₃—C₆H₄ |
| A.809 | H | ethyl | H | n-butyl | 4-Br—C₆H₄ |
| A.810 | H | ethyl | H | n-butyl | 4-(CH=NOCH₃)—C₆H₄ |
| A.811 | H | ethyl | H | n-butyl | 4-(CH=NOEt)—C₆H₄ |
| A.812 | H | ethyl | H | n-butyl | 4-[C(CH₃)=NOCH₃]—C₆H₄ |
| A.813 | H | ethyl | H | n-butyl | 4-[C(CH₃)=NOEt]—C₆H₄ |
| A.814 | H | ethyl | H | n-butyl | 2,4-F₂—C₆H₃ |
| A.815 | H | ethyl | H | n-butyl | 2,4-Cl₂—C₆H₃ |
| A.816 | H | ethyl | H | n-butyl | 2,4-(CH₃)₂—C₆H₃ |
| A.817 | H | ethyl | H | n-butyl | 3,5-F₂—C₆H₃ |
| A.818 | H | ethyl | H | n-butyl | 3,5-Cl₂—C₆H₃ |
| A.819 | H | ethyl | H | n-butyl | 3,5-(CH₃)₂—C₆H₃ |
| A.820 | H | ethyl | H | n-butyl | 2-F-4-Cl—C₆H₃ |
| A.821 | H | ethyl | H | n-butyl | 2-Cl-4-F—C₆H₃ |
| A.822 | H | ethyl | H | n-butyl | 3,4-F₂—C₆H₃ |
| A.823 | H | ethyl | H | n-butyl | 3,4-Cl₂—C₆H₃ |
| A.824 | H | ethyl | H | n-butyl | 2,3-F₂—C₆H₃ |
| A.825 | H | ethyl | H | isopropyl | CH₃ |
| A.826 | H | ethyl | H | isopropyl | ethyl |
| A.827 | H | ethyl | H | isopropyl | n-propyl |
| A.828 | H | ethyl | H | isopropyl | isopropyl |
| A.829 | H | ethyl | H | isopropyl | tert-butyl |
| A.830 | H | ethyl | H | isopropyl | n-butyl |
| A.831 | H | ethyl | H | isopropyl | C₆H₅ |
| A.832 | H | ethyl | H | isopropyl | 2-F—C₆H₄ |
| A.833 | H | ethyl | H | isopropyl | 2-Cl—C₆H₄ |
| A.834 | H | ethyl | H | isopropyl | 2-CH₃—C₆H₄ |
| A.835 | H | ethyl | H | isopropyl | 2-CF₃—C₆H₄ |
| A.836 | H | ethyl | H | isopropyl | 3-F—C₆H₄ |
| A.837 | H | ethyl | H | isopropyl | 3-Cl—C₆H₄ |

TABLE A-continued

| No. | Y | R¹ | R² | R³ | R⁴ |
|---|---|---|---|---|---|
| A.838 | H | ethyl | H | isopropyl | 3-CH₃—C₆H₄ |
| A.839 | H | ethyl | H | isopropyl | 3-CF₃—C₆H₄ |
| A.840 | H | ethyl | H | isopropyl | 3-Br—C₆H₄ |
| A.841 | H | ethyl | H | isopropyl | 4-F—C₆H₄ |
| A.842 | H | ethyl | H | isopropyl | 4-Cl—C₆H₄ |
| A.843 | H | ethyl | H | isopropyl | 4-CH₃—C₆H₄ |
| A.844 | H | ethyl | H | isopropyl | 4-CF₃—C₆H₄ |
| A.845 | H | ethyl | H | isopropyl | 4-OCH₃—C₆H₄ |
| A.846 | H | ethyl | H | isopropyl | 4-OCF₃—C₆H₄ |
| A.847 | H | ethyl | H | isopropyl | 4-Br—C₆H₄ |
| A.848 | H | ethyl | H | isopropyl | 4-(CH=NOCH₃)—C₆H₄ |
| A.849 | H | ethyl | H | isopropyl | 4-(CH=NOEt)—C₆H₄ |
| A.850 | H | ethyl | H | isopropyl | 4-[C(CH₃)=NOCH₃]—C₆H₄ |
| A.851 | H | ethyl | H | isopropyl | 4-[C(CH₃)=NOEt]—C₆H₄ |
| A.852 | H | ethyl | H | isopropyl | 2,4-F₂—C₆H₃ |
| A.853 | H | ethyl | H | isopropyl | 2,4-Cl₂—C₆H₃ |
| A.854 | H | ethyl | H | isopropyl | 2,4-(CH₃)₂—C₆H₃ |
| A.855 | H | ethyl | H | isopropyl | 3,5-F₂—C₆H₃ |
| A.856 | H | ethyl | H | isopropyl | 3,5-Cl₂—C₆H₃ |
| A.857 | H | ethyl | H | isopropyl | 3,5-(CH₃)₂—C₆H₃ |
| A.858 | H | ethyl | H | isopropyl | 2-F-4-Cl—C₆H₃ |
| A.859 | H | ethyl | H | isopropyl | 2-Cl-4-F—C₆H₃ |
| A.860 | H | ethyl | H | isopropyl | 3,4-F₂—C₆H₃ |
| A.861 | H | ethyl | H | isopropyl | 3,4-Cl₂—C₆H₃ |
| A.862 | H | ethyl | H | isopropyl | 2,3-F₂—C₆H₃ |
| A.863 | H | ethyl | H | isopropyl | CH₃ |
| A.864 | H | ethyl | H | isopropyl | ethyl |
| A.865 | H | ethyl | H | isopropyl | n-propyl |
| A.866 | H | ethyl | H | isopropyl | isopropyl |
| A.867 | H | ethyl | H | isopropyl | tert-butyl |
| A.868 | H | ethyl | H | isopropyl | n-butyl |
| A.869 | H | ethyl | H | isopropyl | C₆H₅ |
| A.870 | H | ethyl | H | isopropyl | 2-F—C₆H₄ |
| A.871 | H | ethyl | H | isopropyl | 2-Cl—C₆H₄ |
| A.872 | H | ethyl | H | isopropyl | 2-CH₃—C₆H₄ |
| A.873 | H | ethyl | H | isopropyl | 2-CF₃—C₆H₄ |
| A.874 | H | ethyl | H | isopropyl | 3-F—C₆H₄ |
| A.875 | H | ethyl | H | isopropyl | 3-Cl—C₆H₄ |
| A.876 | H | ethyl | H | isopropyl | 3-CH₃—C₆H₄ |
| A.877 | H | ethyl | H | isopropyl | 3-CF₃—C₆H₄ |
| A.878 | H | ethyl | H | isopropyl | 3-Br—C₆H₄ |
| A.879 | H | ethyl | H | isopropyl | 4-F—C₆H₄ |
| A.880 | H | ethyl | H | isopropyl | 4-Cl—C₆H₄ |
| A.881 | H | ethyl | H | isopropyl | 4-CH₃—C₆H₄ |
| A.882 | H | ethyl | H | isopropyl | 4-CF₃—C₆H₄ |
| A.883 | H | ethyl | H | isopropyl | 4-OCH₃—C₆H₄ |
| A.884 | H | ethyl | H | isopropyl | 4-OCF₃—C₆H₄ |
| A.885 | H | ethyl | H | isopropyl | 4-Br—C₆H₄ |
| A.886 | H | ethyl | H | isopropyl | 4-(CH=NOCH₃)—C₆H₄ |
| A.887 | H | ethyl | H | isopropyl | 4-(CH=NOEt)—C₆H₄ |
| A.888 | H | ethyl | H | isopropyl | 4-[C(CH₃)=NOCH₃]—C₆H₄ |
| A.889 | H | ethyl | H | isopropyl | 4-[C(CH₃)=NOEt]—C₆H₄ |
| A.890 | H | ethyl | H | isopropyl | 2,4-F₂—C₆H₃ |
| A.891 | H | ethyl | H | isopropyl | 2,4-Cl₂—C₆H₃ |
| A.892 | H | ethyl | H | isopropyl | 2,4-(CH₃)₂—C₆H₃ |
| A.893 | H | ethyl | H | isopropyl | 3,5-F₂—C₆H₃ |
| A.894 | H | ethyl | H | isopropyl | 3,5-Cl₂—C₆H₃ |
| A.895 | H | ethyl | H | isopropyl | 3,5-(CH₃)₂—C₆H₃ |
| A.896 | H | ethyl | H | isopropyl | 2-F-4-Cl—C₆H₃ |
| A.897 | H | ethyl | H | isopropyl | 2-Cl-4-F—C₆H₃ |
| A.898 | H | ethyl | H | isopropyl | 3,4-F₂—C₆H₃ |
| A.899 | H | ethyl | H | isopropyl | 3,4-Cl₂—C₆H₃ |
| A.900 | H | ethyl | H | isopropyl | 2,3-F₂—C₆H₃ |
| A.901 | H | ethyl | H | tert-butyl | CH₃ |
| A.902 | H | ethyl | H | tert-butyl | ethyl |
| A.903 | H | ethyl | H | tert-butyl | n-propyl |
| A.904 | H | ethyl | H | tert-butyl | isopropyl |
| A.905 | H | ethyl | H | tert-butyl | tert-butyl |
| A.906 | H | ethyl | H | tert-butyl | n-butyl |
| A.907 | H | ethyl | H | tert-butyl | C₆H₅ |
| A.908 | H | ethyl | H | tert-butyl | 2-F—C₆H₄ |
| A.909 | H | ethyl | H | tert-butyl | 2-Cl—C₆H₄ |
| A.910 | H | ethyl | H | tert-butyl | 2-CH₃—C₆H₄ |
| A.911 | H | ethyl | H | tert-butyl | 2-CF₃—C₆H₄ |
| A.912 | H | ethyl | H | tert-butyl | 3-F—C₆H₄ |
| A.913 | H | ethyl | H | tert-butyl | 3-Cl—C₆H₄ |
| A.914 | H | ethyl | H | tert-butyl | 3-CH₃—C₆H₄ |

TABLE A-continued

| No. | Y | R¹ | R² | R³ | R⁴ |
|---|---|---|---|---|---|
| A.915 | H | ethyl | H | tert-butyl | 3-CF$_3$—C$_6$H$_4$ |
| A.916 | H | ethyl | H | tert-butyl | 3-Br—C$_6$H$_4$ |
| A.917 | H | ethyl | H | tert-butyl | 4-F—C$_6$H$_4$ |
| A.918 | H | ethyl | H | tert-butyl | 4-Cl—C$_6$H$_4$ |
| A.919 | H | ethyl | H | tert-butyl | 4-CH$_3$—C$_6$H$_4$ |
| A.920 | H | ethyl | H | tert-butyl | 4-CF$_3$—C$_6$H$_4$ |
| A.921 | H | ethyl | H | tert-butyl | 4-OCH$_3$—C$_6$H$_4$ |
| A.922 | H | ethyl | H | tert-butyl | 4-OCF$_3$—C$_6$H$_4$ |
| A.923 | H | ethyl | H | tert-butyl | 4-Br—C$_6$H$_4$ |
| A.924 | H | ethyl | H | tert-butyl | 4-(CH=NOCH$_3$)—C$_6$H$_4$ |
| A.925 | H | ethyl | H | tert-butyl | 4-(CH=NOEt)—C$_6$H$_4$ |
| A.926 | H | ethyl | H | tert-butyl | 4-[C(CH$_3$)=NOCH$_3$]—C$_6$H$_4$ |
| A.927 | H | ethyl | H | tert-butyl | 4-[C(CH$_3$)=NOEt]—C$_6$H$_4$ |
| A.928 | H | ethyl | H | tert-butyl | 2,4-F$_2$—C$_6$H$_3$ |
| A.929 | H | ethyl | H | tert-butyl | 2,4-Cl$_2$—C$_6$H$_3$ |
| A.930 | H | ethyl | H | tert-butyl | 2,4-(CH$_3$)$_2$—C$_6$H$_3$ |
| A.931 | H | ethyl | H | tert-butyl | 3,5-F$_2$—C$_6$H$_3$ |
| A.932 | H | ethyl | H | tert-butyl | 3,5-Cl$_2$—C$_6$H$_3$ |
| A.933 | H | ethyl | H | tert-butyl | 3,5-(CH$_3$)$_2$—C$_6$H$_3$ |
| A.934 | H | ethyl | H | tert-butyl | 2-F-4-Cl—C$_6$H$_3$ |
| A.935 | H | ethyl | H | tert-butyl | 2-Cl-4-F—C$_6$H$_3$ |
| A.936 | H | ethyl | H | tert-butyl | 3,4-F$_2$—C$_6$H$_3$ |
| A.937 | H | ethyl | H | tert-butyl | 3,4-Cl$_2$—C$_6$H$_3$ |
| A.938 | H | ethyl | H | tert-butyl | 2,3-F$_2$—C$_6$H$_3$ |
| A.939 | H | ethyl | H | tert-butyl | CH$_3$ |
| A.940 | H | ethyl | H | tert-butyl | ethyl |
| A.941 | H | ethyl | H | tert-butyl | n-propyl |
| A.942 | H | ethyl | H | tert-butyl | isopropyl |
| A.943 | H | ethyl | H | tert-butyl | tert-butyl |
| A.944 | H | ethyl | H | tert-butyl | n-butyl |
| A.945 | H | ethyl | H | tert-butyl | C$_6$H$_5$ |
| A.946 | H | ethyl | H | tert-butyl | 2-F—C$_6$H$_4$ |
| A.947 | H | ethyl | H | tert-butyl | 2-Cl—C$_6$H$_4$ |
| A.948 | H | ethyl | H | tert-butyl | 2-CH$_3$—C$_6$H$_4$ |
| A.949 | H | ethyl | H | tert-butyl | 2-CF$_3$—C$_6$H$_4$ |
| A.950 | H | ethyl | H | tert-butyl | 3-F—C$_6$H$_4$ |
| A.951 | H | ethyl | H | tert-butyl | 3-Cl—C$_6$H$_4$ |
| A.952 | H | ethyl | H | tert-butyl | 3-CH$_3$—C$_6$H$_4$ |
| A.953 | H | ethyl | H | tert-butyl | 3-CF$_3$—C$_6$H$_4$ |
| A.954 | H | ethyl | H | tert-butyl | 3-Br—C$_6$H$_4$ |
| A.955 | H | ethyl | H | tert-butyl | 4-F—C$_6$H$_4$ |
| A.956 | H | ethyl | H | tert-butyl | 4-Cl—C$_6$H$_4$ |
| A.957 | H | ethyl | H | tert-butyl | 4-CH$_3$—C$_6$H$_4$ |
| A.958 | H | ethyl | H | tert-butyl | 4-CF$_3$—C$_6$H$_4$ |
| A.959 | H | ethyl | H | tert-butyl | 4-OCH$_3$—C$_6$H$_4$ |
| A.960 | H | ethyl | H | tert-butyl | 4-OCF$_3$—C$_6$H$_4$ |
| A.961 | H | ethyl | H | tert-butyl | 4-Br—C$_6$H$_4$ |
| A.962 | H | ethyl | H | tert-butyl | 4-(CH=NOCH$_3$)—C$_6$H$_4$ |
| A.963 | H | ethyl | H | tert-butyl | 4-(CH=NOEt)—C$_6$H$_4$ |
| A.964 | H | ethyl | H | tert-butyl | 4-[C(CH$_3$)=NOCH$_3$]—C$_6$H$_4$ |
| A.965 | H | ethyl | H | tert-butyl | 4-[C(CH$_3$)=NOEt]—C$_6$H$_4$ |
| A.966 | H | ethyl | H | tert-butyl | 2,4-F$_2$—C$_6$H$_3$ |
| A.967 | H | ethyl | H | tert-butyl | 2,4-Cl$_2$—C$_6$H$_3$ |
| A.968 | H | ethyl | H | tert-butyl | 2,4-(CH$_3$)$_2$—C$_6$H$_3$ |
| A.969 | H | ethyl | H | tert-butyl | 3,5-F$_2$—C$_6$H$_3$ |
| A.970 | H | ethyl | H | tert-butyl | 3,5-Cl$_2$—C$_6$H$_3$ |
| A.971 | H | ethyl | H | tert-butyl | 3,5-(CH$_3$)$_2$—C$_6$H$_3$ |
| A.972 | H | ethyl | H | tert-butyl | 2-F-4-Cl—C$_6$H$_3$ |
| A.973 | H | ethyl | H | tert-butyl | 2-Cl-4-F—C$_6$H$_3$ |
| A.974 | H | ethyl | H | tert-butyl | 3,4-F$_2$—C$_6$H$_3$ |
| A.975 | H | ethyl | H | tert-butyl | 3,4-Cl$_2$—C$_6$H$_3$ |
| A.976 | H | ethyl | H | tert-butyl | 2,3-F$_2$—C$_6$H$_3$ |
| A.977 | H | Cl | H | H | CH$_3$ |
| A.978 | H | Cl | H | H | ethyl |
| A.979 | H | Cl | H | H | n-propyl |
| A.980 | H | Cl | H | H | isopropyl |
| A.981 | H | Cl | H | H | tert-butyl |
| A.982 | H | Cl | H | H | n-butyl |
| A.983 | H | Cl | H | H | C$_6$H$_5$ |
| A.984 | H | Cl | H | H | 2-F—C$_6$H$_4$ |
| A.985 | H | Cl | H | H | 2-Cl—C$_6$H$_4$ |
| A.986 | H | Cl | H | H | 2-CH$_3$—C$_6$H$_4$ |
| A.987 | H | Cl | H | H | 2-CF$_3$—C$_6$H$_4$ |
| A.988 | H | Cl | H | H | 3-F—C$_6$H$_4$ |
| A.989 | H | Cl | H | H | 3-Cl—C$_6$H$_4$ |
| A.990 | H | Cl | H | H | 3-CH$_3$—C$_6$H$_4$ |
| A.991 | H | Cl | H | H | 3-CF$_3$—C$_6$H$_4$ |

TABLE A-continued

| No. | Y | R¹ | R² | R³ | R⁴ |
|---|---|---|---|---|---|
| A.992 | H | Cl | H | H | 3-Br—C$_6$H$_4$ |
| A.993 | H | Cl | H | H | 4-F—C$_6$H$_4$ |
| A.994 | H | Cl | H | H | 4-Cl—C$_6$H$_4$ |
| A.995 | H | Cl | H | H | 4-CH$_3$—C$_6$H$_4$ |
| A.996 | H | Cl | H | H | 4-CF$_3$—C$_6$H$_4$ |
| A.997 | H | Cl | H | H | 4-OCH$_3$—C$_6$H$_4$ |
| A.998 | H | Cl | H | H | 4-OCF$_3$—C$_6$H$_4$ |
| A.999 | H | Cl | H | H | 4-Br—C$_6$H$_4$ |
| A.1000 | H | Cl | H | H | 4-(CH=NOCH$_3$)—C$_6$H$_4$ |
| A.1001 | H | Cl | H | H | 4-(CH=NOEt)—C$_6$H$_4$ |
| A.1002 | H | Cl | H | H | 4-[C(CH$_3$)=NOCH$_3$]—C$_6$H$_4$ |
| A.1003 | H | Cl | H | H | 4-[C(CH$_3$)=NOEt]—C$_6$H$_4$ |
| A.1004 | H | Cl | H | H | 2,4-F$_2$—C$_6$H$_3$ |
| A.1005 | H | Cl | H | H | 2,4-Cl$_2$—C$_6$H$_3$ |
| A.1006 | H | Cl | H | H | 2,4-(CH$_3$)$_2$—C$_6$H$_3$ |
| A.1007 | H | Cl | H | H | 3,5-F$_2$—C$_6$H$_3$ |
| A.1008 | H | Cl | H | H | 3,5-Cl$_2$—C$_6$H$_3$ |
| A.1009 | H | Cl | H | H | 3,5-(CH$_3$)$_2$—C$_6$H$_3$ |
| A.1010 | H | Cl | H | H | 2-F-4-Cl—C$_6$H$_3$ |
| A.1011 | H | Cl | H | H | 2-Cl-4-F—C$_6$H$_3$ |
| A.1012 | H | Cl | H | H | 3,4-F$_2$—C$_6$H$_3$ |
| A.1013 | H | Cl | H | H | 3,4-Cl$_2$—C$_6$H$_3$ |
| A.1014 | H | Cl | H | H | 2,3-F$_2$—C$_6$H$_3$ |
| A.1015 | H | Cl | H | CH$_3$ | CH$_3$ |
| A.1016 | H | Cl | H | CH$_3$ | ethyl |
| A.1017 | H | Cl | H | CH$_3$ | n-propyl |
| A.1018 | H | Cl | H | CH$_3$ | isopropyl |
| A.1019 | H | Cl | H | CH$_3$ | tert-butyl |
| A.1020 | H | Cl | H | CH$_3$ | n-butyl |
| A.1021 | H | Cl | H | CH$_3$ | C$_6$H$_5$ |
| A.1022 | H | Cl | H | CH$_3$ | 2-F—C$_6$H$_4$ |
| A.1023 | H | Cl | H | CH$_3$ | 2-Cl—C$_6$H$_4$ |
| A.1024 | H | Cl | H | CH$_3$ | 2-CH$_3$—C$_6$H$_4$ |
| A.1025 | H | Cl | H | CH$_3$ | 2-CF$_3$—C$_6$H$_4$ |
| A.1026 | H | Cl | H | CH$_3$ | 3-F—C$_6$H$_4$ |
| A.1027 | H | Cl | H | CH$_3$ | 3-Cl—C$_6$H$_4$ |
| A.1028 | H | Cl | H | CH$_3$ | 3-CH$_3$—C$_6$H$_4$ |
| A.1029 | H | Cl | H | CH$_3$ | 3-CF$_3$—C$_6$H$_4$ |
| A.1030 | H | Cl | H | CH$_3$ | 3-Br—C$_6$H$_4$ |
| A.1031 | H | Cl | H | CH$_3$ | 4-F—C$_6$H$_4$ |
| A.1032 | H | Cl | H | CH$_3$ | 4-Cl—C$_6$H$_4$ |
| A.1033 | H | Cl | H | CH$_3$ | 4-CH$_3$—C$_6$H$_4$ |
| A.1034 | H | Cl | H | CH$_3$ | 4-CF$_3$—C$_6$H$_4$ |
| A.1035 | H | Cl | H | CH$_3$ | 4-OCH$_3$—C$_6$H$_4$ |
| A.1036 | H | Cl | H | CH$_3$ | 4-OCF$_3$—C$_6$H$_4$ |
| A.1037 | H | Cl | H | CH$_3$ | 4-Br—C$_6$H$_4$ |
| A.1038 | H | Cl | H | CH$_3$ | 4-(CH=NOCH$_3$)—C$_6$H$_4$ |
| A.1039 | H | Cl | H | CH$_3$ | 4-(CH=NOEt)—C$_6$H$_4$ |
| A.1040 | H | Cl | H | CH$_3$ | 4-[C(CH$_3$)=NOCH$_3$]—C$_6$H$_4$ |
| A.1041 | H | Cl | H | CH$_3$ | 4-[C(CH$_3$)=NOEt]—C$_6$H$_4$ |
| A.1042 | H | Cl | H | CH$_3$ | 2,4-F$_2$—C$_6$H$_3$ |
| A.1043 | H | Cl | H | CH$_3$ | 2,4-Cl$_2$—C$_6$H$_3$ |
| A.1044 | H | Cl | H | CH$_3$ | 2,4-(CH$_3$)$_2$—C$_6$H$_3$ |
| A.1045 | H | Cl | H | CH$_3$ | 3,5-F$_2$—C$_6$H$_3$ |
| A.1046 | H | Cl | H | CH$_3$ | 3,5-Cl$_2$—C$_6$H$_3$ |
| A.1047 | H | Cl | H | CH$_3$ | 3,5-(CH$_3$)$_2$—C$_6$H$_3$ |
| A.1048 | H | Cl | H | CH$_3$ | 2-F-4-Cl—C$_6$H$_3$ |
| A.1049 | H | Cl | H | CH$_3$ | 2-Cl-4-F—C$_6$H$_3$ |
| A.1050 | H | Cl | H | CH$_3$ | 3,4-F$_2$—C$_6$H$_3$ |
| A.1051 | H | Cl | H | CH$_3$ | 3,4-Cl$_2$—C$_6$H$_3$ |
| A.1052 | H | Cl | H | CH$_3$ | 2,3-F$_2$—C$_6$H$_3$ |
| A.1053 | H | Cl | H | ethyl | CH$_3$ |
| A.1054 | H | Cl | H | ethyl | ethyl |
| A.1055 | H | Cl | H | ethyl | n-propyl |
| A.1056 | H | Cl | H | ethyl | isopropyl |
| A.1057 | H | Cl | H | ethyl | tert-butyl |
| A.1058 | H | Cl | H | ethyl | n-butyl |
| A.1059 | H | Cl | H | ethyl | C$_6$H$_5$ |
| A.1060 | H | Cl | H | ethyl | 2-F—C$_6$H$_4$ |
| A.1061 | H | Cl | H | ethyl | 2-Cl—C$_6$H$_4$ |
| A.1062 | H | Cl | H | ethyl | 2-CH$_3$—C$_6$H$_4$ |
| A.1063 | H | Cl | H | ethyl | 2-CF$_3$—C$_6$H$_4$ |
| A.1064 | H | Cl | H | ethyl | 3-F—C$_6$H$_4$ |
| A.1065 | H | Cl | H | ethyl | 3-Cl—C$_6$H$_4$ |
| A.1066 | H | Cl | H | ethyl | 3-CH$_3$—C$_6$H$_4$ |
| A.1067 | H | Cl | H | ethyl | 3-CF$_3$—C$_6$H$_4$ |
| A.1068 | H | Cl | H | ethyl | 3-Br—C$_6$H$_4$ |

TABLE A-continued

| No. | Y | R¹ | R² | R³ | R⁴ |
|---|---|---|---|---|---|
| A.1069 | H | Cl | H | ethyl | 4-F—C₆H₄ |
| A.1070 | H | Cl | H | ethyl | 4-Cl—C₆H₄ |
| A.1071 | H | Cl | H | ethyl | 4-CH₃—C₆H₄ |
| A.1072 | H | Cl | H | ethyl | 4-CF₃—C₆H₄ |
| A.1073 | H | Cl | H | ethyl | 4-OCH₃—C₆H₄ |
| A.1074 | H | Cl | H | ethyl | 4-OCF₃—C₆H₄ |
| A.1075 | H | Cl | H | ethyl | 4-Br—C₆H₄ |
| A.1076 | H | Cl | H | ethyl | 4-(CH=NOCH₃)—C₆H₄ |
| A.1077 | H | Cl | H | ethyl | 4-(CH=NOEt)—C₆H₄ |
| A.1078 | H | Cl | H | ethyl | 4-[C(CH₃)=NOCH₃]—C₆H₄ |
| A.1079 | H | Cl | H | ethyl | 4-[C(CH₃)=NOEt]—C₆H₄ |
| A.1080 | H | Cl | H | ethyl | 2,4-F₂—C₆H₃ |
| A.1081 | H | Cl | H | ethyl | 2,4-Cl₂—C₆H₃ |
| A.1082 | H | Cl | H | ethyl | 2,4-(CH₃)₂—C₆H₃ |
| A.1083 | H | Cl | H | ethyl | 3,5-F₂—C₆H₃ |
| A.1084 | H | Cl | H | ethyl | 3,5-Cl₂—C₆H₃ |
| A.1085 | H | Cl | H | ethyl | 3,5-(CH₃)₂—C₆H₃ |
| A.1086 | H | Cl | H | ethyl | 2-F-4-Cl—C₆H₃ |
| A.1087 | H | Cl | H | ethyl | 2-Cl-4-F—C₆H₃ |
| A.1088 | H | Cl | H | ethyl | 3,4-F₂—C₆H₃ |
| A.1089 | H | Cl | H | ethyl | 3,4-Cl₂—C₆H₃ |
| A.1090 | H | Cl | H | ethyl | 2,3-F₂—C₆H₃ |
| A.1091 | H | Cl | H | n-propyl | CH₃ |
| A.1092 | H | Cl | H | n-propyl | ethyl |
| A.1093 | H | Cl | H | n-propyl | n-propyl |
| A.1094 | H | Cl | H | n-propyl | isopropyl |
| A.1095 | H | Cl | H | n-propyl | tert-butyl |
| A.1096 | H | Cl | H | n-propyl | n-butyl |
| A.1097 | H | Cl | H | n-propyl | C₆H₅ |
| A.1098 | H | Cl | H | n-propyl | 2-F—C₆H₄ |
| A.1099 | H | Cl | H | n-propyl | 2-Cl—C₆H₄ |
| A.1100 | H | Cl | H | n-propyl | 2-CH₃—C₆H₄ |
| A.1101 | H | Cl | H | n-propyl | 2-CF₃—C₆H₄ |
| A.1102 | H | Cl | H | n-propyl | 3-F—C₆H₄ |
| A.1103 | H | Cl | H | n-propyl | 3-Cl—C₆H₄ |
| A.1104 | H | Cl | H | n-propyl | 3-CH₃—C₆H₄ |
| A.1105 | H | Cl | H | n-propyl | 3-CF₃—C₆H₄ |
| A.1106 | H | Cl | H | n-propyl | 3-Br—C₆H₄ |
| A.1107 | H | Cl | H | n-propyl | 4-F—C₆H₄ |
| A.1108 | H | Cl | H | n-propyl | 4-Cl—C₆H₄ |
| A.1109 | H | Cl | H | n-propyl | 4-CH₃—C₆H₄ |
| A.1110 | H | Cl | H | n-propyl | 4-CF₃—C₆H₄ |
| A.1111 | H | Cl | H | n-propyl | 4-OCH₃—C₆H₄ |
| A.1112 | H | Cl | H | n-propyl | 4-OCF₃—C₆H₄ |
| A.1113 | H | Cl | H | n-propyl | 4-Br—C₆H₄ |
| A.1114 | H | Cl | H | n-propyl | 4-(CH=NOCH₃)—C₆H₄ |
| A.1115 | H | Cl | H | n-propyl | 4-(CH=NOEt)—C₆H₄ |
| A.1116 | H | Cl | H | n-propyl | 4-[C(CH₃)=NOCH₃]—C₆H₄ |
| A.1117 | H | Cl | H | n-propyl | 4-[C(CH₃)=NOEt]—C₆H₄ |
| A.1118 | H | Cl | H | n-propyl | 2,4-F₂—C₆H₃ |
| A.1119 | H | Cl | H | n-propyl | 2,4-Cl₂—C₆H₃ |
| A.1120 | H | Cl | H | n-propyl | 2,4-(CH₃)₂—C₆H₃ |
| A.1121 | H | Cl | H | n-propyl | 3,5-F₂—C₆H₃ |
| A.1122 | H | Cl | H | n-propyl | 3,5-Cl₂—C₆H₃ |
| A.1123 | H | Cl | H | n-propyl | 3,5-(CH₃)₂—C₆H₃ |
| A.1124 | H | Cl | H | n-propyl | 2-F-4-Cl—C₆H₃ |
| A.1125 | H | Cl | H | n-propyl | 2-Cl-4-F—C₆H₃ |
| A.1126 | H | Cl | H | n-propyl | 3,4-F₂—C₆H₃ |
| A.1127 | H | Cl | H | n-propyl | 3,4-Cl₂—C₆H₃ |
| A.1128 | H | Cl | H | n-propyl | 2,3-F₂—C₆H₃ |
| A.1129 | H | Cl | H | n-propyl | CH₃ |
| A.1130 | H | Cl | H | n-propyl | ethyl |
| A.1131 | H | Cl | H | n-propyl | n-propyl |
| A.1132 | H | Cl | H | n-propyl | isopropyl |
| A.1133 | H | Cl | H | n-propyl | tert-butyl |
| A.1134 | H | Cl | H | n-propyl | n-butyl |
| A.1135 | H | Cl | H | n-propyl | C₆H₅ |
| A.1136 | H | Cl | H | n-propyl | 2-F—C₆H₄ |
| A.1137 | H | Cl | H | n-propyl | 2-Cl—C₆H₄ |
| A.1138 | H | Cl | H | n-propyl | 2-CH₃—C₆H₄ |
| A.1139 | H | Cl | H | n-propyl | 2-CF₃—C₆H₄ |
| A.1140 | H | Cl | H | n-propyl | 3-F—C₆H₄ |
| A.1141 | H | Cl | H | n-propyl | 3-Cl—C₆H₄ |
| A.1142 | H | Cl | H | n-propyl | 3-CH₃—C₆H₄ |
| A.1143 | H | Cl | H | n-propyl | 3-CF₃—C₆H₄ |
| A.1144 | H | Cl | H | n-propyl | 3-Br—C₆H₄ |
| A.1145 | H | Cl | H | n-propyl | 4-F—C₆H₄ |

TABLE A-continued

| No. | Y | R¹ | R² | R³ | R⁴ |
|---|---|---|---|---|---|
| A.1146 | H | Cl | H | n-propyl | 4-Cl—C₆H₄ |
| A.1147 | H | Cl | H | n-propyl | 4-CH₃—C₆H₄ |
| A.1148 | H | Cl | H | n-propyl | 4-CF₃—C₆H₄ |
| A.1149 | H | Cl | H | n-propyl | 4-OCH₃—C₆H₄ |
| A.1150 | H | Cl | H | n-propyl | 4-OCF₃—C₆H₄ |
| A.1151 | H | Cl | H | n-propyl | 4-Br—C₆H₄ |
| A.1152 | H | Cl | H | n-propyl | 4-(CH═NOCH₃)—C₆H₄ |
| A.1153 | H | Cl | H | n-propyl | 4-(CH═NOEt)—C₆H₄ |
| A.1154 | H | Cl | H | n-propyl | 4-[C(CH₃)═NOCH₃]—C₆H₄ |
| A.1155 | H | Cl | H | n-propyl | 4-[C(CH₃)═NOEt]—C₆H₄ |
| A.1156 | H | Cl | H | n-propyl | 2,4-F₂—C₆H₃ |
| A.1157 | H | Cl | H | n-propyl | 2,4-Cl₂—C₆H₃ |
| A.1158 | H | Cl | H | n-propyl | 2,4-(CH₃)₂—C₆H₃ |
| A.1159 | H | Cl | H | n-propyl | 3,5-F₂—C₆H₃ |
| A.1160 | H | Cl | H | n-propyl | 3,5-Cl₂—C₆H₃ |
| A.1161 | H | Cl | H | n-propyl | 3,5-(CH₃)₂—C₆H₃ |
| A.1162 | H | Cl | H | n-propyl | 2-F-4-Cl—C₆H₃ |
| A.1163 | H | Cl | H | n-propyl | 2-Cl-4-F—C₆H₃ |
| A.1164 | H | Cl | H | n-propyl | 3,4-F₂—C₆H₃ |
| A.1165 | H | Cl | H | n-propyl | 3,4-Cl₂—C₆H₃ |
| A.1166 | H | Cl | H | n-propyl | 2,3-F₂—C₆H₃ |
| A.1167 | H | Cl | H | n-butyl | CH₃ |
| A.1168 | H | Cl | H | n-butyl | ethyl |
| A.1169 | H | Cl | H | n-butyl | n-propyl |
| A.1170 | H | Cl | H | n-butyl | isopropyl |
| A.1171 | H | Cl | H | n-butyl | tert-butyl |
| A.1172 | H | Cl | H | n-butyl | n-butyl |
| A.1173 | H | Cl | H | n-butyl | C₆H₅ |
| A.1174 | H | Cl | H | n-butyl | 2-F—C₆H₄ |
| A.1175 | H | Cl | H | n-butyl | 2-Cl—C₆H₄ |
| A.1176 | H | Cl | H | n-butyl | 2-CH₃—C₆H₄ |
| A.1177 | H | Cl | H | n-butyl | 2-CF₃—C₆H₄ |
| A.1178 | H | Cl | H | n-butyl | 3-F—C₆H₄ |
| A.1179 | H | Cl | H | n-butyl | 3-Cl—C₆H₄ |
| A.1180 | H | Cl | H | n-butyl | 3-CH₃—C₆H₄ |
| A.1181 | H | Cl | H | n-butyl | 3-CF₃—C₆H₄ |
| A.1182 | H | Cl | H | n-butyl | 3-Br—C₆H₄ |
| A.1183 | H | Cl | H | n-butyl | 4-F—C₆H₄ |
| A.1184 | H | Cl | H | n-butyl | 4-Cl—C₆H₄ |
| A.1185 | H | Cl | H | n-butyl | 4-CH₃—C₆H₄ |
| A.1186 | H | Cl | H | n-butyl | 4-CF₃—C₆H₄ |
| A.1187 | H | Cl | H | n-butyl | 4-OCH₃—C₆H₄ |
| A.1188 | H | Cl | H | n-butyl | 4-OCF₃—C₆H₄ |
| A.1189 | H | Cl | H | n-butyl | 4-Br—C₆H₄ |
| A.1190 | H | Cl | H | n-butyl | 4-(CH═NOCH₃)—C₆H₄ |
| A.1191 | H | Cl | H | n-butyl | 4-(CH═NOEt)—C₆H₄ |
| A.1192 | H | Cl | H | n-butyl | 4-[C(CH₃)═NOCH₃]—C₆H₄ |
| A.1193 | H | Cl | H | n-butyl | 4-[C(CH₃)═NOEt]—C₆H₄ |
| A.1194 | H | Cl | H | n-butyl | 2,4-F₂—C₆H₃ |
| A.1195 | H | Cl | H | n-butyl | 2,4-Cl₂—C₆H₃ |
| A.1196 | H | Cl | H | n-butyl | 2,4-(CH₃)₂—C₆H₃ |
| A.1197 | H | Cl | H | n-butyl | 3,5-F₂—C₆H₃ |
| A.1198 | H | Cl | H | n-butyl | 3,5-Cl₂—C₆H₃ |
| A.1199 | H | Cl | H | n-butyl | 3,5-(CH₃)₂—C₆H₃ |
| A.1200 | H | Cl | H | n-butyl | 2-F-4-Cl—C₆H₃ |
| A.1201 | H | Cl | H | n-butyl | 2-Cl-4-F—C₆H₃ |
| A.1202 | H | Cl | H | n-butyl | 3,4-F₂—C₆H₃ |
| A.1203 | H | Cl | H | n-butyl | 3,4-Cl₂—C₆H₃ |
| A.1204 | H | Cl | H | n-butyl | 2,3-F₂—C₆H₃ |
| A.1205 | H | Cl | H | n-butyl | CH₃ |
| A.1206 | H | Cl | H | n-butyl | ethyl |
| A.1207 | H | Cl | H | n-butyl | n-propyl |
| A.1208 | H | Cl | H | n-butyl | isopropyl |
| A.1209 | H | Cl | H | n-butyl | tert-butyl |
| A.1210 | H | Cl | H | n-butyl | n-butyl |
| A.1211 | H | Cl | H | n-butyl | C₆H₅ |
| A.1212 | H | Cl | H | n-butyl | 2-F—C₆H₄ |
| A.1213 | H | Cl | H | n-butyl | 2-Cl—C₆H₄ |
| A.1214 | H | Cl | H | n-butyl | 2-CH₃—C₆H₄ |
| A.1215 | H | Cl | H | n-butyl | 2-CF₃—C₆H₄ |
| A.1216 | H | Cl | H | n-butyl | 3-F—C₆H₄ |
| A.1217 | H | Cl | H | n-butyl | 3-Cl—C₆H₄ |
| A.1218 | H | Cl | H | n-butyl | 3-CH₃—C₆H₄ |
| A.1219 | H | Cl | H | n-butyl | 3-CF₃—C₆H₄ |
| A.1220 | H | Cl | H | n-butyl | 3-Br—C₆H₄ |
| A.1221 | H | Cl | H | n-butyl | 4-F—C₆H₄ |
| A.1222 | H | Cl | H | n-butyl | 4-Cl—C₆H₄ |

TABLE A-continued

| No. | Y | R¹ | R² | R³ | R⁴ |
|---|---|---|---|---|---|
| A.1223 | H | Cl | H | n-butyl | 4-CH$_3$—C$_6$H$_4$ |
| A.1224 | H | Cl | H | n-butyl | 4-CF$_3$—C$_6$H$_4$ |
| A.1225 | H | Cl | H | n-butyl | 4-OCH$_3$—C$_6$H$_4$ |
| A.1226 | H | Cl | H | n-butyl | 4-OCF$_3$—C$_6$H$_4$ |
| A.1227 | H | Cl | H | n-butyl | 4-Br—C$_6$H$_4$ |
| A.1228 | H | Cl | H | n-butyl | 4-(CH=NOCH$_3$)—C$_6$H$_4$ |
| A.1229 | H | Cl | H | n-butyl | 4-(CH=NOEt)—C$_6$H$_4$ |
| A.1230 | H | Cl | H | n-butyl | 4-[C(CH$_3$)=NOCH$_3$]—C$_6$H$_4$ |
| A.1231 | H | Cl | H | n-butyl | 4-[C(CH$_3$)=NOEt]—C$_6$H$_4$ |
| A.1232 | H | Cl | H | n-butyl | 2,4-F$_2$—C$_6$H$_3$ |
| A.1233 | H | Cl | H | n-butyl | 2,4-Cl$_2$—C$_6$H$_3$ |
| A.1234 | H | Cl | H | n-butyl | 2,4-(CH$_3$)$_2$—C$_6$H$_3$ |
| A.1235 | H | Cl | H | n-butyl | 3,5-F$_2$—C$_6$H$_3$ |
| A.1236 | H | Cl | H | n-butyl | 3,5-Cl$_2$—C$_6$H$_3$ |
| A.1237 | H | Cl | H | n-butyl | 3,5-(CH$_3$)$_2$—C$_6$H$_3$ |
| A.1238 | H | Cl | H | n-butyl | 2-F-4-Cl—C$_6$H$_3$ |
| A.1239 | H | Cl | H | n-butyl | 2-Cl-4-F—C$_6$H$_3$ |
| A.1240 | H | Cl | H | n-butyl | 3,4-F$_2$—C$_6$H$_3$ |
| A.1241 | H | Cl | H | n-butyl | 3,4-Cl$_2$—C$_6$H$_3$ |
| A.1242 | H | Cl | H | n-butyl | 2,3-F$_2$—C$_6$H$_3$ |
| A.1243 | H | Cl | H | isopropyl | CH$_3$ |
| A.1244 | H | Cl | H | isopropyl | ethyl |
| A.1245 | H | Cl | H | isopropyl | n-propyl |
| A.1246 | H | Cl | H | isopropyl | isopropyl |
| A.1247 | H | Cl | H | isopropyl | tert-butyl |
| A.1248 | H | Cl | H | isopropyl | n-butyl |
| A.1249 | H | Cl | H | isopropyl | C$_6$H$_5$ |
| A.1250 | H | Cl | H | isopropyl | 2-F—C$_6$H$_4$ |
| A.1251 | H | Cl | H | isopropyl | 2-Cl—C$_6$H$_4$ |
| A.1252 | H | Cl | H | isopropyl | 2-CH$_3$—C$_6$H$_4$ |
| A.1253 | H | Cl | H | isopropyl | 2-CF$_3$—C$_6$H$_4$ |
| A.1254 | H | Cl | H | isopropyl | 3-F—C$_6$H$_4$ |
| A.1255 | H | Cl | H | isopropyl | 3-Cl—C$_6$H$_4$ |
| A.1256 | H | Cl | H | isopropyl | 3-CH$_3$—C$_6$H$_4$ |
| A.1257 | H | Cl | H | isopropyl | 3-CF$_3$—C$_6$H$_4$ |
| A.1258 | H | Cl | H | isopropyl | 3-Br—C$_6$H$_4$ |
| A.1259 | H | Cl | H | isopropyl | 4-F—C$_6$H$_4$ |
| A.1260 | H | Cl | H | isopropyl | 4-Cl—C$_6$H$_4$ |
| A.1261 | H | Cl | H | isopropyl | 4-CH$_3$—C$_6$H$_4$ |
| A.1262 | H | Cl | H | isopropyl | 4-CF$_3$—C$_6$H$_4$ |
| A.1263 | H | Cl | H | isopropyl | 4-OCH$_3$—C$_6$H$_4$ |
| A.1264 | H | Cl | H | isopropyl | 4-OCF$_3$—C$_6$H$_4$ |
| A.1265 | H | Cl | H | isopropyl | 4-Br—C$_6$H$_4$ |
| A.1266 | H | Cl | H | isopropyl | 4-(CH=NOCH$_3$)—C$_6$H$_4$ |
| A.1267 | H | Cl | H | isopropyl | 4-(CH=NOEt)—C$_6$H$_4$ |
| A.1268 | H | Cl | H | isopropyl | 4-[C(CH$_3$)=NOCH$_3$]—C$_6$H$_4$ |
| A.1269 | H | Cl | H | isopropyl | 4-[C(CH$_3$)=NOEt]—C$_6$H$_4$ |
| A.1270 | H | Cl | H | isopropyl | 2,4-F$_2$—C$_6$H$_3$ |
| A.1271 | H | Cl | H | isopropyl | 2,4-Cl$_2$—C$_6$H$_3$ |
| A.1272 | H | Cl | H | isopropyl | 2,4-(CH$_3$)$_2$—C$_6$H$_3$ |
| A.1273 | H | Cl | H | isopropyl | 3,5-F$_2$—C$_6$H$_3$ |
| A.1274 | H | Cl | H | isopropyl | 3,5-Cl$_2$—C$_6$H$_3$ |
| A.1275 | H | Cl | H | isopropyl | 3,5-(CH$_3$)$_2$—C$_6$H$_3$ |
| A.1276 | H | Cl | H | isopropyl | 2-F-4-Cl—C$_6$H$_3$ |
| A.1277 | H | Cl | H | isopropyl | 2-Cl-4-F—C$_6$H$_3$ |
| A.1278 | H | Cl | H | isopropyl | 3,4-F$_2$—C$_6$H$_3$ |
| A.1279 | H | Cl | H | isopropyl | 3,4-Cl$_2$—C$_6$H$_3$ |
| A.1280 | H | Cl | H | isopropyl | 2,3-F$_2$—C$_6$H$_3$ |
| A.1281 | H | Cl | H | isopropyl | CH$_3$ |
| A.1282 | H | Cl | H | isopropyl | ethyl |
| A.1283 | H | Cl | H | isopropyl | n-propyl |
| A.1284 | H | Cl | H | isopropyl | isopropyl |
| A.1285 | H | Cl | H | isopropyl | tert-butyl |
| A.1286 | H | Cl | H | isopropyl | n-butyl |
| A.1287 | H | Cl | H | isopropyl | C$_6$H$_5$ |
| A.1288 | H | Cl | H | isopropyl | 2-F—C$_6$H$_4$ |
| A.1289 | H | Cl | H | isopropyl | 2-Cl—C$_6$H$_4$ |
| A.1290 | H | Cl | H | isopropyl | 2-CH$_3$—C$_6$H$_4$ |
| A.1291 | H | Cl | H | isopropyl | 2-CF$_3$—C$_6$H$_4$ |
| A.1292 | H | Cl | H | isopropyl | 3-F—C$_6$H$_4$ |
| A.1293 | H | Cl | H | isopropyl | 3-Cl—C$_6$H$_4$ |
| A.1294 | H | Cl | H | isopropyl | 3-CH$_3$—C$_6$H$_4$ |
| A.1295 | H | Cl | H | isopropyl | 3-CF$_3$—C$_6$H$_4$ |
| A.1296 | H | Cl | H | isopropyl | 3-Br—C$_6$H$_4$ |
| A.1297 | H | Cl | H | isopropyl | 4-F—C$_6$H$_4$ |
| A.1298 | H | Cl | H | isopropyl | 4-Cl—C$_6$H$_4$ |
| A.1299 | H | Cl | H | isopropyl | 4-CH$_3$—C$_6$H$_4$ |

TABLE A-continued

| No. | Y | R¹ | R² | R³ | R⁴ |
|---|---|---|---|---|---|
| A.1300 | H | Cl | H | isopropyl | 4-CF$_3$—C$_6$H$_4$ |
| A.1301 | H | Cl | H | isopropyl | 4-OCH$_3$—C$_6$H$_4$ |
| A.1303 | H | Cl | H | isopropyl | 4-OCF$_3$—C$_6$H$_4$ |
| A.1302 | H | Cl | H | isopropyl | 4-Br—C$_6$H$_4$ |
| A.1304 | H | Cl | H | isopropyl | 4-(CH=NOCH$_3$)—C$_6$H$_4$ |
| A.1305 | H | Cl | H | isopropyl | 4-(CH=NOEt)—C$_6$H$_4$ |
| A.1306 | H | Cl | H | isopropyl | 4-[C(CH$_3$)=NOCH$_3$]—C$_6$H$_4$ |
| A.1307 | H | Cl | H | isopropyl | 4-[C(CH$_3$)=NOEt]—C$_6$H$_4$ |
| A.1308 | H | Cl | H | isopropyl | 2,4-F$_2$—C$_6$H$_3$ |
| A.1309 | H | Cl | H | isopropyl | 2,4-Cl$_2$—C$_6$H$_3$ |
| A.1310 | H | Cl | H | isopropyl | 2,4-(CH$_3$)$_2$—C$_6$H$_3$ |
| A.1311 | H | Cl | H | isopropyl | 3,5-F$_2$—C$_6$H$_3$ |
| A.1312 | H | Cl | H | isopropyl | 3,5-Cl$_2$—C$_6$H$_3$ |
| A.1313 | H | Cl | H | isopropyl | 3,5-(CH$_3$)$_2$—C$_6$H$_3$ |
| A.1314 | H | Cl | H | isopropyl | 2-F-4-Cl—C$_6$H$_3$ |
| A.1315 | H | Cl | H | isopropyl | 2-Cl-4-F—C$_6$H$_3$ |
| A.1316 | H | Cl | H | isopropyl | 3,4-F$_2$—C$_6$H$_3$ |
| A.1317 | H | Cl | H | isopropyl | 3,4-Cl$_2$—C$_6$H$_3$ |
| A.1318 | H | Cl | H | isopropyl | 2,3-F$_2$—C$_6$H$_3$ |
| A.1319 | H | Cl | H | tert-butyl | CH$_3$ |
| A.1320 | H | Cl | H | tert-butyl | ethyl |
| A.1321 | H | Cl | H | tert-butyl | n-propyl |
| A.1322 | H | Cl | H | tert-butyl | isopropyl |
| A.1323 | H | Cl | H | tert-butyl | tert-butyl |
| A.1324 | H | Cl | H | tert-butyl | n-butyl |
| A.1325 | H | Cl | H | tert-butyl | C$_6$H$_5$ |
| A.1326 | H | Cl | H | tert-butyl | 2-F—C$_6$H$_4$ |
| A.1327 | H | Cl | H | tert-butyl | 2-Cl—C$_6$H$_4$ |
| A.1328 | H | Cl | H | tert-butyl | 2-CH$_3$—C$_6$H$_4$ |
| A.1329 | H | Cl | H | tert-butyl | 2-CF$_3$—C$_6$H$_4$ |
| A.1330 | H | Cl | H | tert-butyl | 3-F—C$_6$H$_4$ |
| A.1231 | H | Cl | H | tert-butyl | 3-Cl—C$_6$H$_4$ |
| A.1332 | H | Cl | H | tert-butyl | 3-CH$_3$—C$_6$H$_4$ |
| A.1333 | H | Cl | H | tert-butyl | 3-CF$_3$—C$_6$H$_4$ |
| A.1334 | H | Cl | H | tert-butyl | 3-Br—C$_6$H$_4$ |
| A.1335 | H | Cl | H | tert-butyl | 4-F—C$_6$H$_4$ |
| A.1336 | H | Cl | H | tert-butyl | 4-Cl—C$_6$H$_4$ |
| A.1337 | H | Cl | H | tert-butyl | 4-CH$_3$—C$_6$H$_4$ |
| A.1338 | H | Cl | H | tert-butyl | 4-CF$_3$—C$_6$H$_4$ |
| A.1339 | H | Cl | H | tert-butyl | 4-OCH$_3$—C$_6$H$_4$ |
| A.1340 | H | Cl | H | tert-butyl | 4-OCF$_3$—C$_6$H$_4$ |
| A.1341 | H | Cl | H | tert-butyl | 4-Br—C$_6$H$_4$ |
| A.1342 | H | Cl | H | tert-butyl | 4-(CH=NOCH$_3$)—C$_6$H$_4$ |
| A.1343 | H | Cl | H | tert-butyl | 4-(CH=NOEt)—C$_6$H$_4$ |
| A.1344 | H | Cl | H | tert-butyl | 4-[C(CH$_3$)=NOCH$_3$]—C$_6$H$_4$ |
| A.1345 | H | Cl | H | tert-butyl | 4-[C(CH$_3$)=NOEt]—C$_6$H$_4$ |
| A.1346 | H | Cl | H | tert-butyl | 2,4-F$_2$—C$_6$H$_3$ |
| A.1347 | H | Cl | H | tert-butyl | 2,4-Cl$_2$—C$_6$H$_3$ |
| A.1348 | H | Cl | H | tert-butyl | 2,4-(CH$_3$)$_2$—C$_6$H$_3$ |
| A.1349 | H | Cl | H | tert-butyl | 3,5-F$_2$—C$_6$H$_3$ |
| A.1350 | H | Cl | H | tert-butyl | 3,5-Cl$_2$—C$_6$H$_3$ |
| A.1351 | H | Cl | H | tert-butyl | 3,5-(CH$_3$)$_2$—C$_6$H$_3$ |
| A.1352 | H | Cl | H | tert-butyl | 2-F-4-Cl—C$_6$H$_3$ |
| A.1353 | H | Cl | H | tert-butyl | 2-Cl-4-F—C$_6$H$_3$ |
| A.1354 | H | Cl | H | tert-butyl | 3,4-F$_2$—C$_6$H$_3$ |
| A.1355 | H | Cl | H | tert-butyl | 3,4-Cl$_2$—C$_6$H$_3$ |
| A.1356 | H | Cl | H | tert-butyl | 2,3-F$_2$—C$_6$H$_3$ |
| A.1357 | H | Cl | H | tert-butyl | CH$_3$ |
| A.1358 | H | Cl | H | tert-butyl | ethyl |
| A.1359 | H | Cl | H | tert-butyl | n-propyl |
| A.1360 | H | Cl | H | tert-butyl | isopropyl |
| A.1361 | H | Cl | H | tert-butyl | tert-butyl |
| A.1362 | H | Cl | H | tert-butyl | n-butyl |
| A.1363 | H | Cl | H | tert-butyl | C$_6$H$_5$ |
| A.1364 | H | Cl | H | tert-butyl | 2-F—C$_6$H$_4$ |
| A.1365 | H | Cl | H | tert-butyl | 2-Cl—C$_6$H$_4$ |
| A.1366 | H | Cl | H | tert-butyl | 2-CH$_3$—C$_6$H$_4$ |
| A.1367 | H | Cl | H | tert-butyl | 2-CF$_3$—C$_6$H$_4$ |
| A.1368 | H | Cl | H | tert-butyl | 3-F—C$_6$H$_4$ |
| A.1369 | H | Cl | H | tert-butyl | 3-Cl—C$_6$H$_4$ |
| A.1370 | H | Cl | H | tert-butyl | 3-CH$_3$—C$_6$H$_4$ |
| A.1371 | H | Cl | H | tert-butyl | 3-CF$_3$—C$_6$H$_4$ |
| A.1372 | H | Cl | H | tert-butyl | 3-Br—C$_6$H$_4$ |
| A.1373 | H | Cl | H | tert-butyl | 4-F—C$_6$H$_4$ |
| A.1374 | H | Cl | H | tert-butyl | 4-Cl—C$_6$H$_4$ |
| A.1375 | H | Cl | H | tert-butyl | 4-CH$_3$—C$_6$H$_4$ |
| A.1376 | H | Cl | H | tert-butyl | 4-CF$_3$—C$_6$H$_4$ |

TABLE A-continued

| No. | Y | R¹ | R² | R³ | R⁴ |
|---|---|---|---|---|---|
| A.1377 | H | Cl | H | tert-butyl | 4-OCH₃—C₆H₄ |
| A.1378 | H | Cl | H | tert-butyl | 4-OCF₃—C₆H₄ |
| A.1379 | H | Cl | H | tert-butyl | 4-Br—C₆H₄ |
| A.1380 | H | Cl | H | tert-butyl | 4-(CH=NOCH₃)—C₆H₄ |
| A.1381 | H | Cl | H | tert-butyl | 4-(CH=NOEt)—C₆H₄ |
| A.1382 | H | Cl | H | tert-butyl | 4-[C(CH₃)=NOCH₃]—C₆H₄ |
| A.1383 | H | Cl | H | tert-butyl | 4-[C(CH₃)=NOEt]—C₆H₄ |
| A.1384 | H | Cl | H | tert-butyl | 2,4-F₂—C₆H₃ |
| A.1385 | H | Cl | H | tert-butyl | 2,4-Cl₂—C₆H₃ |
| A.1386 | H | Cl | H | tert-butyl | 2,4-(CH₃)₂—C₆H₃ |
| A.1387 | H | Cl | H | tert-butyl | 3,5-F₂—C₆H₃ |
| A.1388 | H | Cl | H | tert-butyl | 3,5-Cl₂—C₆H₃ |
| A.1389 | H | Cl | H | tert-butyl | 3,5-(CH₃)₂—C₆H₃ |
| A.1390 | H | Cl | H | tert-butyl | 2-F-4-Cl—C₆H₃ |
| A.1391 | H | Cl | H | tert-butyl | 2-Cl-4-F—C₆H₃ |
| A.1392 | H | Cl | H | tert-butyl | 3,4-F₂—C₆H₃ |
| A.1393 | H | Cl | H | tert-butyl | 3,4-Cl₂—C₆H₃ |
| A.1394 | H | Cl | H | tert-butyl | 2,3-F₂—C₆H₃ |
| A.1395 | H | OCH₃ | H | H | CH₃ |
| A.1396 | H | OCH₃ | H | H | ethyl |
| A.1397 | H | OCH₃ | H | H | n-propyl |
| A.1398 | H | OCH₃ | H | H | isopropyl |
| A.1399 | H | OCH₃ | H | H | tert-butyl |
| A.1400 | H | OCH₃ | H | H | n-butyl |
| A.1401 | H | OCH₃ | H | H | C₆H₅ |
| A.1402 | H | OCH₃ | H | H | 2-F—C₆H₄ |
| A.1403 | H | OCH₃ | H | H | 2-Cl—C₆H₄ |
| A.1404 | H | OCH₃ | H | H | 2-CH₃—C₆H₄ |
| A.1405 | H | OCH₃ | H | H | 2-CF₃—C₆H₄ |
| A.1406 | H | OCH₃ | H | H | 3-F—C₆H₄ |
| A.1407 | H | OCH₃ | H | H | 3-Cl—C₆H₄ |
| A.1408 | H | OCH₃ | H | H | 3-CH₃—C₆H₄ |
| A.1409 | H | OCH₃ | H | H | 3-CF₃—C₆H₄ |
| A.1410 | H | OCH₃ | H | H | 3-Br—C₆H₄ |
| A.1411 | H | OCH₃ | H | H | 4-F—C₆H₄ |
| A.1412 | H | OCH₃ | H | H | 4-Cl—C₆H₄ |
| A.1413 | H | OCH₃ | H | H | 4-CH₃—C₆H₄ |
| A.1414 | H | OCH₃ | H | H | 4-CF₃—C₆H₄ |
| A.1415 | H | OCH₃ | H | H | 4-OCH₃—C₆H₄ |
| A.1416 | H | OCH₃ | H | H | 4-OCF₃—C₆H₄ |
| A.1417 | H | OCH₃ | H | H | 4-Br—C₆H₄ |
| A.1418 | H | OCH₃ | H | H | 4-(CH=NOCH₃)—C₆H₄ |
| A.1419 | H | OCH₃ | H | H | 4-(CH=NOEt)—C₆H₄ |
| A.1420 | H | OCH₃ | H | H | 4-[C(CH₃)=NOCH₃]—C₆H₄ |
| A.1421 | H | OCH₃ | H | H | 4-[C(CH₃)=NOEt]—C₆H₄ |
| A.1422 | H | OCH₃ | H | H | 2,4-F₂—C₆H₃ |
| A.1423 | H | OCH₃ | H | H | 2,4-Cl₂—C₆H₃ |
| A.1424 | H | OCH₃ | H | H | 2,4-(CH₃)₂—C₆H₃ |
| A.1425 | H | OCH₃ | H | H | 3,5-F₂—C₆H₃ |
| A.1426 | H | OCH₃ | H | H | 3,5-Cl₂—C₆H₃ |
| A.1427 | H | OCH₃ | H | H | 3,5-(CH₃)₂—C₆H₃ |
| A.1428 | H | OCH₃ | H | H | 2-F-4-Cl—C₆H₃ |
| A.1429 | H | OCH₃ | H | H | 2-Cl-4-F—C₆H₃ |
| A.1430 | H | OCH₃ | H | H | 3,4-F₂—C₆H₃ |
| A.1431 | H | OCH₃ | H | H | 3,4-Cl₂—C₆H₃ |
| A.1432 | H | OCH₃ | H | H | 2,3-F₂—C₆H₃ |
| A.1433 | H | OCH₃ | H | CH₃ | CH₃ |
| A.1434 | H | OCH₃ | H | CH₃ | ethyl |
| A.1435 | H | OCH₃ | H | CH₃ | n-propyl |
| A.1436 | H | OCH₃ | H | CH₃ | isopropyl |
| A.1437 | H | OCH₃ | H | CH₃ | tert-butyl |
| A.1438 | H | OCH₃ | H | CH₃ | n-butyl |
| A.1439 | H | OCH₃ | H | CH₃ | C₆H₅ |
| A.1440 | H | OCH₃ | H | CH₃ | 2-F—C₆H₄ |
| A.1441 | H | OCH₃ | H | CH₃ | 2-Cl—C₆H₄ |
| A.1442 | H | OCH₃ | H | CH₃ | 2-CH₃—C₆H₄ |
| A.1443 | H | OCH₃ | H | CH₃ | 2-CF₃—C₆H₄ |
| A.1444 | H | OCH₃ | H | CH₃ | 3-F—C₆H₄ |
| A.1445 | H | OCH₃ | H | CH₃ | 3-Cl—C₆H₄ |
| A.1446 | H | OCH₃ | H | CH₃ | 3-CH₃—C₆H₄ |
| A.1447 | H | OCH₃ | H | CH₃ | 3-CF₃—C₆H₄ |
| A.1448 | H | OCH₃ | H | CH₃ | 3-Br—C₆H₄ |
| A.1449 | H | OCH₃ | H | CH₃ | 4-F—C₆H₄ |
| A.1450 | H | OCH₃ | H | CH₃ | 4-Cl—C₆H₄ |
| A.1451 | H | OCH₃ | H | CH₃ | 4-CH₃—C₆H₄ |
| A.1452 | H | OCH₃ | H | CH₃ | 4-CF₃—C₆H₄ |
| A.1453 | H | OCH₃ | H | CH₃ | 4-OCH₃—C₆H₄ |

TABLE A-continued

| No. | Y | R¹ | R² | R³ | R⁴ |
|---|---|---|---|---|---|
| A.1454 | H | OCH₃ | H | CH₃ | 4-OCF₃—C₆H₄ |
| A.1455 | H | OCH₃ | H | CH₃ | 4-Br—C₆H₄ |
| A.1456 | H | OCH₃ | H | CH₃ | 4-(CH=NOCH₃)—C₆H₄ |
| A.1457 | H | OCH₃ | H | CH₃ | 4-(CH=NOEt)—C₆H₄ |
| A.1458 | H | OCH₃ | H | CH₃ | 4-[C(CH₃)=NOCH₃]—C₆H₄ |
| A.1459 | H | OCH₃ | H | CH₃ | 4-[C(CH₃)=NOEt]—C₆H₄ |
| A.1460 | H | OCH₃ | H | CH₃ | 2,4-F₂—C₆H₃ |
| A.1461 | H | OCH₃ | H | CH₃ | 2,4-Cl₂—C₆H₃ |
| A.1462 | H | OCH₃ | H | CH₃ | 2,4-(CH₃)₂—C₆H₃ |
| A.1463 | H | OCH₃ | H | CH₃ | 3,5-F₂—C₆H₃ |
| A.1464 | H | OCH₃ | H | CH₃ | 3,5-Cl₂—C₆H₃ |
| A.1465 | H | OCH₃ | H | CH₃ | 3,5-(CH₃)₂—C₆H₃ |
| A.1466 | H | OCH₃ | H | CH₃ | 2-F-4-Cl—C₆H₃ |
| A.1467 | H | OCH₃ | H | CH₃ | 2-Cl-4-F—C₆H₃ |
| A.1468 | H | OCH₃ | H | CH₃ | 3,4-F₂—C₆H₃ |
| A.1469 | H | OCH₃ | H | CH₃ | 3,4-Cl₂—C₆H₃ |
| A.1470 | H | OCH₃ | H | CH₃ | 2,3-F₂—C₆H₃ |
| A.1471 | H | OCH₃ | H | ethyl | CH₃ |
| A.1472 | H | OCH₃ | H | ethyl | ethyl |
| A.1473 | H | OCH₃ | H | ethyl | n-propyl |
| A.1474 | H | OCH₃ | H | ethyl | isopropyl |
| A.1475 | H | OCH₃ | H | ethyl | tert-butyl |
| A.1476 | H | OCH₃ | H | ethyl | n-butyl |
| A.1477 | H | OCH₃ | H | ethyl | C₆H₅ |
| A.1478 | H | OCH₃ | H | ethyl | 2-F—C₆H₄ |
| A.1479 | H | OCH₃ | H | ethyl | 2-Cl—C₆H₄ |
| A.1480 | H | OCH₃ | H | ethyl | 2-CH₃—C₆H₄ |
| A.1481 | H | OCH₃ | H | ethyl | 2-CF₃—C₆H₄ |
| A.1482 | H | OCH₃ | H | ethyl | 3-F—C₆H₄ |
| A.1483 | H | OCH₃ | H | ethyl | 3-Cl—C₆H₄ |
| A.1484 | H | OCH₃ | H | ethyl | 3-CH₃—C₆H₄ |
| A.1485 | H | OCH₃ | H | ethyl | 3-CF₃—C₆H₄ |
| A.1486 | H | OCH₃ | H | ethyl | 3-Br—C₆H₄ |
| A.1487 | H | OCH₃ | H | ethyl | 4-F—C₆H₄ |
| A.1488 | H | OCH₃ | H | ethyl | 4-Cl—C₆H₄ |
| A.1489 | H | OCH₃ | H | ethyl | 4-CH₃—C₆H₄ |
| A.1490 | H | OCH₃ | H | ethyl | 4-CF₃—C₆H₄ |
| A.1491 | H | OCH₃ | H | ethyl | 4-OCH₃—C₆H₄ |
| A.1492 | H | OCH₃ | H | ethyl | 4-OCF₃—C₆H₄ |
| A.1493 | H | OCH₃ | H | ethyl | 4-Br—C₆H₄ |
| A.1494 | H | OCH₃ | H | ethyl | 4-(CH=NOCH₃)—C₆H₄ |
| A.1495 | H | OCH₃ | H | ethyl | 4-(CH=NOEt)—C₆H₄ |
| A.1496 | H | OCH₃ | H | ethyl | 4-[C(CH₃)=NOCH₃]—C₆H₄ |
| A.1497 | H | OCH₃ | H | ethyl | 4-[C(CH₃)=NOEt]—C₆H₄ |
| A.1498 | H | OCH₃ | H | ethyl | 2,4-F₂—C₆H₃ |
| A.1499 | H | OCH₃ | H | ethyl | 2,4-Cl₂—C₆H₃ |
| A.1500 | H | OCH₃ | H | ethyl | 2,4-(CH₃)₂—C₆H₃ |
| A.1501 | H | OCH₃ | H | ethyl | 3,5-F₂—C₆H₃ |
| A.1502 | H | OCH₃ | H | ethyl | 3,5-Cl₂—C₆H₃ |
| A.1503 | H | OCH₃ | H | ethyl | 3,5-(CH₃)₂—C₆H₃ |
| A.1504 | H | OCH₃ | H | ethyl | 2-F-4-Cl—C₆H₃ |
| A.1505 | H | OCH₃ | H | ethyl | 2-Cl-4-F—C₆H₃ |
| A.1506 | H | OCH₃ | H | ethyl | 3,4-F₂—C₆H₃ |
| A.1507 | H | OCH₃ | H | ethyl | 3,4-Cl₂—C₆H₃ |
| A.1508 | H | OCH₃ | H | ethyl | 2,3-F₂—C₆H₃ |
| A.1509 | H | OCH₃ | H | n-propyl | CH₃ |
| A.1510 | H | OCH₃ | H | n-propyl | ethyl |
| A.1511 | H | OCH₃ | H | n-propyl | n-propyl |
| A.1512 | H | OCH₃ | H | n-propyl | isopropyl |
| A.1513 | H | OCH₃ | H | n-propyl | tert-butyl |
| A.1514 | H | OCH₃ | H | n-propyl | n-butyl |
| A.1515 | H | OCH₃ | H | n-propyl | C₆H₅ |
| A.1516 | H | OCH₃ | H | n-propyl | 2-F—C₆H₄ |
| A.1517 | H | OCH₃ | H | n-propyl | 2-Cl—C₆H₄ |
| A.1518 | H | OCH₃ | H | n-propyl | 2-CH₃—C₆H₄ |
| A.1519 | H | OCH₃ | H | n-propyl | 2-CF₃—C₆H₄ |
| A.1520 | H | OCH₃ | H | n-propyl | 3-F—C₆H₄ |
| A.1521 | H | OCH₃ | H | n-propyl | 3-Cl—C₆H₄ |
| A.1522 | H | OCH₃ | H | n-propyl | 3-CH₃—C₆H₄ |
| A.1523 | H | OCH₃ | H | n-propyl | 3-CF₃—C₆H₄ |
| A.1524 | H | OCH₃ | H | n-propyl | 3-Br—C₆H₄ |
| A.1525 | H | OCH₃ | H | n-propyl | 4-F—C₆H₄ |
| A.1526 | H | OCH₃ | H | n-propyl | 4-Cl—C₆H₄ |
| A.1527 | H | OCH₃ | H | n-propyl | 4-CH₃—C₆H₄ |
| A.1528 | H | OCH₃ | H | n-propyl | 4-CF₃—C₆H₄ |
| A.1529 | H | OCH₃ | H | n-propyl | 4-OCH₃—C₆H₄ |
| A.1530 | H | OCH₃ | H | n-propyl | 4-OCF₃—C₆H₄ |

TABLE A-continued

| No. | Y | $R^1$ | $R^2$ | $R^3$ | $R^4$ |
|---|---|---|---|---|---|
| A.1531 | H | $OCH_3$ | H | n-propyl | 4-Br—$C_6H_4$ |
| A.1532 | H | $OCH_3$ | H | n-propyl | 4-(CH=$NOCH_3$)—$C_6H_4$ |
| A.1533 | H | $OCH_3$ | H | n-propyl | 4-(CH=NOEt)—$C_6H_4$ |
| A.1534 | H | $OCH_3$ | H | n-propyl | 4-[C($CH_3$)=$NOCH_3$]—$C_6H_4$ |
| A.1535 | H | $OCH_3$ | H | n-propyl | 4-[C($CH_3$)=NOEt]—$C_6H_4$ |
| A.1536 | H | $OCH_3$ | H | n-propyl | 2,4-$F_2$—$C_6H_3$ |
| A.1537 | H | $OCH_3$ | H | n-propyl | 2,4-$Cl_2$—$C_6H_3$ |
| A.1538 | H | $OCH_3$ | H | n-propyl | 2,4-$(CH_3)_2$—$C_6H_3$ |
| A.1539 | H | $OCH_3$ | H | n-propyl | 3,5-$F_2$—$C_6H_3$ |
| A.1540 | H | $OCH_3$ | H | n-propyl | 3,5-$Cl_2$—$C_6H_3$ |
| A.1541 | H | $OCH_3$ | H | n-propyl | 3,5-$(CH_3)_2$—$C_6H_3$ |
| A.1542 | H | $OCH_3$ | H | n-propyl | 2-F-4-Cl—$C_6H_3$ |
| A.1543 | H | $OCH_3$ | H | n-propyl | 2-Cl-4-F—$C_6H_3$ |
| A.1544 | H | $OCH_3$ | H | n-propyl | 3,4-$F_2$—$C_6H_3$ |
| A.1545 | H | $OCH_3$ | H | n-propyl | 3,4-$Cl_2$—$C_6H_3$ |
| A.1546 | H | $OCH_3$ | H | n-propyl | 2,3-$F_2$—$C_6H_3$ |
| A.1547 | H | $OCH_3$ | H | n-propyl | $CH_3$ |
| A.1548 | H | $OCH_3$ | H | n-propyl | ethyl |
| A.1549 | H | $OCH_3$ | H | n-propyl | n-propyl |
| A.1550 | H | $OCH_3$ | H | n-propyl | isopropyl |
| A.1551 | H | $OCH_3$ | H | n-propyl | tert-butyl |
| A.1552 | H | $OCH_3$ | H | n-propyl | n-butyl |
| A.1553 | H | $OCH_3$ | H | n-propyl | $C_6H_5$ |
| A.1554 | H | $OCH_3$ | H | n-propyl | 2-F—$C_6H_4$ |
| A.1555 | H | $OCH_3$ | H | n-propyl | 2-Cl—$C_6H_4$ |
| A.1556 | H | $OCH_3$ | H | n-propyl | 2-$CH_3$—$C_6H_4$ |
| A.1557 | H | $OCH_3$ | H | n-propyl | 2-$CF_3$—$C_6H_4$ |
| A.1558 | H | $OCH_3$ | H | n-propyl | 3-F—$C_6H_4$ |
| A.1559 | H | $OCH_3$ | H | n-propyl | 3-Cl—$C_6H_4$ |
| A.1560 | H | $OCH_3$ | H | n-propyl | 3-$CH_3$—$C_6H_4$ |
| A.1561 | H | $OCH_3$ | H | n-propyl | 3-$CF_3$—$C_6H_4$ |
| A.1562 | H | $OCH_3$ | H | n-propyl | 3-Br—$C_6H_4$ |
| A.1563 | H | $OCH_3$ | H | n-propyl | 4-F—$C_6H_4$ |
| A.1564 | H | $OCH_3$ | H | n-propyl | 4-Cl—$C_6H_4$ |
| A.1565 | H | $OCH_3$ | H | n-propyl | 4-$CH_3$—$C_6H_4$ |
| A.1566 | H | $OCH_3$ | H | n-propyl | 4-$CF_3$—$C_6H_4$ |
| A.1567 | H | $OCH_3$ | H | n-propyl | 4-$OCH_3$—$C_6H_4$ |
| A.1568 | H | $OCH_3$ | H | n-propyl | 4-$OCF_3$—$C_6H_4$ |
| A.1569 | H | $OCH_3$ | H | n-propyl | 4-Br—$C_6H_4$ |
| A.1570 | H | $OCH_3$ | H | n-propyl | 4-(CH=$NOCH_3$)—$C_6H_4$ |
| A.1571 | H | $OCH_3$ | H | n-propyl | 4-(CH=NOEt)—$C_6H_4$ |
| A.1572 | H | $OCH_3$ | H | n-propyl | 4-[C($CH_3$)=$NOCH_3$]—$C_6H_4$ |
| A.1573 | H | $OCH_3$ | H | n-propyl | 4-[C($CH_3$)=NOEt]—$C_6H_4$ |
| A.1574 | H | $OCH_3$ | H | n-propyl | 2,4-$F_2$—$C_6H_3$ |
| A.1575 | H | $OCH_3$ | H | n-propyl | 2,4-$Cl_2$—$C_6H_3$ |
| A.1576 | H | $OCH_3$ | H | n-propyl | 2,4-$(CH_3)_2$—$C_6H_3$ |
| A.1577 | H | $OCH_3$ | H | n-propyl | 3,5-$F_2$—$C_6H_3$ |
| A.1578 | H | $OCH_3$ | H | n-propyl | 3,5-$Cl_2$—$C_6H_3$ |
| A.1579 | H | $OCH_3$ | H | n-propyl | 3,5-$(CH_3)_2$—$C_6H_3$ |
| A.1580 | H | $OCH_3$ | H | n-propyl | 2-F-4-Cl—$C_6H_3$ |
| A.1581 | H | $OCH_3$ | H | n-propyl | 2-Cl-4-F—$C_6H_3$ |
| A.1582 | H | $OCH_3$ | H | n-propyl | 3,4-$F_2$—$C_6H_3$ |
| A.1583 | H | $OCH_3$ | H | n-propyl | 3,4-$Cl_2$—$C_6H_3$ |
| A.1584 | H | $OCH_3$ | H | n-propyl | 2,3-$F_2$—$C_6H_3$ |
| A.1585 | H | $OCH_3$ | H | n-butyl | $CH_3$ |
| A.1586 | H | $OCH_3$ | H | n-butyl | ethyl |
| A.1587 | H | $OCH_3$ | H | n-butyl | n-propyl |
| A.1588 | H | $OCH_3$ | H | n-butyl | isopropyl |
| A.1589 | H | $OCH_3$ | H | n-butyl | tert-butyl |
| A.1590 | H | $OCH_3$ | H | n-butyl | n-butyl |
| A.1591 | H | $OCH_3$ | H | n-butyl | $C_6H_5$ |
| A.1592 | H | $OCH_3$ | H | n-butyl | 2-F—$C_6H_4$ |
| A.1593 | H | $OCH_3$ | H | n-butyl | 2-Cl—$C_6H_4$ |
| A.1594 | H | $OCH_3$ | H | n-butyl | 2-$CH_3$—$C_6H_4$ |
| A.1595 | H | $OCH_3$ | H | n-butyl | 2-$CF_3$—$C_6H_4$ |
| A.1596 | H | $OCH_3$ | H | n-butyl | 3-F—$C_6H_4$ |
| A.1597 | H | $OCH_3$ | H | n-butyl | 3-Cl—$C_6H_4$ |
| A.1598 | H | $OCH_3$ | H | n-butyl | 3-$CH_3$—$C_6H_4$ |
| A.1599 | H | $OCH_3$ | H | n-butyl | 3-$CF_3$—$C_6H_4$ |
| A.1600 | H | $OCH_3$ | H | n-butyl | 3-Br—$C_6H_4$ |
| A.1601 | H | $OCH_3$ | H | n-butyl | 4-F—$C_6H_4$ |
| A.1602 | H | $OCH_3$ | H | n-butyl | 4-Cl—$C_6H_4$ |
| A.1603 | H | $OCH_3$ | H | n-butyl | 4-$CH_3$—$C_6H_4$ |
| A.1604 | H | $OCH_3$ | H | n-butyl | 4-$CF_3$—$C_6H_4$ |
| A.1605 | H | $OCH_3$ | H | n-butyl | 4-$OCH_3$—$C_6H_4$ |
| A.1606 | H | $OCH_3$ | H | n-butyl | 4-$OCF_3$—$C_6H_4$ |
| A.1607 | H | $OCH_3$ | H | n-butyl | 4-Br—$C_6H_4$ |

TABLE A-continued

| No. | Y | R$^1$ | R$^2$ | R$^3$ | R$^4$ |
|---|---|---|---|---|---|
| A.1608 | H | OCH$_3$ | H | n-butyl | 4-(CH=NOCH$_3$)—C$_6$H$_4$ |
| A.1609 | H | OCH$_3$ | H | n-butyl | 4-(CH=NOEt)—C$_6$H$_4$ |
| A.1610 | H | OCH$_3$ | H | n-butyl | 4-[C(CH$_3$)=NOCH$_3$]—C$_6$H$_4$ |
| A.1611 | H | OCH$_3$ | H | n-butyl | 4-[C(CH$_3$)=NOEt]—C$_6$H$_4$ |
| A.1612 | H | OCH$_3$ | H | n-butyl | 2,4-F$_2$—C$_6$H$_3$ |
| A.1613 | H | OCH$_3$ | H | n-butyl | 2,4-Cl$_2$—C$_6$H$_3$ |
| A.1614 | H | OCH$_3$ | H | n-butyl | 2,4-(CH$_3$)$_2$—C$_6$H$_3$ |
| A.1615 | H | OCH$_3$ | H | n-butyl | 3,5-F$_2$—C$_6$H$_3$ |
| A.1616 | H | OCH$_3$ | H | n-butyl | 3,5-Cl$_2$—C$_6$H$_3$ |
| A.1617 | H | OCH$_3$ | H | n-butyl | 3,5-(CH$_3$)$_2$—C$_6$H$_3$ |
| A.1618 | H | OCH$_3$ | H | n-butyl | 2-F-4-Cl—C$_6$H$_3$ |
| A.1619 | H | OCH$_3$ | H | n-butyl | 2-Cl-4-F—C$_6$H$_3$ |
| A.1620 | H | OCH$_3$ | H | n-butyl | 3,4-F$_2$—C$_6$H$_3$ |
| A.1621 | H | OCH$_3$ | H | n-butyl | 3,4-Cl$_2$—C$_6$H$_3$ |
| A.1622 | H | OCH$_3$ | H | n-butyl | 2,3-F$_2$—C$_6$H$_3$ |
| A.1623 | H | OCH$_3$ | H | n-butyl | CH$_3$ |
| A.1624 | H | OCH$_3$ | H | n-butyl | ethyl |
| A.1625 | H | OCH$_3$ | H | n-butyl | n-propyl |
| A.1626 | H | OCH$_3$ | H | n-butyl | isopropyl |
| A.1627 | H | OCH$_3$ | H | n-butyl | tert-butyl |
| A.1628 | H | OCH$_3$ | H | n-butyl | n-butyl |
| A.1629 | H | OCH$_3$ | H | n-butyl | C$_6$H$_5$ |
| A.1630 | H | OCH$_3$ | H | n-butyl | 2-F—C$_6$H$_4$ |
| A.1631 | H | OCH$_3$ | H | n-butyl | 2-Cl—C$_6$H$_4$ |
| A.1632 | H | OCH$_3$ | H | n-butyl | 2-CH$_3$—C$_6$H$_4$ |
| A.1633 | H | OCH$_3$ | H | n-butyl | 2-CF$_3$—C$_6$H$_4$ |
| A.1634 | H | OCH$_3$ | H | n-butyl | 3-F—C$_6$H$_4$ |
| A.1635 | H | OCH$_3$ | H | n-butyl | 3-Cl—C$_6$H$_4$ |
| A.1636 | H | OCH$_3$ | H | n-butyl | 3-CH$_3$—C$_6$H$_4$ |
| A.1637 | H | OCH$_3$ | H | n-butyl | 3-CF$_3$—C$_6$H$_4$ |
| A.1638 | H | OCH$_3$ | H | n-butyl | 3-Br—C$_6$H$_4$ |
| A.1639 | H | OCH$_3$ | H | n-butyl | 4-F—C$_6$H$_4$ |
| A.1640 | H | OCH$_3$ | H | n-butyl | 4-Cl—C$_6$H$_4$ |
| A.1641 | H | OCH$_3$ | H | n-butyl | 4-CH$_3$—C$_6$H$_4$ |
| A.1642 | H | OCH$_3$ | H | n-butyl | 4-CF$_3$—C$_6$H$_4$ |
| A.1643 | H | OCH$_3$ | H | n-butyl | 4-OCH$_3$—C$_6$H$_4$ |
| A.1644 | H | OCH$_3$ | H | n-butyl | 4-OCF$_3$—C$_6$H$_4$ |
| A.1645 | H | OCH$_3$ | H | n-butyl | 4-Br—C$_6$H$_4$ |
| A.1646 | H | OCH$_3$ | H | n-butyl | 4-(CH=NOCH$_3$)—C$_6$H$_4$ |
| A.1647 | H | OCH$_3$ | H | n-butyl | 4-(CH=NOEt)—C$_6$H$_4$ |
| A.1648 | H | OCH$_3$ | H | n-butyl | 4-[C(CH$_3$)=NOCH$_3$]—C$_6$H$_4$ |
| A.1649 | H | OCH$_3$ | H | n-butyl | 4-[C(CH$_3$)=NOEt]—C$_6$H$_4$ |
| A.1650 | H | OCH$_3$ | H | n-butyl | 2,4-F$_2$—C$_6$H$_3$ |
| A.1651 | H | OCH$_3$ | H | n-butyl | 2,4-Cl$_2$—C$_6$H$_3$ |
| A.1652 | H | OCH$_3$ | H | n-butyl | 2,4-(CH$_3$)$_2$—C$_6$H$_3$ |
| A.1653 | H | OCH$_3$ | H | n-butyl | 3,5-F$_2$—C$_6$H$_3$ |
| A.1654 | H | OCH$_3$ | H | n-butyl | 3,5-Cl$_2$—C$_6$H$_3$ |
| A.1655 | H | OCH$_3$ | H | n-butyl | 3,5-(CH$_3$)$_2$—C$_6$H$_3$ |
| A.1656 | H | OCH$_3$ | H | n-butyl | 2-F-4-Cl—C$_6$H$_3$ |
| A.1657 | H | OCH$_3$ | H | n-butyl | 2-Cl-4-F—C$_6$H$_3$ |
| A.1658 | H | OCH$_3$ | H | n-butyl | 3,4-F$_2$—C$_6$H$_3$ |
| A.1659 | H | OCH$_3$ | H | n-butyl | 3,4-Cl$_2$—C$_6$H$_3$ |
| A.1660 | H | OCH$_3$ | H | n-butyl | 2,3-F$_2$—C$_6$H$_3$ |
| A.1661 | H | OCH$_3$ | H | isopropyl | CH$_3$ |
| A.1662 | H | OCH$_3$ | H | isopropyl | ethyl |
| A.1663 | H | OCH$_3$ | H | isopropyl | n-propyl |
| A.1664 | H | OCH$_3$ | H | isopropyl | isopropyl |
| A.1665 | H | OCH$_3$ | H | isopropyl | tert-butyl |
| A.1666 | H | OCH$_3$ | H | isopropyl | n-butyl |
| A.1667 | H | OCH$_3$ | H | isopropyl | C$_6$H$_5$ |
| A.1668 | H | OCH$_3$ | H | isopropyl | 2-F—C$_6$H$_4$ |
| A.1669 | H | OCH$_3$ | H | isopropyl | 2-Cl—C$_6$H$_4$ |
| A.1670 | H | OCH$_3$ | H | isopropyl | 2-CH$_3$—C$_6$H$_4$ |
| A.1671 | H | OCH$_3$ | H | isopropyl | 2-CF$_3$—C$_6$H$_4$ |
| A.1672 | H | OCH$_3$ | H | isopropyl | 3-F—C$_6$H$_4$ |
| A.1673 | H | OCH$_3$ | H | isopropyl | 3-Cl—C$_6$H$_4$ |
| A.1674 | H | OCH$_3$ | H | isopropyl | 3-CH$_3$—C$_6$H$_4$ |
| A.1675 | H | OCH$_3$ | H | isopropyl | 3-CF$_3$—C$_6$H$_4$ |
| A.1676 | H | OCH$_3$ | H | isopropyl | 3-Br—C$_6$H$_4$ |
| A.1677 | H | OCH$_3$ | H | isopropyl | 4-F—C$_6$H$_4$ |
| A.1678 | H | OCH$_3$ | H | isopropyl | 4-Cl—C$_6$H$_4$ |
| A.1679 | H | OCH$_3$ | H | isopropyl | 4-CH$_3$—C$_6$H$_4$ |
| A.1680 | H | OCH$_3$ | H | isopropyl | 4-CF$_3$—C$_6$H$_4$ |
| A.1681 | H | OCH$_3$ | H | isopropyl | 4-OCH$_3$—C$_6$H$_4$ |
| A.1682 | H | OCH$_3$ | H | isopropyl | 4-OCF$_3$—C$_6$H$_4$ |
| A.1683 | H | OCH$_3$ | H | isopropyl | 4-Br—C$_6$H$_4$ |
| A.1684 | H | OCH$_3$ | H | isopropyl | 4-(CH=NOCH$_3$)—C$_6$H$_4$ |

TABLE A-continued

| No. | Y | R¹ | R² | R³ | R⁴ |
|---|---|---|---|---|---|
| A.1685 | H | OCH₃ | H | isopropyl | 4-(CH=NOEt)—C₆H₄ |
| A.1686 | H | OCH₃ | H | isopropyl | 4-[C(CH₃)=NOCH₃]—C₆H₄ |
| A.1687 | H | OCH₃ | H | isopropyl | 4-[C(CH₃)=NOEt]—C₆H₄ |
| A.1688 | H | OCH₃ | H | isopropyl | 2,4-F₂—C₆H₃ |
| A.1689 | H | OCH₃ | H | isopropyl | 2,4-Cl₂—C₆H₃ |
| A.1690 | H | OCH₃ | H | isopropyl | 2,4-(CH₃)₂—C₆H₃ |
| A.1691 | H | OCH₃ | H | isopropyl | 3,5-F₂—C₆H₃ |
| A.1692 | H | OCH₃ | H | isopropyl | 3,5-Cl₂—C₆H₃ |
| A.1693 | H | OCH₃ | H | isopropyl | 3,5-(CH₃)₂—C₆H₃ |
| A.1694 | H | OCH₃ | H | isopropyl | 2-F-4-Cl—C₆H₃ |
| A.1695 | H | OCH₃ | H | isopropyl | 2-Cl-4-F—C₆H₃ |
| A.1696 | H | OCH₃ | H | isopropyl | 3,4-F₂—C₆H₃ |
| A.1697 | H | OCH₃ | H | isopropyl | 3,4-Cl₂—C₆H₃ |
| A.1698 | H | OCH₃ | H | isopropyl | 2,3-F₂—C₆H₃ |
| A.1699 | H | OCH₃ | H | isopropyl | CH₃ |
| A.1700 | H | OCH₃ | H | isopropyl | ethyl |
| A.1701 | H | OCH₃ | H | isopropyl | n-propyl |
| A.1702 | H | OCH₃ | H | isopropyl | isopropyl |
| A.1703 | H | OCH₃ | H | isopropyl | tert-butyl |
| A.1704 | H | OCH₃ | H | isopropyl | n-butyl |
| A.1705 | H | OCH₃ | H | isopropyl | C₆H₅ |
| A.1706 | H | OCH₃ | H | isopropyl | 2-F—C₆H₄ |
| A.1707 | H | OCH₃ | H | isopropyl | 2-Cl—C₆H₄ |
| A.1708 | H | OCH₃ | H | isopropyl | 2-CH₃—C₆H₄ |
| A.1709 | H | OCH₃ | H | isopropyl | 2-CF₃—C₆H₄ |
| A.1710 | H | OCH₃ | H | isopropyl | 3-F—C₆H₄ |
| A.1711 | H | OCH₃ | H | isopropyl | 3-Cl—C₆H₄ |
| A.1712 | H | OCH₃ | H | isopropyl | 3-CH₃—C₆H₄ |
| A.1713 | H | OCH₃ | H | isopropyl | 3-CF₃—C₆H₄ |
| A.1714 | H | OCH₃ | H | isopropyl | 3-Br—C₆H₄ |
| A.1715 | H | OCH₃ | H | isopropyl | 4-F—C₆H₄ |
| A.1716 | H | OCH₃ | H | isopropyl | 4-Cl—C₆H₄ |
| A.1717 | H | OCH₃ | H | isopropyl | 4-CH₃—C₆H₄ |
| A.1718 | H | OCH₃ | H | isopropyl | 4-CF₃—C₆H₄ |
| A.1719 | H | OCH₃ | H | isopropyl | 4-OCH₃—C₆H₄ |
| A.1720 | H | OCH₃ | H | isopropyl | 4-OCF₃—C₆H₄ |
| A.1721 | H | OCH₃ | H | isopropyl | 4-Br—C₆H₄ |
| A.1722 | H | OCH₃ | H | isopropyl | 4-(CH=NOCH₃)—C₆H₄ |
| A.1723 | H | OCH₃ | H | isopropyl | 4-(CH=NOEt)—C₆H₄ |
| A.1724 | H | OCH₃ | H | isopropyl | 4-[C(CH₃)=NOCH₃]—C₆H₄ |
| A.1725 | H | OCH₃ | H | isopropyl | 4-[C(CH₃)=NOEt]—C₆H₄ |
| A.1726 | H | OCH₃ | H | isopropyl | 2,4-F₂—C₆H₃ |
| A.1727 | H | OCH₃ | H | isopropyl | 2,4-Cl₂—C₆H₃ |
| A.1728 | H | OCH₃ | H | isopropyl | 2,4-(CH₃)₂—C₆H₃ |
| A.1729 | H | OCH₃ | H | isopropyl | 3,5-F₂—C₆H₃ |
| A.1730 | H | OCH₃ | H | isopropyl | 3,5-Cl₂—C₆H₃ |
| A.1731 | H | OCH₃ | H | isopropyl | 3,5-(CH₃)₂—C₆H₃ |
| A.1732 | H | OCH₃ | H | isopropyl | 2-F-4-Cl—C₆H₃ |
| A.1733 | H | OCH₃ | H | isopropyl | 2-Cl-4-F—C₆H₃ |
| A.1734 | H | OCH₃ | H | isopropyl | 3,4-F₂—C₆H₃ |
| A.1735 | H | OCH₃ | H | isopropyl | 3,4-Cl₂—C₆H₃ |
| A.1736 | H | OCH₃ | H | isopropyl | 2,3-F₂—C₆H₃ |
| A.1737 | H | OCH₃ | H | tert-butyl | CH₃ |
| A.1738 | H | OCH₃ | H | tert-butyl | ethyl |
| A.1739 | H | OCH₃ | H | tert-butyl | n-propyl |
| A.1740 | H | OCH₃ | H | tert-butyl | isopropyl |
| A.1741 | H | OCH₃ | H | tert-butyl | tert-butyl |
| A.1742 | H | OCH₃ | H | tert-butyl | n-butyl |
| A.1743 | H | OCH₃ | H | tert-butyl | C₆H₅ |
| A.1744 | H | OCH₃ | H | tert-butyl | 2-F—C₆H₄ |
| A.1745 | H | OCH₃ | H | tert-butyl | 2-Cl—C₆H₄ |
| A.1746 | H | OCH₃ | H | tert-butyl | 2-CH₃—C₆H₄ |
| A.1747 | H | OCH₃ | H | tert-butyl | 2-CF₃—C₆H₄ |
| A.1748 | H | OCH₃ | H | tert-butyl | 3-F—C₆H₄ |
| A.1749 | H | OCH₃ | H | tert-butyl | 3-Cl—C₆H₄ |
| A.1750 | H | OCH₃ | H | tert-butyl | 3-CH₃—C₆H₄ |
| A.1751 | H | OCH₃ | H | tert-butyl | 3-CF₃—C₆H₄ |
| A.1752 | H | OCH₃ | H | tert-butyl | 3-Br—C₆H₄ |
| A.1753 | H | OCH₃ | H | tert-butyl | 4-F—C₆H₄ |
| A.1754 | H | OCH₃ | H | tert-butyl | 4-Cl—C₆H₄ |
| A.1755 | H | OCH₃ | H | tert-butyl | 4-CH₃—C₆H₄ |
| A.1756 | H | OCH₃ | H | tert-butyl | 4-CF₃—C₆H₄ |
| A.1757 | H | OCH₃ | H | tert-butyl | 4-OCH₃—C₆H₄ |
| A.1758 | H | OCH₃ | H | tert-butyl | 4-OCF₃—C₆H₄ |
| A.1759 | H | OCH₃ | H | tert-butyl | 4-Br—C₆H₄ |
| A.1760 | H | OCH₃ | H | tert-butyl | 4-(CH=NOCH₃)—C₆H₄ |
| A.1761 | H | OCH₃ | H | tert-butyl | 4-(CH=NOEt)—C₆H₄ |

TABLE A-continued

| No. | Y | R¹ | R² | R³ | R⁴ |
|---|---|---|---|---|---|
| A.1762 | H | OCH₃ | H | tert-butyl | 4-[C(CH₃)=NOCH₃]—C₆H₄ |
| A.1763 | H | OCH₃ | H | tert-butyl | 4-[C(CH₃)=NOEt]—C₆H₄ |
| A.1764 | H | OCH₃ | H | tert-butyl | 2,4-F₂—C₆H₃ |
| A.1765 | H | OCH₃ | H | tert-butyl | 2,4-Cl₂—C₆H₃ |
| A.1766 | H | OCH₃ | H | tert-butyl | 2,4-(CH₃)₂—C₆H₃ |
| A.1767 | H | OCH₃ | H | tert-butyl | 3,5-F₂—C₆H₃ |
| A.1768 | H | OCH₃ | H | tert-butyl | 3,5-Cl₂—C₆H₃ |
| A.1769 | H | OCH₃ | H | tert-butyl | 3,5-(CH₃)₂—C₆H₃ |
| A.1770 | H | OCH₃ | H | tert-butyl | 2-F-4-Cl—C₆H₃ |
| A.1771 | H | OCH₃ | H | tert-butyl | 2-Cl-4-F—C₆H₃ |
| A.1772 | H | OCH₃ | H | tert-butyl | 3,4-F₂—C₆H₃ |
| A.1773 | H | OCH₃ | H | tert-butyl | 3,4-Cl₂—C₆H₃ |
| A.1774 | H | OCH₃ | H | tert-butyl | 2,3-F₂—C₆H₃ |
| A.1775 | H | OCH₃ | H | tert-butyl | CH₃ |
| A.1776 | H | OCH₃ | H | tert-butyl | ethyl |
| A.1777 | H | OCH₃ | H | tert-butyl | n-propyl |
| A.1778 | H | OCH₃ | H | tert-butyl | isopropyl |
| A.1779 | H | OCH₃ | H | tert-butyl | tert-butyl |
| A.1780 | H | OCH₃ | H | tert-butyl | n-butyl |
| A.1781 | H | OCH₃ | H | tert-butyl | C₆H₅ |
| A.1782 | H | OCH₃ | H | tert-butyl | 2-F—C₆H₄ |
| A.1783 | H | OCH₃ | H | tert-butyl | 2-Cl—C₆H₄ |
| A.1784 | H | OCH₃ | H | tert-butyl | 2-CH₃—C₆H₄ |
| A.1785 | H | OCH₃ | H | tert-butyl | 2-CF₃—C₆H₄ |
| A.1786 | H | OCH₃ | H | tert-butyl | 3-F—C₆H₄ |
| A.1787 | H | OCH₃ | H | tert-butyl | 3-Cl—C₆H₄ |
| A.1788 | H | OCH₃ | H | tert-butyl | 3-CH₃—C₆H₄ |
| A.1789 | H | OCH₃ | H | tert-butyl | 3-CF₃—C₆H₄ |
| A.1790 | H | OCH₃ | H | tert-butyl | 3-Br—C₆H₄ |
| A.1791 | H | OCH₃ | H | tert-butyl | 4-F—C₆H₄ |
| A.1792 | H | OCH₃ | H | tert-butyl | 4-Cl—C₆H₄ |
| A.1793 | H | OCH₃ | H | tert-butyl | 4-CH₃—C₆H₄ |
| A.1794 | H | OCH₃ | H | tert-butyl | 4-CF₃—C₆H₄ |
| A.1795 | H | OCH₃ | H | tert-butyl | 4-OCH₃—C₆H₄ |
| A.1796 | H | OCH₃ | H | tert-butyl | 4-OCF₃—C₆H₄ |
| A.1797 | H | OCH₃ | H | tert-butyl | 4-Br—C₆H₄ |
| A.1798 | H | OCH₃ | H | tert-butyl | 4-(CH=NOCH₃)—C₆H₄ |
| A.1799 | H | OCH₃ | H | tert-butyl | 4-(CH=NOEt)—C₆H₄ |
| A.1800 | H | OCH₃ | H | tert-butyl | 4-[C(CH₃)=NOCH₃]—C₆H₄ |
| A.1801 | H | OCH₃ | H | tert-butyl | 4-[C(CH₃)=NOEt]—C₆H₄ |
| A.1802 | H | OCH₃ | H | tert-butyl | 2,4-F₂—C₆H₃ |
| A.1803 | H | OCH₃ | H | tert-butyl | 2,4-Cl₂—C₆H₃ |
| A.1804 | H | OCH₃ | H | tert-butyl | 2,4-(CH₃)₂—C₆H₃ |
| A.1805 | H | OCH₃ | H | tert-butyl | 3,5-F₂—C₆H₃ |
| A.1806 | H | OCH₃ | H | tert-butyl | 3,5-Cl₂—C₆H₃ |
| A.1807 | H | OCH₃ | H | tert-butyl | 3,5-(CH₃)₂—C₆H₃ |
| A.1808 | H | OCH₃ | H | tert-butyl | 2-F-4-Cl—C₆H₃ |
| A.1809 | H | OCH₃ | H | tert-butyl | 2-Cl-4-F—C₆H₃ |
| A.1810 | H | OCH₃ | H | tert-butyl | 3,4-F₂—C₆H₃ |
| A.1811 | H | OCH₃ | H | tert-butyl | 3,4-Cl₂—C₆H₃ |
| A.1812 | H | OCH₃ | H | tert-butyl | 2,3-F₂—C₆H₃ |
| A.1813 | H | CF₃ | H | H | C₆H₅ |
| A.1814 | H | CF₃ | H | CH₃ | C₆H₅ |
| A.1815 | H | CF₃ | H | ethyl | C₆H₅ |
| A.1816 | H | CF₃ | H | n-propyl | C₆H₅ |
| A.1817 | H | CF₃ | H | n-butyl | C₆H₅ |
| A.1818 | H | CF₃ | H | isopropyl | C₆H₅ |
| A.1819 | H | CF₃ | H | tert-butyl | C₆H₅ |
| A.1820 | H | CF₃ | H | H | 4-F—C₆H₄ |
| A.1821 | H | CF₃ | H | CH₃ | 4-F—C₆H₄ |
| A.1822 | H | CF₃ | H | ethyl | 4-F—C₆H₄ |
| A.1823 | H | CF₃ | H | n-propyl | 4-F—C₆H₄ |
| A.1824 | H | CF₃ | H | n-butyl | 4-F—C₆H₄ |
| A.1825 | H | CF₃ | H | isopropyl | 4-F—C₆H₄ |
| A.1826 | H | CF₃ | H | tert-butyl | 4-F—C₆H₄ |
| A.1827 | H | CH₃ | CH₃ | CH₃ | CH₃ |
| A.1828 | H | CH₃ | CH₃ | CH₃ | ethyl |
| A.1829 | H | CH₃ | CH₃ | CH₃ | n-propyl |
| A.1830 | H | CH₃ | CH₃ | CH₃ | isopropyl |
| A.1831 | H | CH₃ | CH₃ | CH₃ | tert-butyl |
| A.1832 | H | CH₃ | CH₃ | CH₃ | n-butyl |
| A.1833 | H | CH₃ | CH₃ | CH₃ | C₆H₅ |
| A.1834 | H | CH₃ | CH₃ | CH₃ | 2-F—C₆H₄ |
| A.1835 | H | CH₃ | CH₃ | CH₃ | 2-Cl—C₆H₄ |
| A.1836 | H | CH₃ | CH₃ | CH₃ | 2-CH₃—C₆H₄ |
| A.1837 | H | CH₃ | CH₃ | CH₃ | 2-CF₃—C₆H₄ |
| A.1838 | H | CH₃ | CH₃ | CH₃ | 3-F—C₆H₄ |

TABLE A-continued

| No. | Y | R¹ | R² | R³ | R⁴ |
|---|---|---|---|---|---|
| A.1839 | H | CH₃ | CH₃ | CH₃ | 3-Cl—C₆H₄ |
| A.1840 | H | CH₃ | CH₃ | CH₃ | 3-CH₃—C₆H₄ |
| A.1841 | H | CH₃ | CH₃ | CH₃ | 3-CF₃—C₆H₄ |
| A.1842 | H | CH₃ | CH₃ | CH₃ | 3-Br—C₆H₄ |
| A.1843 | H | CH₃ | CH₃ | CH₃ | 4-F—C₆H₄ |
| A.1844 | H | CH₃ | CH₃ | CH₃ | 4-Cl—C₆H₄ |
| A.1845 | H | CH₃ | CH₃ | CH₃ | 4-CH₃—C₆H₄ |
| A.1846 | H | CH₃ | CH₃ | CH₃ | 4-CF₃—C₆H₄ |
| A.1847 | H | CH₃ | CH₃ | CH₃ | 4-OCH₃—C₆H₄ |
| A.1848 | H | CH₃ | CH₃ | CH₃ | 4-OCF₃—C₆H₄ |
| A.1849 | H | CH₃ | CH₃ | CH₃ | 4-Br—C₆H₄ |
| A.1850 | H | CH₃ | CH₃ | CH₃ | 4-(CH=NOCH₃)—C₆H₄ |
| A.1851 | H | CH₃ | CH₃ | CH₃ | 4-(CH=NOEt)—C₆H₄ |
| A.1852 | H | CH₃ | CH₃ | CH₃ | 4-[C(CH₃)=NOCH₃]—C₆H₄ |
| A.1853 | H | CH₃ | CH₃ | CH₃ | 4-[C(CH₃)=NOEt]—C₆H₄ |
| A.1854 | H | CH₃ | CH₃ | CH₃ | 2,4-F₂—C₆H₃ |
| A.1855 | H | CH₃ | CH₃ | CH₃ | 2,4-Cl₂—C₆H₃ |
| A.1856 | H | CH₃ | CH₃ | CH₃ | 2,4-(CH₃)₂—C₆H₃ |
| A.1857 | H | CH₃ | CH₃ | CH₃ | 3,5-F₂—C₆H₃ |
| A.1858 | H | CH₃ | CH₃ | CH₃ | 3,5-Cl₂—C₆H₃ |
| A.1859 | H | CH₃ | CH₃ | CH₃ | 3,5-(CH₃)₂—C₆H₃ |
| A.1860 | H | CH₃ | CH₃ | CH₃ | 2-F-4-Cl—C₆H₃ |
| A.1861 | H | CH₃ | CH₃ | CH₃ | 2-Cl-4-F—C₆H₃ |
| A.1862 | H | CH₃ | CH₃ | CH₃ | 3,4-F₂—C₆H₃ |
| A.1863 | H | CH₃ | CH₃ | CH₃ | 3,4-Cl₂—C₆H₃ |
| A.1864 | H | CH₃ | CH₃ | CH₃ | 2,3-F₂—C₆H₃ |
| A.1865 | H | CH₃ | CH₃ | ethyl | CH₃ |
| A.1866 | H | CH₃ | CH₃ | ethyl | ethyl |
| A.1867 | H | CH₃ | CH₃ | ethyl | n-propyl |
| A.1868 | H | CH₃ | CH₃ | ethyl | isopropyl |
| A.1869 | H | CH₃ | CH₃ | ethyl | tert-butyl |
| A.1870 | H | CH₃ | CH₃ | ethyl | n-butyl |
| A.1871 | H | CH₃ | CH₃ | ethyl | C₆H₅ |
| A.1872 | H | CH₃ | CH₃ | ethyl | 2-F—C₆H₄ |
| A.1873 | H | CH₃ | CH₃ | ethyl | 2-Cl—C₆H₄ |
| A.1874 | H | CH₃ | CH₃ | ethyl | 2-CH₃—C₆H₄ |
| A.1875 | H | CH₃ | CH₃ | ethyl | 2-CF₃—C₆H₄ |
| A.1876 | H | CH₃ | CH₃ | ethyl | 3-F—C₆H₄ |
| A.1877 | H | CH₃ | CH₃ | ethyl | 3-Cl—C₆H₄ |
| A.1878 | H | CH₃ | CH₃ | ethyl | 3-CH₃—C₆H₄ |
| A.1879 | H | CH₃ | CH₃ | ethyl | 3-CF₃—C₆H₄ |
| A.1880 | H | CH₃ | CH₃ | ethyl | 3-Br—C₆H₄ |
| A.1881 | H | CH₃ | CH₃ | ethyl | 4-F—C₆H₄ |
| A.1882 | H | CH₃ | CH₃ | ethyl | 4-Cl—C₆H₄ |
| A.1883 | H | CH₃ | CH₃ | ethyl | 4-CH₃—C₆H₄ |
| A.1884 | H | CH₃ | CH₃ | ethyl | 4-CF₃—C₆H₄ |
| A.1885 | H | CH₃ | CH₃ | ethyl | 4-OCH₃—C₆H₄ |
| A.1886 | H | CH₃ | CH₃ | ethyl | 4-OCF₃—C₆H₄ |
| A.1887 | H | CH₃ | CH₃ | ethyl | 4-Br—C₆H₄ |
| A.1888 | H | CH₃ | CH₃ | ethyl | 4-(CH=NOCH₃)—C₆H₄ |
| A.1889 | H | CH₃ | CH₃ | ethyl | 4-(CH=NOEt)—C₆H₄ |
| A.1890 | H | CH₃ | CH₃ | ethyl | 4-[C(CH₃)=NOCH₃]—C₆H₄ |
| A.1891 | H | CH₃ | CH₃ | ethyl | 4-[C(CH₃)=NOEt]—C₆H₄ |
| A.1892 | H | CH₃ | CH₃ | ethyl | 2,4-F₂—C₆H₃ |
| A.1893 | H | CH₃ | CH₃ | ethyl | 2,4-Cl₂—C₆H₃ |
| A.1894 | H | CH₃ | CH₃ | ethyl | 2,4-(CH₃)₂—C₆H₃ |
| A.1895 | H | CH₃ | CH₃ | ethyl | 3,5-F₂—C₆H₃ |
| A.1896 | H | CH₃ | CH₃ | ethyl | 3,5-Cl₂—C₆H₃ |
| A.1897 | H | CH₃ | CH₃ | ethyl | 3,5-(CH₃)₂—C₆H₃ |
| A.1898 | H | CH₃ | CH₃ | ethyl | 2-F-4-Cl—C₆H₃ |
| A.1899 | H | CH₃ | CH₃ | ethyl | 2-Cl-4-F—C₆H₃ |
| A.1900 | H | CH₃ | CH₃ | ethyl | 3,4-F₂—C₆H₃ |
| A.1901 | H | CH₃ | CH₃ | ethyl | 3,4-Cl₂—C₆H₃ |
| A.1902 | H | CH₃ | CH₃ | ethyl | 2,3-F₂—C₆H₃ |

Et = ethyl

TABLE B

| No. | X | R³ | R⁴ | Rᵃ' |
|---|---|---|---|---|
| B. 1 | N(COOCH₃)-OCH₃ | H | CH₃ | H |
| B. 2 | C(COOCH₃)=COCH₃ | H | CH₃ | H |
| B. 3 | C(COOCH₃)=NOCH₃ | H | CH₃ | H |
| B. 4 | C(COOCH₃)=C-CH₃ | H | CH₃ | H |
| B. 5 | C(CONHCH₃)=NOCH₃ | H | CH₃ | H |
| B. 6 | N(COOCH₃)-OCH₃ | H | C₆H₅ | H |

TABLE B-continued

| No. | X | R³ | R⁴ | Rᵃ' |
|---|---|---|---|---|
| B. 7 | C(COOCH₃)=COCH₃ | H | C₆H₅ | H |
| B. 8 | C(COOCH₃)=NOCH₃ | H | C₆H₅ | H |
| B. 9 | C(COOCH₃)=C-CH₃ | H | C₆H₅ | H |
| B. 10 | C(CONHCH₃)=NOCH₃ | H | C₆H₅ | H |
| B. 11 | N(COOCH₃)-OCH₃ | H | 4-F-C₆H₄ | H |
| B. 12 | C(COOCH₃)=COCH₃ | H | 4-F-C₆H₄ | H |
| B. 13 | C(COOCH₃)=NOCH₃ | H | 4-F-C₆H₄ | H |
| B. 14 | C(COOCH₃)=C-CH₃ | H | 4-F-C₆H₄ | H |
| B. 15 | C(CONHCH₃)=NOCH₃ | H | 4-F-C₆H₄ | H |
| B. 16 | N(COOCH₃)-OCH₃ | H | CH₃ | CH₃ |
| B. 17 | C(COOCH₃)=COCH₃ | H | CH₃ | CH₃ |
| B. 18 | C(COOCH₃)=NOCH₃ | H | CH₃ | CH₃ |
| B. 19 | C(COOCH₃)=C-CH₃ | H | CH₃ | CH₃ |
| B. 20 | C(CONHCH₃)=NOCH₃ | H | CH₃ | CH₃ |
| B. 21 | N(COOCH₃)-OCH₃ | H | C₆H₅ | CH₃ |
| B. 22 | C(COOCH₃)=COCH₃ | H | C₆H₅ | CH₃ |
| B. 23 | C(COOCH₃)=NOCH₃ | H | C₆H₅ | CH₃ |
| B. 24 | C(COOCH₃)=C-CH₃ | H | C₆H₅ | CH₃ |
| B. 25 | C(CONHCH₃)=NOCH₃ | H | C₆H₅ | CH₃ |
| B. 26 | N(COOCH₃)-OCH₃ | H | 4-F-C₆H₄ | CH₃ |
| B. 27 | C(COOCH₃)=COCH₃ | H | 4-F-C₆H₄ | CH₃ |
| B. 28 | C(COOCH₃)=NOCH₃ | H | 4-F-C₆H₄ | CH₃ |
| B. 29 | C(COOCH₃)=C-CH₃ | H | 4-F-C₆H₄ | CH₃ |
| B. 30 | C(CONHCH₃)=NOCH₃ | H | 4-F-C₆H₄ | CH₃ |
| B. 31 | N(COOCH₃)-OCH₃ | CH₃ | CH₃ | H |
| B. 32 | C(COOCH₃)=COCH₃ | CH₃ | CH₃ | H |
| B. 33 | C(COOCH₃)=NOCH₃ | CH₃ | CH₃ | H |
| B. 34 | C(COOCH₃)=C-CH₃ | CH₃ | CH₃ | H |
| B. 35 | C(CONHCH₃)=NOCH₃ | CH₃ | CH₃ | H |
| B. 36 | N(COOCH₃)-OCH₃ | CH₃ | C₆H₅ | H |
| B. 37 | C(COOCH₃)=COCH₃ | CH₃ | C₆H₅ | H |
| B. 38 | C(COOCH₃)=NOCH₃ | CH₃ | C₆H₅ | H |
| B. 39 | C(COOCH₃)=C-CH₃ | CH₃ | C₆H₅ | H |
| B. 40 | C(CONHCH₃)=NOCH₃ | CH₃ | C₆H₅ | H |
| B. 41 | N(COOCH₃)-OCH₃ | CH₃ | 4-F-C₆H₄ | H |
| B. 42 | C(COOCH₃)=COCH₃ | CH₃ | 4-F-C₆H₄ | H |
| B. 43 | C(COOCH₃)=NOCH₃ | CH₃ | 4-F-C₆H₄ | H |
| B. 44 | C(COOCH₃)=C-CH₃ | CH₃ | 4-F-C₆H₄ | H |
| B. 45 | C(CONHCH₃)=NOCH₃ | CH₃ | 4-F-C₆H₄ | H |
| B. 46 | N(COOCH₃)-OCH₃ | CH₃ | CH₃ | CH₃ |
| B. 47 | C(COOCH₃)=COCH₃ | CH₃ | CH₃ | CH₃ |
| B. 48 | C(COOCH₃)=NOCH₃ | CH₃ | CH₃ | CH₃ |
| B. 49 | C(COOCH₃)=C-CH₃ | CH₃ | CH₃ | CH₃ |
| B. 50 | C(CONHCH₃)=NOCH₃ | CH₃ | CH₃ | CH₃ |
| B. 51 | N(COOCH₃)-OCH₃ | CH₃ | C₆H₅ | CH₃ |
| B. 52 | C(COOCH₃)=COCH₃ | CH₃ | C₆H₅ | CH₃ |
| B. 53 | C(COOCH₃)=NOCH₃ | CH₃ | C₆H₅ | CH₃ |
| B. 54 | C(COOCH₃)=C-CH₃ | CH₃ | C₆H₅ | CH₃ |
| B. 55 | C(CONHCH₃)=NOCH₃ | CH₃ | C₆H₅ | CH₃ |
| B. 56 | N(COOCH₃)-OCH₃ | CH₃ | 4-F-C₆H₄ | CH₃ |
| B. 57 | C(COOCH₃)=COCH₃ | CH₃ | 4-F-C₆H₄ | CH₃ |
| B. 58 | C(COOCH₃)=NOCH₃ | CH₃ | 4-F-C₆H₄ | CH₃ |
| B. 59 | C(COOCH₃)=C-CH₃ | CH₃ | 4-F-C₆H₄ | CH₃ |
| B. 60 | C(CONHCH₃)=NOCH₃ | CH₃ | 4-F-C₆H₄ | CH₃ |

TABLE C

| No. | X | R² | R³ | R⁴ | Rᵃ |
|---|---|---|---|---|---|
| C. 1 | N(COOCH₃)-OCH₃ | H | H | CH₃ | H |
| C. 2 | C(COOCH₃)=COCH₃ | H | H | CH₃ | H |
| C. 3 | C(COOCH₃)=NOCH₃ | H | H | CH₃ | H |
| C. 4 | C(COOCH₃)=C-CH₃ | H | H | CH₃ | H |
| C. 5 | C(CONHCH₃)=NOCH₃ | H | H | CH₃ | H |
| C. 6 | N(COOCH₃)-OCH₃ | H | H | C₆H₅ | H |
| C. 7 | C(COOCH₃)=COCH₃ | H | H | C₆H₅ | H |
| C. 8 | C(COOCH₃)=NOCH₃ | H | H | C₆H₅ | H |
| C. 9 | C(COOCH₃)=C-CH₃ | H | H | C₆H₅ | H |
| C. 10 | C(CONHCH₃)=NOCH₃ | H | H | C₆H₅ | H |
| C. 11 | N(COOCH₃)-OCH₃ | H | H | 4-F-C₆H₄ | H |
| C. 12 | C(COOCH₃)=COCH₃ | H | H | 4-F-C₆H₄ | H |
| C. 13 | C(COOCH₃)=NOCH₃ | H | H | 4-F-C₆H₄ | H |
| C. 14 | C(COOCH₃)=C-CH₃ | H | H | 4-F-C₆H₄ | H |
| C. 15 | C(CONHCH₃)=NOCH₃ | H | H | 4-F-C₆H₄ | H |

TABLE C-continued

| No. | X | R² | R³ | R⁴ | Rᵃ |
|---|---|---|---|---|---|
| C. 16 | N(COOCH₃)-OCH₃ | H | CH₃ | CH₃ | CH₃ |
| C. 17 | C(COOCH₃)=COCH₃ | H | CH₃ | CH₃ | CH₃ |
| C. 18 | C(COOCH₃)=NOCH₃ | H | CH₃ | CH₃ | CH₃ |
| C. 19 | C(COOCH₃)=C-CH₃ | H | CH₃ | CH₃ | CH₃ |
| C. 20 | C(CONHCH₃)=NOCH₃ | H | CH₃ | CH₃ | CH₃ |
| C. 21 | N(COOCH₃)-OCH₃ | H | CH₃ | C₆H₅ | CH₃ |
| C. 22 | C(COOCH₃)=COCH₃ | H | CH₃ | C₆H₅ | CH₃ |
| C. 23 | C(COOCH₃)=NOCH₃ | H | CH₃ | C₆H₅ | CH₃ |
| C. 24 | C(COOCH₃)=C-CH₃ | H | CH₃ | C₆H₅ | CH₃ |
| C. 25 | C(CONHCH₃)=NOCH₃ | H | CH₃ | C₆H₅ | CH₃ |
| C. 26 | N(COOCH₃)-OCH₃ | H | CH₃ | 4-F-C₆H₄ | CH₃ |
| C. 27 | C(COOCH₃)=COCH₃ | H | CH₃ | 4-F-C₆H₄ | CH₃ |
| C. 28 | C(COOCH₃)=NOCH₃ | H | CH₃ | 4-F-C₆H₄ | CH₃ |
| C. 29 | C(COOCH₃)=C-CH₃ | H | CH₃ | 4-F-C₆H₄ | CH₃ |
| C. 30 | C(CONHCH₃)=NOCH₃ | H | CH₃ | 4-F-C₆H₄ | CH₃ |
| C. 31 | N(COOCH₃)-OCH₃ | H | CH₃ | C₆H₅ | ethyl |
| C. 32 | C(COOCH₃)=COCH₃ | H | CH₃ | C₆H₅ | ethyl |
| C. 33 | C(COOCH₃)=NOCH₃ | H | CH₃ | C₆H₅ | ethyl |
| C. 34 | C(COOCH₃)=C-CH₃ | H | CH₃ | C₆H₅ | ethyl |
| C. 35 | C(CONHCH₃)=NOCH₃ | H | CH₃ | C₆H₅ | ethyl |

The compounds I are suitable as fungicides. They have excellent activity against a broad spectrum of phytopathogenic fungi, in particular from the classes of the Ascomycetes, Deuteromycetes, Phycomycetes and Basidiomycetes. Some of them act systemically and can be employed in crop protection as foliar- and soil-acting fungicides.

They are especially important for controling a large number of fungi in a variety of crop plants such as wheat, rye, barley, oats, rice, maize, grass, bananas, cotton, soya, coffee, sugar cane, grape vines, fruit species, ornamentals and vegetable species such as cucumbers, beans, tomatoes, potatoes and cucurbits, and also in the seeds of these plants.

Specifically, they are suitable for controling the following plant diseases:

Alternaria species in vegetables and fruit,
*Botrytis cinerea* (gray mold) in strawberries, vegetables, ornamentals and grape vines,
*Cercospora arachidicola* in groundnuts,
*Erysiphe cichoracearum* and *Sphaerotheca fuliginea* in cucurbits,
*Erysiphe graminis* (powdery mildew) in cereals,
Fusarium and Verticillium species in a variety of plants,
Helminthosporium species in cereals,
Mycosphaerella species in bananas,
*Phytophthora infestans* in potatoes and tomatoes,
*Plasmopara viticola* in grape vines,
*Podosphaera leucotricha* in apples,
*Pseudocercosporella herpotrichoides* in wheat and barley,
Pseudoperonospora species in hops and cucumbers,
Puccinia species in cereals,
*Pyricularia oryzae* in rice,
Rhizoctonia species in cotton, rice and lawns,
*Septoria nodorum* in wheat,
*Uncinula necator* in grape vines,
Ustilago species in cereals and sugar cane, and
*Venturia inaequalis* (scab) in apples.

The compounds I are also suitable for controlling harmful fungi such as *Paecilomyces variotii* in the protection of materials (for example wood, paper, paint dispersions, fibers or tissues) and in the protection of stored products.

The compounds I are employed by treating the fungi or the plants, seeds, materials or the soil to be protected against fungal attack with a fungicidally effective amount of the active compounds. The application is carried out before or after the infection of the materials, plants or seeds by the fungi.

The fungicidal compositions generally comprise from 0.1 to 95, preferably from 0.5 to 90, % by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds of the formula I are also suitable for the efficient control of animal pests from the classes of the insects, arachnids and nematodes. They can be used for controling animal pests in crop protection and in the sectors of hygiene, protection of stored products and in the veterinary sector. They are particularly suitable for controling the following animal pests:

Insects from the order of the lepidopterons (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), eg. *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria,* dipterons (Diptera), eg. *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), eg. *Frankliniella fusca, Frankliniella occidentalis, Frankliniella tritici, Scirtothrips citri, Thrips oryzae, Thrips palmi* and *Thrips tabaci,* hymenopterons (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterons (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterons (Homoptera), eg. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), eg. *Calotermes flavicollis, Leucotermes flavipes, Reticulitermes lucifugus* and *Termes natalensis,* orthopterons (Orthoptera), eg. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus*

*spretus, Nomadacris septemfasciata, Periplaneta americana, Schistocerca americana, Schistocerca peregrina, Stauronotus maroccanus* and Tachycines asynamorus, Arachnoidea such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root ball nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem and leaf nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

For controling animal pests under free range conditions, the application rate of active compound is from 0.1 to 2.0, preferably 0.2 to 1.0, kg/ha.

The compounds I can be converted into the customary formulations, eg. solutions, emulsions, suspensions, dusts, powders, pastes and granules. The use form depends on the specific intended use; in any case, it should guarantee fine and uniform distribution of the compound according to the invention.

The formulations are prepared in a known manner, eg. by extending the active compound with solvents and/or carriers, if desired using emulsifiers and dispersants, it being possible to use other organic solvents as auxiliary solvents if water is used as the diluent. Suitable auxiliaries for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolin, clays, talc, chalk) and ground synthetic minerals (eg. finely divided silica, silicates); emulsifiers such as nonionic and anionic emulsifiers (eg. polyoxyethylene fatty alcohol ethers, alkylsulfonates and arylsulfonates), and dispersants such as ligninsulfite waste liquors and methylcellulose.

Suitable surfactants are the alkali metal, alkaline earth metal and ammonium salts of lignosulfonic acid, naphthalenesulfonic acid, phenolsulfonic acid, and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Suitable for preparing directly sprayable solutions, emulsions, pastes or oil dispersions are petroleum fractions having medium to high boiling points, such as kerosine or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or joint grinding the active substances with a solid carrier.

Granules, for example coated granules, impregnated granules and homogenous granules, can be prepared by binding the active compounds to solid carriers. Solid carriers are, for example, mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100,000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should guarantee very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with good success in the ultra-low-volume method (ULV), it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zink ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2))benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis-1-(2,2,2-trichloroethyl) formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-

(1H-1,2,4-triazol-1-yl)-2-butanol, (2RS, 3RS)-1-(3-(2-chlorophenyl)-2-(4-fluorophenyl)oxiran-2-ylmethyl-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene strobilurins, such as methyl E-methoximino-[α-(o-tolyloxy)-o-tolyl]acetate, methyl E-2-{2-[6-(2-cyanophenoxy)-pyridimin-4-yloxy]-phenyl}-3-methoxyacrylate, N-methyl E-methoximino-[α-(2-phenoxyphenyl)]acetamide, methyl-E-methoximino-[α-(2,5-dimethylphenoxy)-o-tolyl]acetamide, anilinopyrimidines, such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxyphenyl)acryloylmorpholine.

and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole.

Preference is given to the fungicidal activity.

SYNTHESIS EXAMPLES

The procedures given in the synthesis examples below were used to obtain further compounds I by appropriate modification of the starting materials. The compounds obtained in this manner are listed in the tables that follow, together with physical data.

Example 1

Preparation of 2,2-dimethoxy-1-phenylpropan-1-one 1.2 g of trimethoxymethane and 8.7 ml of 25% strength by weight ethanolic HCl solution were added to 14.8 g of 1-phenylpropane-1,2-dione dissolved in 27.5 ml of methanol. The reaction mixture was stirred at 20 to 25° C. for 2 hours, and the solvent was then removed by distillation. The residue was taken up in methyl tert-butyl ether (MTBE) and the solution was washed with water. The organic phases were dried and the solvent removed by distillation. 18.2 g of product were obtained as a clear oil.

$^1$H NMR (CDCl$_3$): 2.6 (s, 3H); 3.3 (s, 6H); 7.4–7.6 (m, 3H); 8.2 ppm (m, 2H).

Example 2

Preparation of [1-(1,1-dimethoxyethyl)propenyl]benzene

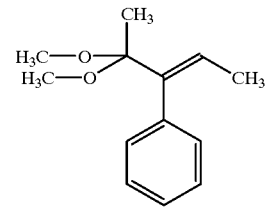

At 5° C., a solution of 2.5 g of potassium tert-butoxide in 25 ml of tetrahydrofuran (THF) was added dropwise to 8.2 g of ethyltriphenylphosphonium bromide dissolved in 50 ml of THF. The mixture was then stirred at 5° C. for about 10 min, and a solution of 3.9 g of 2,2-dimethoxy-1-phenylpropan-1-one from Example 1 in 10 ml of THF was added dropwise. The reaction mixture was stirred at 20 to 25° C. for 72 h and then admixed with about 300 ml of water and extracted with methyl tert-butyl ether (MTBE). The organic phases were washed with water, dried and freed of the solvent. Silica gel chromatography (MTBE/cyclohexane 1:10) of the residue gave 2.2 g of product as an isomer mixture which can be further reacted without purification.

Example 3

Preparation of 3-phenylpent-3-ene 2-oxime

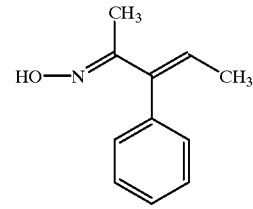

15.5 g of hydroxylammonium hydrochloride and 17.6 g of pyridine were initially charged in 140 ml of methanol. A solution of 30.7 g of the [1-(1,1-dimethoxyethyl)propenyl]benzene obtained from Example 2 in 140 ml of methanol was added dropwise and the mixture is stirred at 20 to 25° C. for 72 h. The reaction mixture was taken up in about 1.5 liters of NaCl solution and extracted with methyl tert-butyl ether (MTBE). The organic phases were washed with 5% strength by weight of hydrochloric acid and then with water. After drying and removal of the solvent by distillation, this gave 14.5 g of product as a light-yellow powder of mp. 99–101°C.

$^1$H NMR (CDCl$_3$): 1.6 (d, 3H); 2.0 (s,3H); 6.2 (q, 1H); 7.0–7.4 (m, 5H); 8.5 ppm (s, 1H).

Example 4

Preparation of methyl (E)-2-methoxyimino-2-(3-phenylpent-3-ene-2-iminooxymethyl)phenylacetate

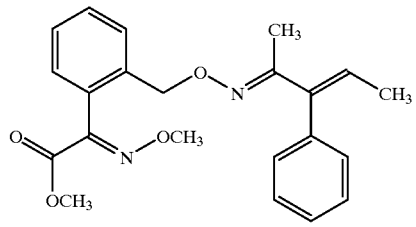

25 g (142 mmol) of the oxime obtained from Example 3 dissolved in 100 ml of dimethylformamide (DMF) were admixed with 25 g of 30% strength by weight of a methanolic sodium methoxide solution. The mixture was stirred at 20 to 25° C. for 15 min and then 40.8 g (142 mmol) of methyl 2-bromomethylphenylglyoxylate O-methyloxime dissolved in 100 ml of DMF were added dropwise. The reaction mixture was stirred at 20 to 25° C. for about 3 h, poured into ice-water and extracted with methyl tert-butyl ether (MTBE). The organic phases were washed, dried and freed of the solvent. Silica gel chromatography (MTBE/cyclohexane 1:9) of the residue gave 32 g of the title compound.

$^1$H NMR (CDCl$_3$): 1.6 (d, 3H); 3.8 (s, 3H); 4.0 (s, 3H); 5.0 (s, 2H); 6.2 (q, 1H); 7.1–7.5 ppm (m, 9H).

Example 5

Preparation of (E)-2-methoxyimino-2-[(3-phenyl)pent-3-ene-2-iminooxymethyl]phenyl-N-methylacetamide

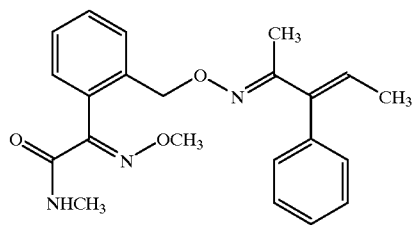

12.4 g (32.6 mmol) of the ester obtained from Example 4 were dissolved in 200 ml of tetrahydrofuran (THF), and 25.3 g of a 40% strength by weight aqueous methylamine solution were added dropwise. The solution was stirred at 20 to 25° C. for 2 h, poured into ice-water and extracted with methyl tert-butyl ether (MTBE). The organic phases were washed, dried and freed of the solvent. Silica gel chromatography (MTBE/cyclohexane 1:3) of the residue gave 7.7 g of product.

$^1$H NMR (CDCl$_3$): 1.6 (d, 3H); 1.8 (s, 3H); 2.85 (d, 3H); 3.9 (s, 3H); 4.95 (s, 2H); 6.1 (q, 1H); 6.7 (s, 1H); 7.1–7.5 ppm (m, 9H).

Example 6

Preparation of (E)-2-methoxyimino-2-[1-(3-methyl-2-phenyloxiranyl)ethylideneiminooxymethyl]phenyl-N-methylacetamide

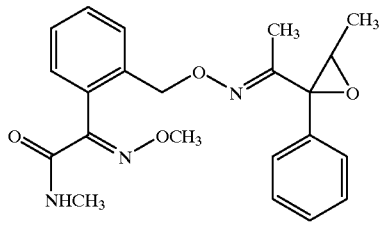

20.3 g (53.6 mmol) of the amide obtained from Example 5 were dissolved in 250 ml of methylene chloride. 24.4 g (77.7 mmol) of 3-chloroperbenzoic acid were added and the reaction mixture was stirred at 20 to 25° C. for 18 h. The reaction mixture was poured into water and washed with sodium thiosulfate and sodium hydroxide solution and then with water. The organic phase was separated off, dried and freed of the solvent. Silica gel chromatography (MTBE/cyclohexane 1:3) of the residue gave 21.3 g of the product as an oil.

$^1$H NMR (CDCl$_3$): 1.0 (d, 3H); 1.8 (s, 3H); 2.8 (d, 3H); 3.7 (q, 1H); 4.0 (s, 3H); 5.0 (s, 2H); 6.7 (s, 1H); 6.7 (s, 1H); 7.2–7.5 ppm (m, 9H).

Example 7

Preparation of methyl (E)-2-methoxyimino-2-[1-(1-phenylcyclopropyl)ethylideneiminooxymethyl]phenyl acetate

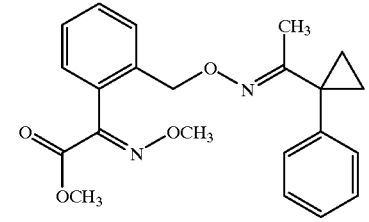

A solution of 3.5 g of 1-(1-phenylcyclopropyl)ethylidene oxime in 10 ml of DMF was added dropwise to 0.53 g of sodium hydride in 30 ml of anhydrous dimethylformamide (DMF). The mixture was stirred at 60° C. for 2 hours and 4.2 g of methyl 2-bromomethylphenylglyoxylate dissolved in 20 ml of DMF were then added dropwise at 0° C. The solution was stirred at 20 to 25° C. overnight, poured into ice-water and extracted with methyl tert-butyl ether (MTBE). The organic phases were washed, dried and freed of the solvent. Silica gel chromatography (toluene) of the residue gave 3 g of the title compound as yellow crystals of mp. 67–70° C.

$^1$H NMR (CDCl$_3$): 0.9 (m, 2H); 1.2 (m, 2H); 1.8 (s, 3H); 3.8 (s, 3H); 4.0 (s, 3H); 5.0 (s, 2H); 7.1–7.6 (m, 9H).

TABLE I

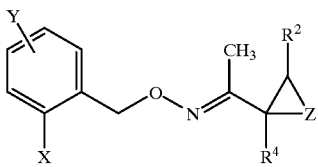

I.1: X = N(COOCH₃)—OCH₃
I.2: X = C(COOCH₃)=CH—OCH₃
I.3: X = C(COOCH₃)=N—OCH₃
I.4: X = C(CONHCH₃)=N—OCH₃
I.5: X = C(COOCH₃)=CH—CH₃

| No. | X | Y | Z | $R^2$ | $R^4$ | Phys. data (Mp.[° C.], IR [cm$^{-1}$], $^1$H NMR [ppm/CDCl₃]) |
|---|---|---|---|---|---|---|
| 1 | I.4 | H | O | CH₃ | C₆H₅ | 1,0 (3H); 1.7 (3H); 2.95 (3H); 3.7 (1H); 4.0 (3H); 5.0 (2H); 6.7 (NH) |
| 2 | I.1 | H | O | CH₃ | C₆H₅ | 1.0 (3H); 1.8 (3H) 3.7 (3H); 3.8 (3H); 5.2 (2H); 7.2–7.5 (9H) |
| 3 | I.4 | H | O | CH₃ | CH₃ | 1.3 (3H); 1.4 (3H); 1.6 (3H); 2.95 (3H); 3.1 (1H); 4.0 (3H); 5.0 (2H) |
| 4 | I.4 | H | O | C₆H₅ | CH₃ | 1673, 1526, 1037, 979 |
| 5 | I.3 | H | CH₂ | H | C₆H₅ | 67–70 |
| 6 | I.4 | H | CH₂ | H | C₆H₅ | 0.9 (2H); 1.2 (2H); 1.8 (3H); 2.8 (3H); 4.0 (3H); 5.0 (2H); 6.8 (NH); 7.1–7.6 (9H) |
| 7 | I.3 | H | CH₂ | H | 4-Cl—C₆H₄ | 0.95 (2H); 1.25 (2H); 1.8 (3H); 3.8 (3H); 4.05 (3H); 5.0 (2H); 7.1–7.4 (8H) |
| 8 | I.4 | H | CH₂ | H | 4-Cl—C₆H₄ | 0.9 (2H); 1.25 (2H); 1.8 (3H); 2.85 (3H); 3.9 (3H); 4.9 (2H); 6.6 (NH); 7.1–7.4 (8H) |
| 9 | I.3 | H | O | —CH₂CH₃ | C₆H₅ | 1729, 1449, 1219, 1970 |
| 10 | I.4 | H | O | —CH₂CH₃ | C₆H₅ | 1675, 1525, 1449, 1038 |
| 11 | I.1 | H | O | —CH₂CH₃ | C₆H₅ | 1740, 1440, 1335, 1028 |
| 12 | I.3 | H | O | —CH₂CH₂CH₃ | C₆H₅ | 1729, 1449, 1219, 1070 |
| 13 | I.4 | H | O | —CH₂CH₂CH₃ | C₆H₅ | 1674, 1525, 1448, 1058 |
| 14 | I.1 | H | O | —CH₂CH₂CH₃ | C₆H₅ | 1740, 1441, 1337, 1105 |
| 15 | I.3 | H | O | —CH₂CH₂CH₂CH₃ | C₆H₅ | 1729, 1448, 1219, 1070 |
| 16 | I.4 | H | O | —CH₂CH₂CH₂CH₃ | C₆H₅ | 1674, 1524, 1448, 1038 |
| 17 | I.1 | H | O | —CH₂CH₂CH₂CH₃ | C₆H₅ | 1740, 1441, 1336, 1195 |
| 18 | I.3 | H | O | —CH₃ | 4-F—C₆H₄ | 1728, 1508, 1221, 1970 |
| 19 | I.4 | H | O | —CH₃ | 4-F—C₆H₄ | 1673, 1509, 1222, 1937 |

Examples of the Activity Against Harmful Fungi

The fungicidal activity of the compounds of the formula I was demonstrated by the following experiments:

The active compounds were prepared as a 10% strength emulsion in a mixture of 63% by weight of cyclohexanone and 27% by weight of emulsifier and diluted with water to the desired concentration.

The compounds A and B, known from EP-A 463 488 as Nos. 56 of Tables I and II, served as comparative active compounds:

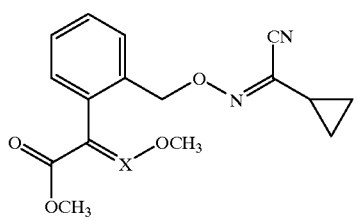

-continued

A: X = CH
B: X = N

Use Example 1—Activity Against Powdery Mildew of Wheat

Leaves of wheat seedlings cv. "Frühgold" in pots were sprayed to runoff point with an aqueous active compound preparation and, 24 hours after the spray coating had dried on, dusted with spores of powdery mildew of wheat (*Erysiphe graminis* forma specialis *tritici*). The test plants were subsequently placed in a greenhouse at from 20 to 22° C. and a relative atmospheric humidity of 75 to 80%. After 7 days, the extent of mildew development was determined visually as % infestation of the total leaf area.

In this test, the plants treated with 16 ppm of the compounds Nos. 1, 2, 3, 4, 9, 10, 11, 12, 13, 14 and 18 of Table I showed an infestation of no more than 15%, while the plants treated with 16 ppm of the comparative compounds A and B and the untreated plants showed an infestation of 40% and 80%, respectively.

Use Example 2 —Activity Against *Plasmopara viticola*

Leaves of potted vines cv. "Müller-Thurgau" were sprayed to runoff point with an aqueous active compound preparation. To assess the persistency of the substances, the plants were kept for 7 days in a greenhouse after the spray coating had dried on. Only then were the leaves inoculated with an aqueous zoospore suspension of *Plasmopara viticola*. The grape vines were then initially kept in a water vapor-saturated chamber at 24° C. for 48 hours and then in a greenhouse at 20–30° C. for 5 days. After this, the plants were once more kept in a humid chamber for 16 hours to promote sporangiophore eruption. The extent of the infestation on the undersides of the leaves was then assessed visually.

In this test, the plants treated with 16 ppm of the compounds Nos. 1, 4, 5, 6, 7, 8, 9, 10, 12, 13, 16, 18 and 19 of Table I showed a maximum infestation of 10%, while the plants treated with 16 ppm of comparative compound B and the untreated plants showed an infestation of 60% and 80%, respectively.

Use Example 3 —Activity Against *Pyricularia oryzae* (protective)

Leaves of potted rice seedlings cv. "Tai-Nong 67" were sprayed to runoff point with an aqueous active compound preparation. The next day, the plants were inoculated with an aqueous spore suspension of *Pyricularia oryzae*. The test plants were subsequently kept in climatized chambers at 22–24° C. and 95–99% relative atmospheric humidity for 6 days. The extent of the infestation of the leaves was then determined visually.

In this test, the plants treated with 16 ppm of the compounds Nos. 1, 2, 4, 6, 7, 8, 9, 10, 11, 12, 13, 14, 15, 16, 18 and 19 of Table I showed a maximum infestation of 15%, while the plants treated with 16 ppm of comparative compound B and the untreated plants showed an infestation of 40% and 80%, respectively.

Examples of the Activity Against Animal Pests

The activity of the compounds of the formula I against animal pests was demonstrated by the following experiments:

The active compounds were prepared
a. as a 0.1% strength solution in acetone or
b. as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Wettol® EM (nonionic emulsifier based on ethoxylated castor oil)

and diluted with acetone in the case of a. or with water in the case of b. to the desired concentration.

After conclusion of the tests, the lowest concentration in each case was determined at which the compounds still caused 80–100% inhibition or mortality in comparison to untreated control tests (activity threshold or minimum concentration).

We claim:

1. A benzyloxyimino compound of formula I,

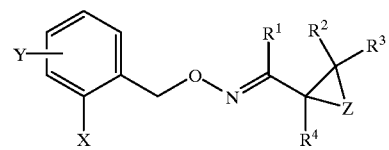

I wherein
X is $N(COOCH_3)$—$OCH_3$, $C(COOCH_3)$=$CH$—$OCH_3$, $C(COOCH_3)$=$N$—$OCH_3$, $C(CONHCH_3)$=$N$—$OCH_3$ or $C(COOCH_3)$=$CH$—$CH_3$;
Y is hydrogen, halogen, $C_1$–$C_4$-alkyl, $C_1$–$C_4$-halolakyl or $C_1$–$C_4$-alkoxy;
Z is oxygen or $CH_2$;
$R^1$ is halogen, $C_1$–$C_4$-alkyl, $C_1$–$C_4$-haloalkyl or $C_1$–$C_4$-alkoxy;
$R^2$ is hydrogen;
$R^3$ is hydrogen;
$R^4$ is $C_1$–$C_4$-alkyl or
  phenyl which is unsubstituted or carries from one to three substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=$N$—$OR^c$,
  wherein
  $R^b$ is hydrogen or $C_1$–$C_4$-alkyl and
  $R^c$ is $C_1$–$C_4$-alkyl, $C_3$–$C_4$-alkenyl or $C_3$–$C_4$-alkynyl,
wherein Z is not $CH_2$ if X is $C(COOCH_3)$=$CH$—$OCH_3$ or $C(COOCH_3)$=$N$—$OCH_3$ and $R^4$ is $C_1$–$C_4$-alkyl.

2. An oxime of formula II

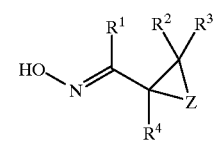

II wherein
Z is oxygen;
$R^1$ is halogen, $C_1$–$C_4$-alkyl, $C_1$–$C_4$-haloalkyl or $C_1$–$C_4$-alkoxy,
$R^2$ is hydrogen,
$R^3$ is hydrogen, and
$R^4$ is $C_1$–$C_4$-alkyl or
  phenyl with or without substitution by 1–3 substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=$N$—$OR^c$, wherein
  $R^b$ is hydrogen or $C_1$–$C_4$-alkyl and
  $R^c$ is $C_1$–$C_4$-alkyl, $C_3$–$C_4$-alkenyl or $C_3$–$C_4$-alkynyl.

3. The compound of formula I defined in claim 1, wherein $R^2$ and $R^3$ are each hydrogen.

4. The compound of formula I defined in claim 1, wherein X is $N(COOCH_3)$—$OCH_3$.

5. The compound of formula I defined in claim 1, wherein Z is oxygen, and $R^4$ is phenyl which is unsubstituted or carries from one to three substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=$N$—$OR^c$.

6. The oxime of formula II defined in claim 2, wherein $R^4$ is phenyl which is unsubstituted or carries from one to three 7. A benzyloxyimino compound of formula I,

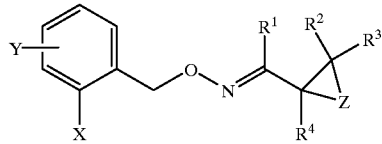

wherein
X is $N(COOCH_3)$—$OCH_3$;
Y is hydrogen, halogen, $C_1$–$C_4$-alkyl, $C_1$–$C_4$-halolakyl or $C_1$–$C_4$-alkoxy;
Z is oxygen or $CH_2$;
$R^1$ is halogen, $C_1$–$C_4$-alkyl, $C_1$–$C_4$-haloalkyl or $C_1$–$C_4$-alkoxy;
$R^2$ is hydrogen or $C_1$–$C_4$-alkyl;
$R^3$ is hydrogen or $C_1$–$C_4$-alkyl;
$R^4$ is $C_1$–$C_4$-alkyl or
phenyl which is unsubstituted or carries from one to three substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=N—$OR^c$,
wherein
$R^b$ is hydrogen or $C_1$–$C_4$-alkyl and
$R^c$ is $C_1$–$C_4$-alkyl, $C_3$–$C_4$-alkenyl or $C_3$–$C_4$-alkynyl.

8. A composition suitable for controlling animal pests or harmful fungi, comprising a solid or liquid carrier and the compound of formula I defined in claim 1.

9. The composition defined in claim 8, wherein X of the compound of formula I is $N(COOCH_3)$—$OCH_3$.

10. The composition defined in claim 8, wherein Z of the compound of formula I is oxygen, and $R^4$ is phenyl which is unsubstituted or carries from one to three substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=N—$OR^c$.

11. A composition suitable for controlling animal pests or harmful fungi, comprising a solid or liquid carrier and the compound of formula I defined in claim 7.

12. A method for controlling harmful fungi, which comprises treating the fungi or the materials, plants, the soil or seeds to be protected against attack by fungi with an effective amount of the compound of formula I defined in claim 1.

13. A method for controlling animal pests, which comprises treating the animal pests or the materials, plants, the soil or seeds to be protected against them with an effective amount of the compound of formula I defined in claim 1.

14. The method of claim 12, wherein X of the compound of formula I is $N(COOCH_3)$—$OCH_3$.

15. The method of claim 13, wherein X of the compound of formula I is $N(COOCH_3)$—$OCH_3$.

16. The method of claim 12, wherein Z of the compound of formula I is oxygen, and $R^4$ is phenyl which is unsubstituted or carries from one to three substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=N—$OR^c$.

17. The method of claim 13, wherein Z of the compound of formula I is oxygen, and $R^4$ is phenyl which is unsubstituted or carries from one to three substituents from the following group: halogen, $C_1$–$C_4$-alkyl, $C_1$–$C_4$-haloalkyl, $C_1$–$C_4$-alkoxy, $C_1$–$C_4$-haloalkoxy or $C(R^b)$=N—$OR^c$.

18. A method for controlling harmful fungi, which comprises treating the fungi or materials, plants, soil or seeds to be protected against attack by fungi with an effective amount of the compound of formula I defined in claim 7.

19. A method for controlling animal pests, which comprises treating the animal pests or materials, plants, soil or seeds to be protected against them with an effective amount of the compound of formula I defined in claim 7.

20. A process for preparing the compound of formula I defined in claim 1, which comprises reacting an oxime of formula II

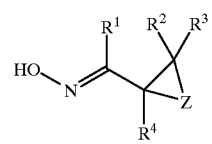

with a benzyl compound of formula III,

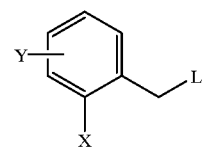

wherein L is a leaving group.

21. A process for preparing the compound of formula I defined in claim 1 wherein Z is oxygen, which comprises reacting a benzyl compound of formula III with an oxime of formula IV

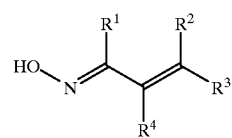

to give an oxime ether of formula V

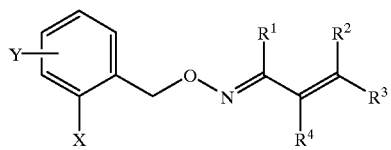

which is subsequently converted by oxidation into the compound of formula I.

* * * * *